(12) United States Patent
Lee et al.

(10) Patent No.: US 10,326,092 B2
(45) Date of Patent: Jun. 18, 2019

(54) ORGANIC ELECTRONIC ELEMENT USING A COMPOUND FOR ORGANIC ELECTRONIC ELEMENT, AND AN ELECTRONIC DEVICE THEREOF

(71) Applicant: DUK SAN NEOLUX CO., LTD., Cheonan-si, Chungcheongnam-do (KR)

(72) Inventors: Bumsung Lee, Cheonan-si (KR); Sunhee Lee, Cheonan-si (KR); Soungyun Mun, Yongin-si (KR); Daesung Kim, Yongin-si (KR); Gyumin Lee, Cheonan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 354 days.

(21) Appl. No.: 15/327,429

(22) PCT Filed: Jul. 17, 2015

(86) PCT No.: PCT/KR2015/007474
§ 371 (c)(1),
(2) Date: Jan. 19, 2017

(87) PCT Pub. No.: WO2016/013816
PCT Pub. Date: Jan. 28, 2016

(65) Prior Publication Data
US 2017/0162813 A1    Jun. 8, 2017

(30) Foreign Application Priority Data

Jul. 21, 2014 (KR) .................. 10-2014-0091658

(51) Int. Cl.
| | |
|---|---|
| H01L 51/50 | (2006.01) |
| C07C 211/54 | (2006.01) |
| C07C 211/57 | (2006.01) |
| C09K 11/06 | (2006.01) |
| H01L 27/32 | (2006.01) |

(52) U.S. Cl.
CPC .......... H01L 51/50 (2013.01); C07C 211/54 (2013.01); C07C 211/57 (2013.01); C09K 11/06 (2013.01); H01L 27/32 (2013.01); C09K 2211/1007 (2013.01); C09K 2211/1011 (2013.01); C09K 2211/1014 (2013.01); C09K 2211/1088 (2013.01); C09K 2211/1092 (2013.01); H01L 2251/10 (2013.01)

(58) Field of Classification Search
None
See application file for complete search history.

(56) References Cited

FOREIGN PATENT DOCUMENTS

| | | | |
|---|---|---|---|
| JP | 2000-247932 A | 9/2000 | |
| JP | 2012-195244 * | 10/2012 | ............. H01L 51/50 |
| KR | 10-0989307 B1 | 10/2010 | |
| KR | 10-1029082 B1 | 4/2011 | |
| KR | 10-1181281 B1 | 9/2012 | |

(Continued)

Primary Examiner — Gregory D Clark
(74) Attorney, Agent, or Firm — Vorys, Sater, Seymour & Pease LLP; Mih Suhn Koh

(57) ABSTRACT

Provided are a compound of Formula 1 and an organic electric element including a first electrode, a second electrode, and an organic material layer between the first electrode and the second electrode and comprising the compound, the element showing improved luminescent efficiency, stability, and life span.

12 Claims, 1 Drawing Sheet

(56) References Cited

FOREIGN PATENT DOCUMENTS

| KR | 10-2013-0028671 A | 3/2013 |
| KR | 10-2013-0106255 A | 9/2013 |
| KR | 10-1389527 B1 | 4/2014 |
| KR | 10-1405725 B1 | 6/2014 |

* cited by examiner

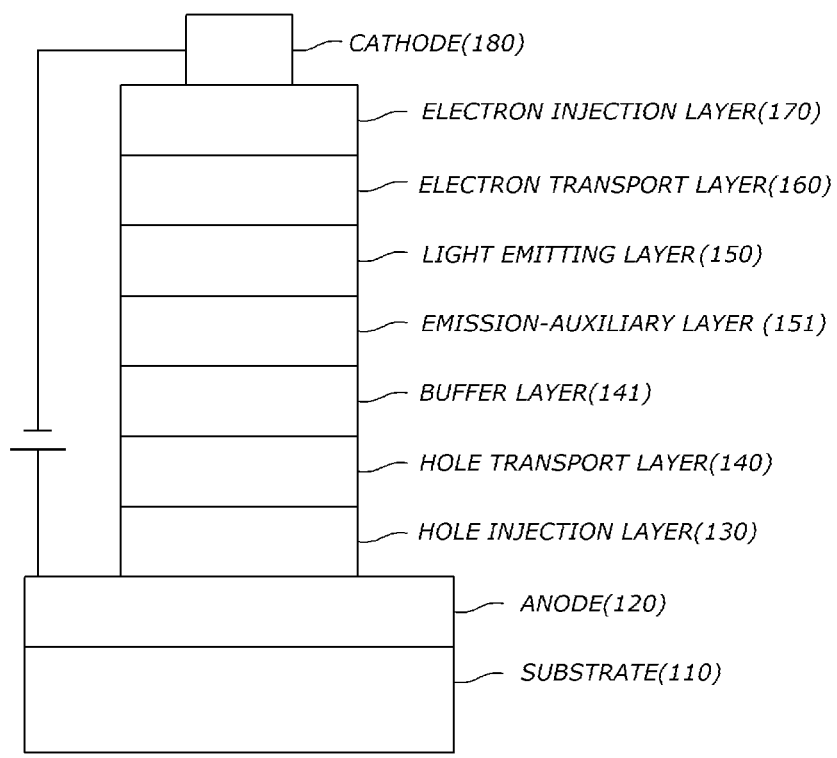

ORGANIC ELECTRONIC ELEMENT USING A COMPOUND FOR ORGANIC ELECTRONIC ELEMENT, AND AN ELECTRONIC DEVICE THEREOF

CROSS-REFERENCE TO RELATED APPLICATION

This patent application claims benefit under 35 U.S.C. 119, 120, 121, or 365, and is a National Stage entry from International Application No. PCT/KR2015/007474, filed Jul. 17, 2015, which claims priority to Korean Patent Application No. 10-2014-0091658 filed on Jul. 21, 2014, the contents of which are hereby incorporated by reference for all purposes as if fully set forth herein.

BACKGROUND

Technical Field

The present invention relates to organic electrical element using compound for organic electrical element, and electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer is formed between the hole transport layer and a light emitting layer, and it is time to develop different material of emission-auxiliary layers according to respective pixel-domain (R, G, B) of light emitting layers.

In general, an exciton is formed by recombination of an electron which transfers from an electron transport layer to a light emitting layer and a hole which transfers from a hole transport layer to the light emitting layer.

However, it mainly has a low T1 value because a material used in a hole transporting layer should have a low HOMO value, thereby excitons generated from a light emitting layer are transported to the hole transporting layer, resulting in a charge unbalance in the light emitting layer. Thus, light emission occurs in the hole transporting layer or at an interface of the hole transporting layer so that color purity, efficiency and lifespan of the organic electroluminescent device are reduced.

Further, when a material with rapid hole mobility is used in order to reduce a driving voltage in the organic electroluminescent device, it shows tendency to lower the efficiency. The general organic electric element has a hole mobility higher than an electron mobility. This causes a charge unbalance in the light emitting layer resulting in low emitting efficiency and lifespan.

Therefore, in order to solve a problem of a hole transport layer, it needs to form the light emitting layer as material which has a hole transport ability to have a proper driving voltage, high T1 (electron block) value and wide bandgap.

These requirements are not satisfied only by structural characteristics of a core of the emission-auxiliary layer material, and it is possible to satisfy these requirements when characteristics of core and sub substituents have an appropriate combination. Therefore, it is necessary strongly to develop of the material for the emission-auxiliary layer having high T1 energy value and wide band gap, to improve efficiency and lifespan of the organic electric element.

In order to allow an organic electric element to fully exhibit the above-mentioned excellent features, it should be prerequisite to support a material forming an organic material layer of the element, for example, a hole injection material, a hole transport material, a light emitting material, an electron transport material, an electron injection material, an emission-auxiliary layer material or the like, by a stable and efficient material. However, such a stable and efficient organic material layer material for an organic electric element has not yet been fully developed. Accordingly, there is a continuous need to develop new materials for an organic material layer, specially, there are strong needs to develop materials for an emission-auxiliary layer and a hole transport layer.

SUMMARY

In order to solve one or more of the above-mentioned problems occurring in the prior art, an aspect of the present invention provides an organic electrical element comprising compound which can improve a luminescence efficiency, lower a driving voltage, make thermal-resistance high, and improve color purity and lifespan of the organic electrical element, and an electronic device including the organic electric element.

In accordance with an aspect of the present invention, there is provided an organic electrical element comprising the compound represented by the following Formula, and an electronic device including the organic electrical element.

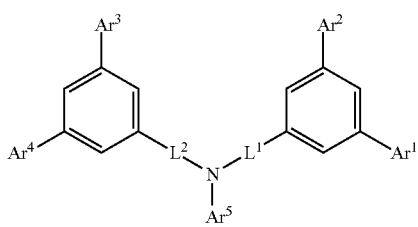

In another aspect of the present invention, there is provided an organic electrical element comprising a first electrode, a second electrode, and an organic material layer formed between the first electrode and the second electrode and comprising an emission-auxiliary layer and a light emitting layer, wherein the emission-auxiliary layer comprises compound represented by the above Formula.

By employing the compound of the present invention, the organic electrical element according to one or more embodiments of the present invention can have improved luminescence efficiency, low driving voltage, high heat-resistant, improved color purity and lifespan.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component. In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), iodine (I) and so on.

Unless otherwise stated, the term "alkyl" or "alkyl group" as used herein has a single bond of 1 to 60 carbon atoms, and means aliphatic functional radicals including a linear alkyl group, a branched chain alkyl group, a cyclo alkyl group (alicyclic), or an alkyl group substituted with a cyclo alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cyclo alkyl" as used herein means, but not limited to, alkyl forming a ring having 3 to 60 carbon atoms.

The term "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbon to which they are attached to form spiro compound.

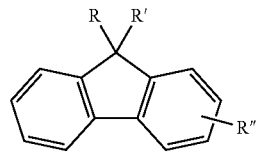

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

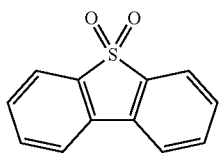 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an aryl alkoxy means an alkoxy substituted with an aryl, an alkoxyl carbonyl means a carbonyl substituted with an alkoxyl, and an aryl carbonyl alkenyl also means an alkenyl substitutes with an aryl carbonyl, wherein the aryl carbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

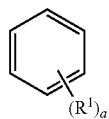

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different each other, and are linked to the benzene ring as follows. when a is an integer of 4 to 6, the substituents $R^1$s are linked to carbon atom of the benzene ring in a similar manner to that. Meanwhile, hydrogen atoms linked to carbon constituting the benzene ring may not be represented as usual.

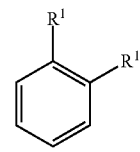

(a-2)

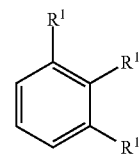

(a-3)

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer therebetween which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, at least one of the layers may not be formed. The organic material layer may further include a hole blocking layer, an electron blocking layer, an emission-auxiliary layer 151, a buffer layer 141 and so on, and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as materials of the hole injection layer 130, the hole transport layer 140, the electron transport layer 160, the electron injection layer 170, the light emitting layer 150, a capping layer, an emission-auxiliary layer and so on. For example, the inventive compound may be used as materials of a hole transport layer 140 and/or an emission-auxiliary layer (151).

Meanwhile, since depending on the type of a substituent and position to which a substituent is attached, a band gap, electrical properties, interfacial properties, and the like may vary even in the same core, it is very important what the types of core and a combination of core and substituent attached to the core. Specially, long life span and high efficiency can be simultaneously achieved when an optimal combination of energy levels and T1 values, inherent material properties (mobility, interfacial properties, etc.), and the like among the respective layers of the organic material layer is given.

As already described above, in order to solve the emission problem with a hole transport layer in a conventional organic electric element, an emission-auxiliary layer is preferably formed between the hole transport layer and a light emitting layer, and it is necessary to form different emission-auxiliary layers corresponding to respective light emitting layers (R, G, B). Meanwhile, even when a similar core is used, it is very difficult to infer the characteristics of an emission-auxiliary layer if a used organic material layer varies because the correlation between the emission-auxiliary layer and a hole transport layer and between the emission-auxiliary layer and a light emitting layer (host) must be figured out.

Accordingly, in the present invention, energy levels, T1 values and inherent material properties (mobility, interfacial properties, etc.) among the respective organic material layers are optimized by forming a hole transport layer or/and an emission-auxiliary layer employing the inventive compounds, and thus the life span and efficiency of the organic electric element can be improved at the same time.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emission-auxiliary layer 151 may be further formed between a hole transport layer 140 and a light emitting layer 150.

Further, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer process. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

In accordance with an aspect of the present invention, there is provided an organic electric element comprising a first electrode, a second electrode, and an organic material layer which is formed between the first electrode and the second electrode and comprises at least an emission-auxiliary layer and a light emitting layer, wherein the emission-auxiliary layer comprises compound represented by the following Formula 1.

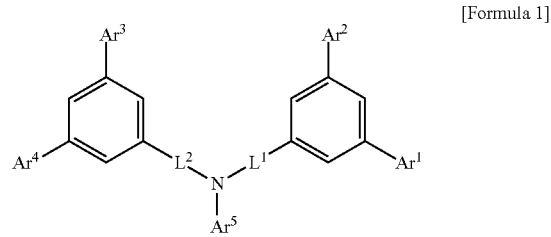

[Formula 1]

In Formula 1, each symbol may be defined as follows.

In the Formula 1, $Ar^1$ to $Ar^5$ may be each independently selected from the group consisting of a $C_6$-$C_{24}$ aryl group; a fluorenyl group; a $C_2$-$C_{25}$ heterocyclic group containing at least one heteroatom selected from the group consisting of O, N, S, Si, and P; a fused ring formed by a $C_3$-$C_{24}$ aliphatic ring and a $C_6$-$C_{24}$ aromatic ring; a $C_1$-$C_{20}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group and the combination thereof.

Preferably, $Ar^1$ to $Ar^4$ may be each independently a $C_6$-$C_{12}$ aryl group, a fluorenyl group, or a $C_3$-$C_{12}$ heterocyclic group, more preferably, a $C_6$-$C_{10}$ aryl group or a $C_{12}$ heterocyclic group, for example, phenyl, naphthyl, dibenzothiophene, dibenzofuran or a fluorenyl group and so on, and each of these may be further substituted with methyl or t-butyl.

Preferably, $Ar^5$ may be a $C_6$-$C_{18}$ aryl group or a $C_3$-$C_{12}$ heterocyclic group, more preferably, a $C_6$-$C_{12}$ aryl group or a $C_5$-$C_{12}$ heterocyclic group, more preferably, a $C_6$, $C_{10}$, $C_{12}$ or $C_{18}$ aryl group or, a $C_{12}$ heterocyclic group, for example, phenyl, naphthyl, biphenyl, terphenyl, dibenzothiophene and so on, and each of these may be further substituted with naphthyl or dibenzothiophene.

Preferably, $Ar^1$ to $Ar^5$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

$L^1$ and $L^2$ may be independently selected from the group consisting of a single bond, a $C_6$-$C_{24}$ arylene group, a fluorenylene group, a $C_2$-$C_{24}$ heterocyclic group containing at least one heteroatom selected from the group consisting of O, N, S, Si and P, a fused ring formed by a $C_3$-$C_{24}$ aliphatic ring and a $C_6$-$C_{24}$ aromatic ring and the combination thereof.

Preferably, $L^1$ and $L^2$ may be independently a $C_6$-$C_{12}$ arylene group or a $C_3$-$C_{12}$ heterocyclic group and so on, more preferably, a $C_6$ arylene group, or a $C_5$ or $C_{12}$ heterocyclic group, and for example, a single bond, phenyl, pyridine, dibenzothiophene and so on.

When $L^1$ and $L^2$ are each independently an arylene group, a fluorenylene group, a heterocyclic group or a fused ring, each of $L^1$ and $L^2$ may be further substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

Specifically, the compound of the emission-auxiliary layer represented by Formula 1 may be represented by any one of the following Formulas 2 to 6.

<Formula 2>

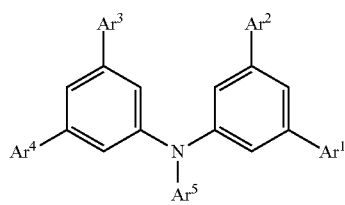

<Formula 3>

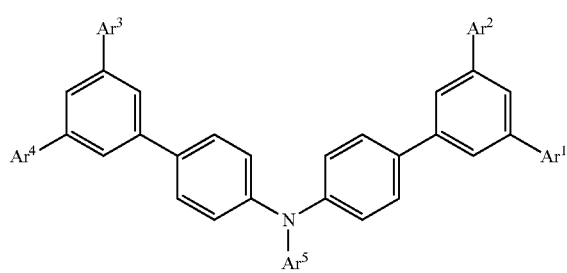

<Formula 4>

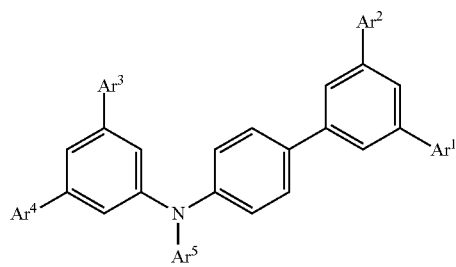

<Formula 5>

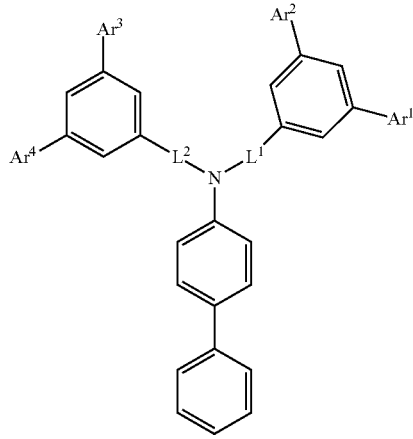

<Formula 6>

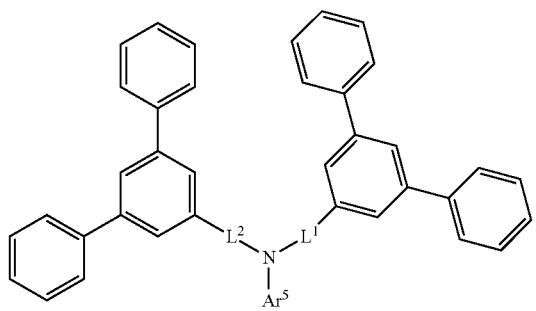

In formulas 2 to 6, $Ar^1$ to $Ar^5$, $L^1$ and $L^2$ may be each the same as defined in Formula 1 above.

More specifically, the compound represented by Formula 1 may be any one of the following compounds.

P-1

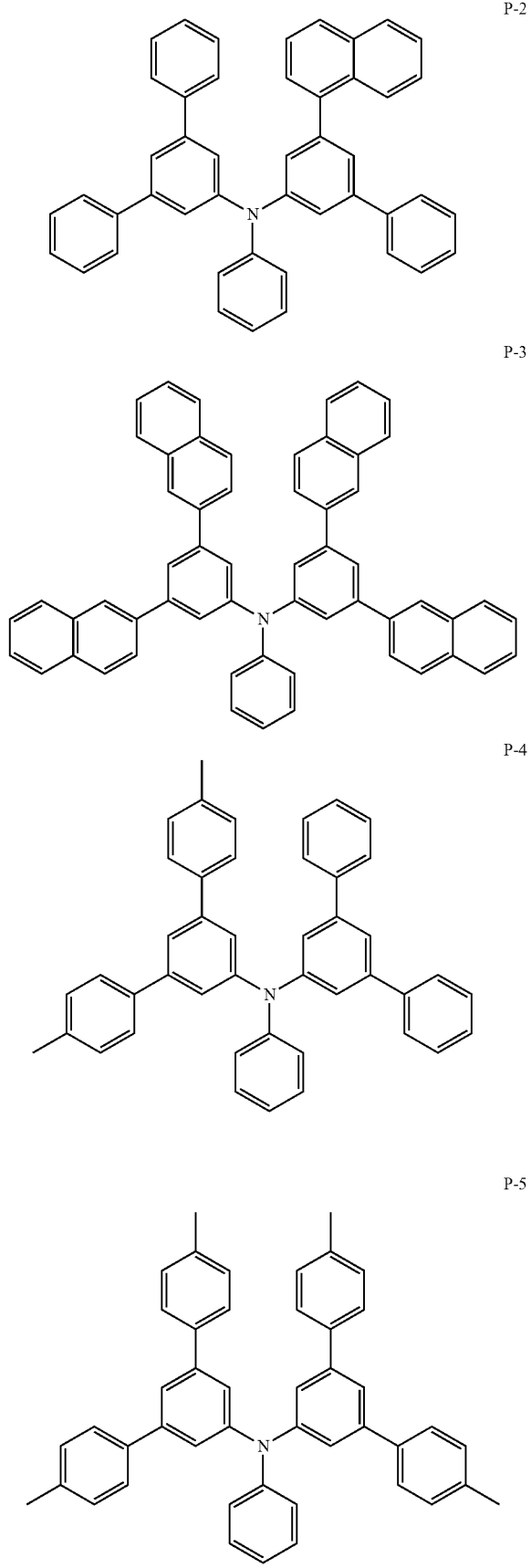
P-2
P-3
P-4
P-5
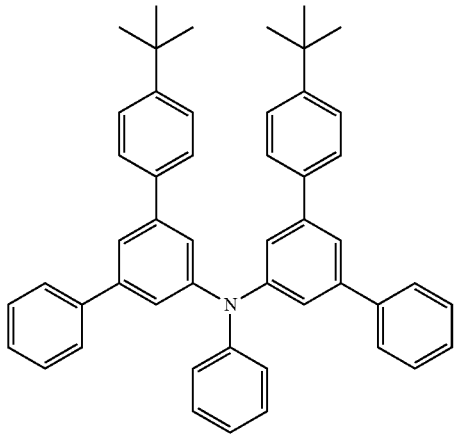
P-6
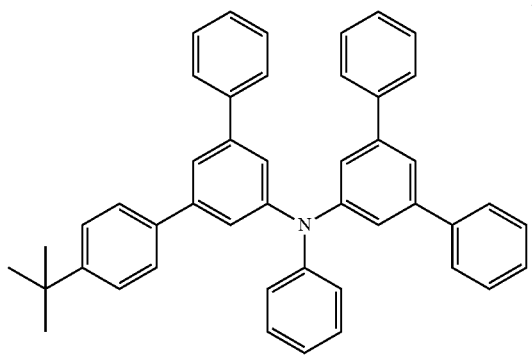
P-7
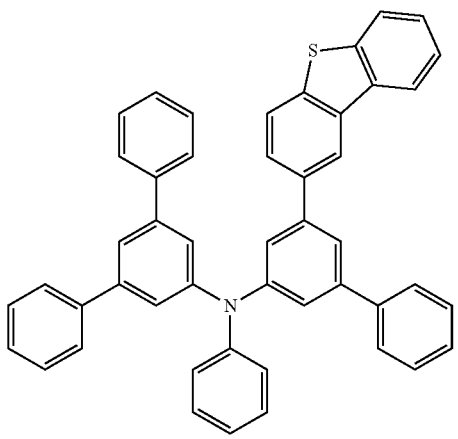
P-8

P-9
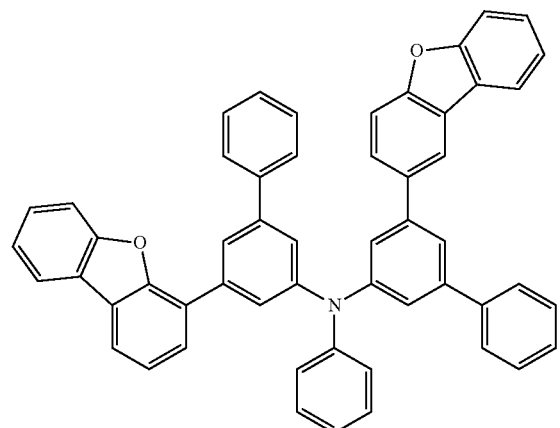
P-10
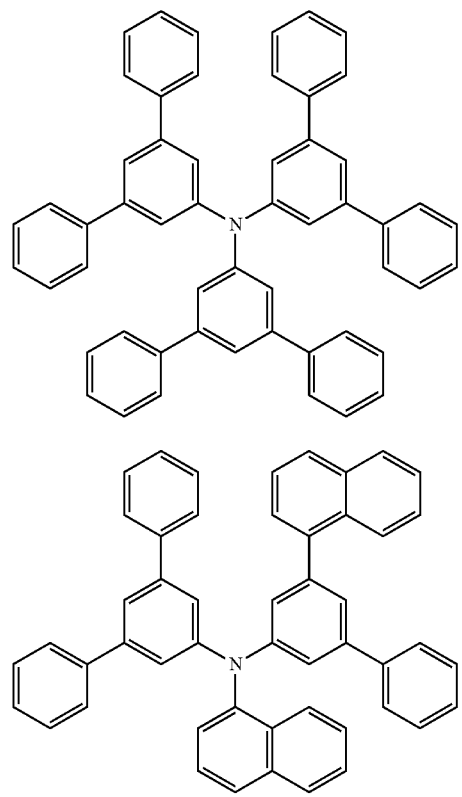
P-11
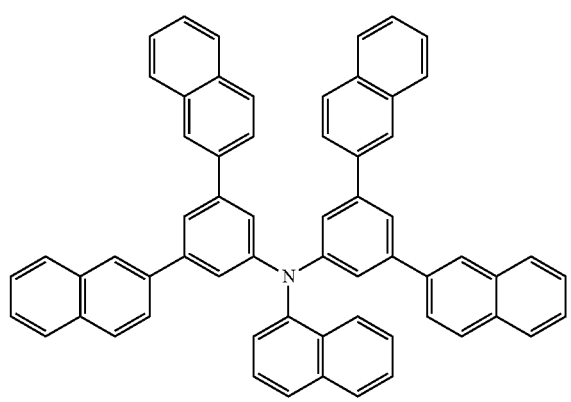
P-13
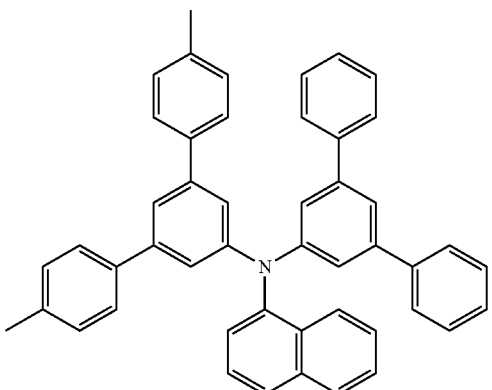
P-14
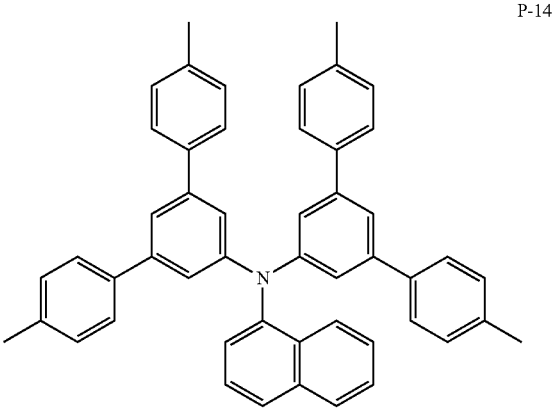
P-15
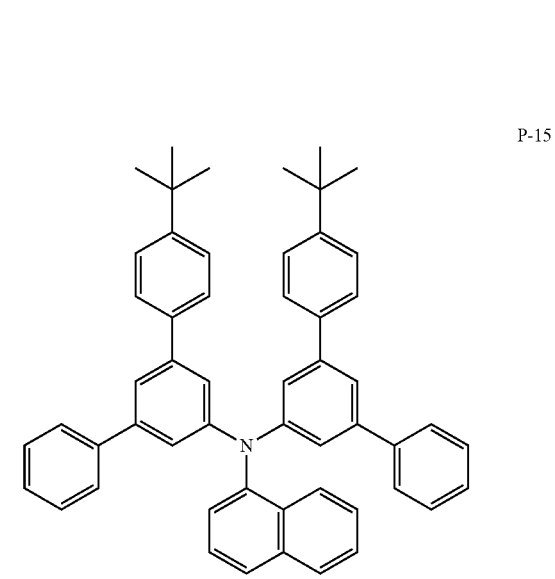
P-12

P-16
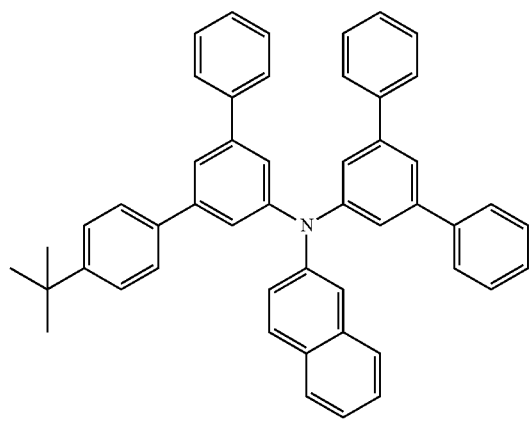
P-19
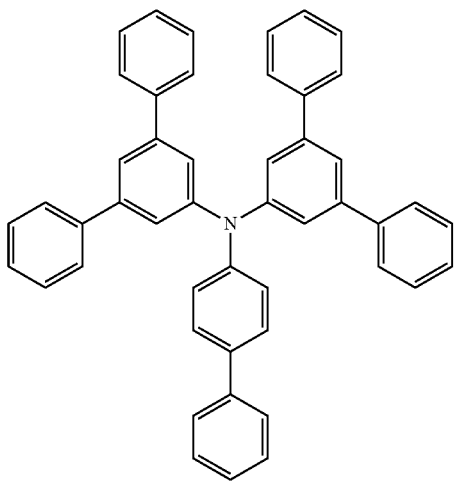
P-17
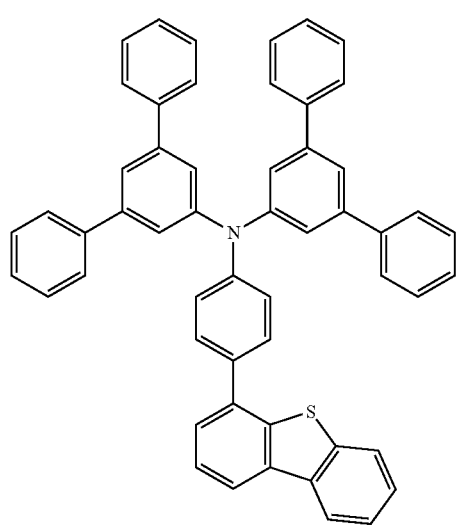
P-20
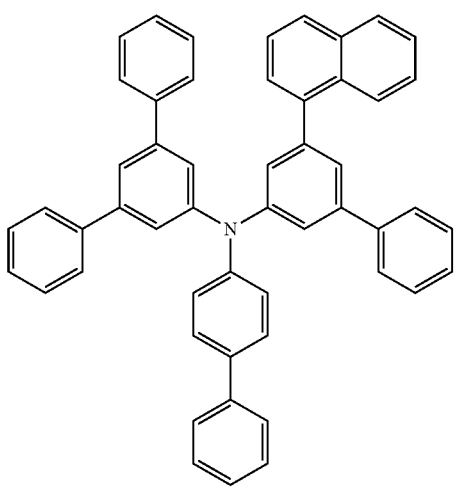
P-18
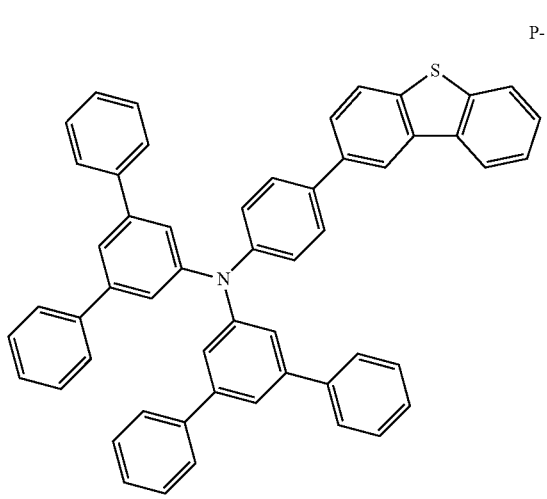
P-21
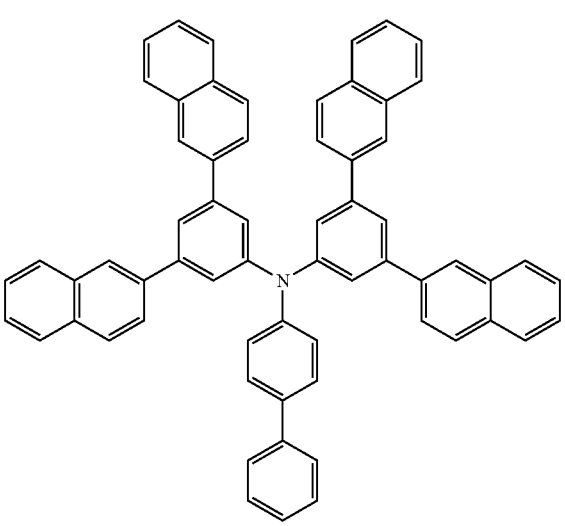

P-22
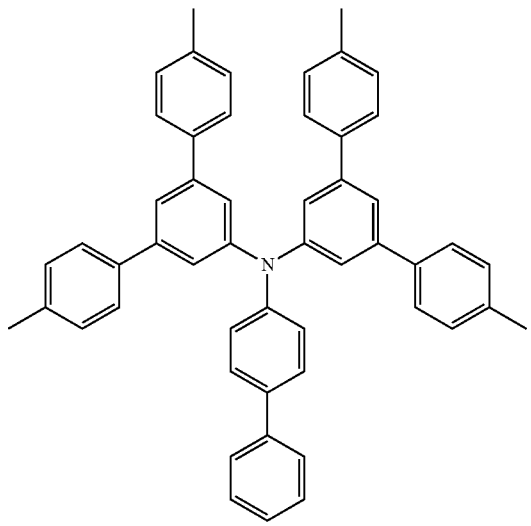
P-23
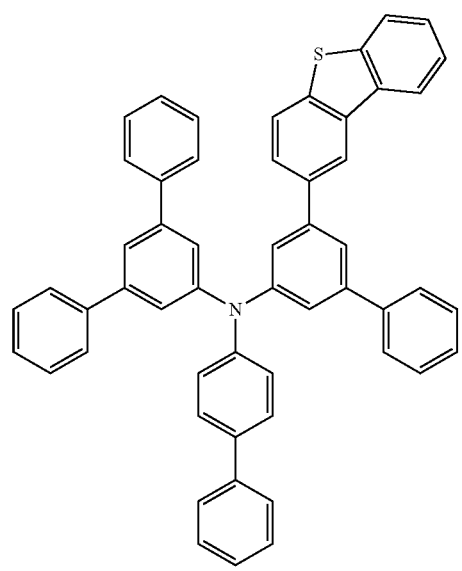
P-24
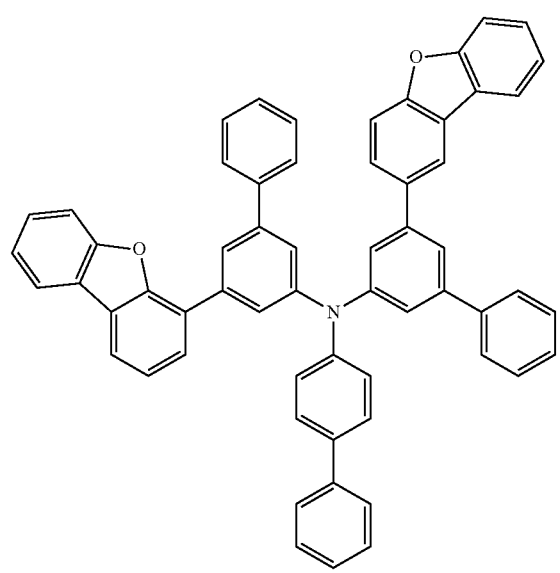
P-25
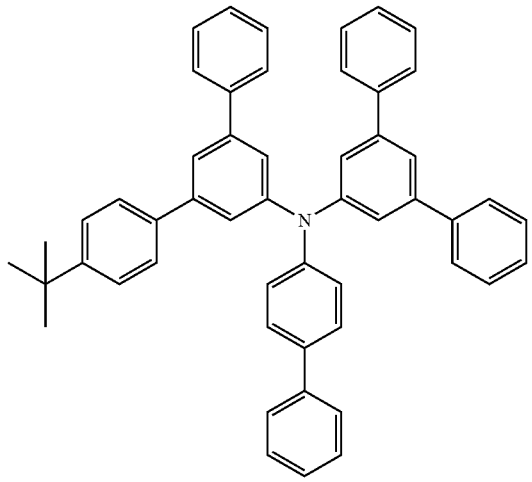
P-26
P-27

P-28
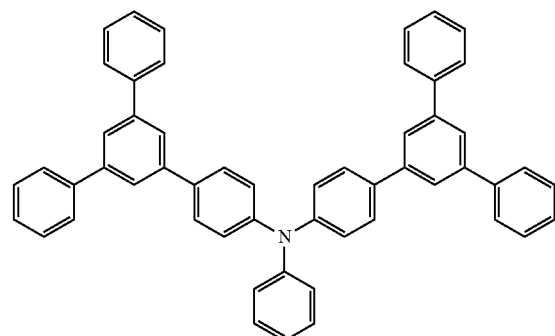
P-31
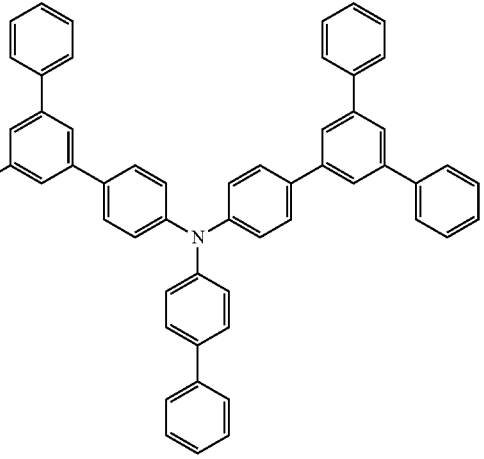
P-29
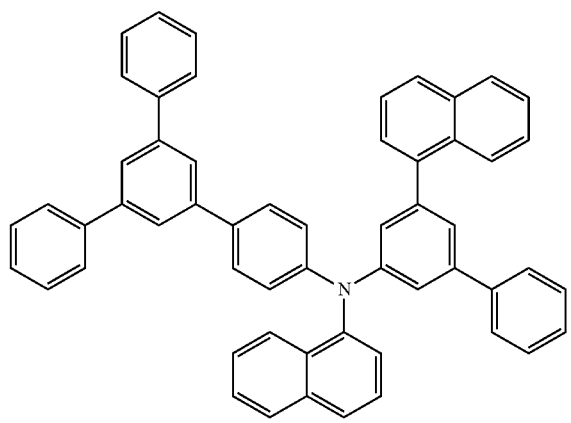
P-32
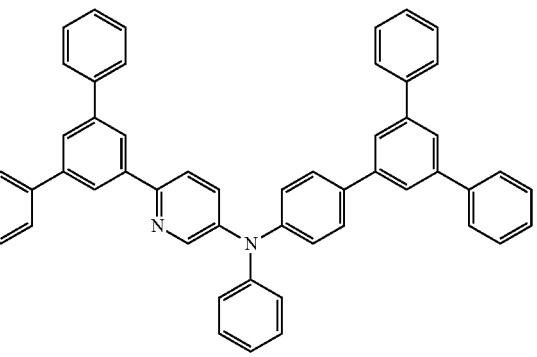
P-33
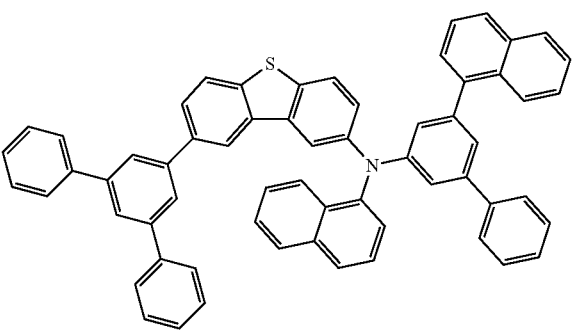
P-30
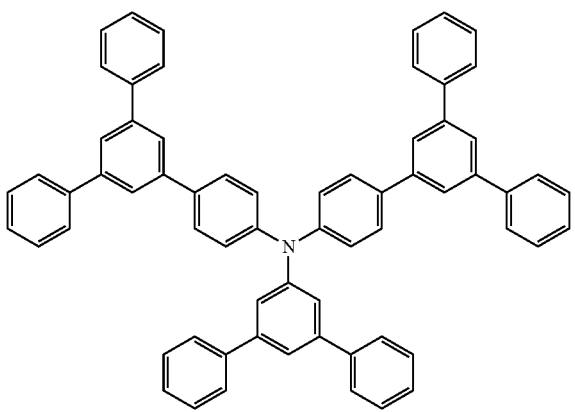
P-34
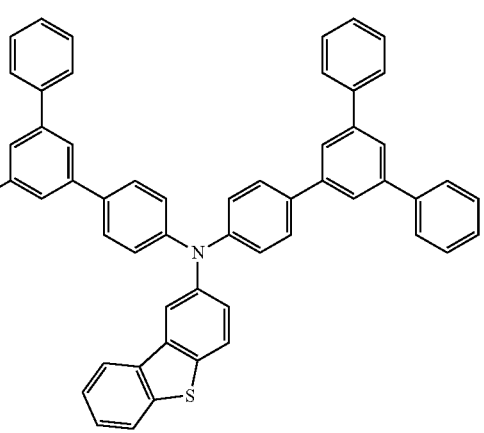

P-35

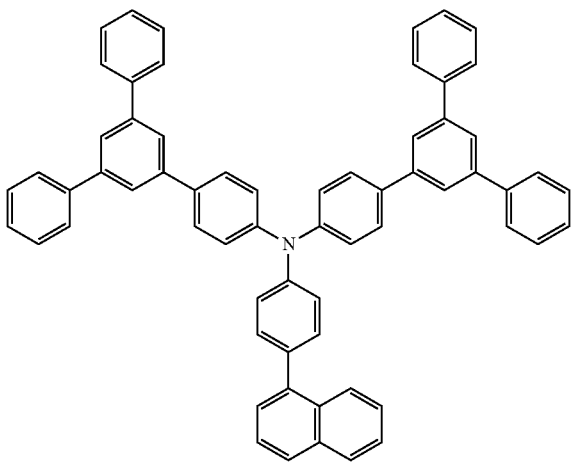

P-36

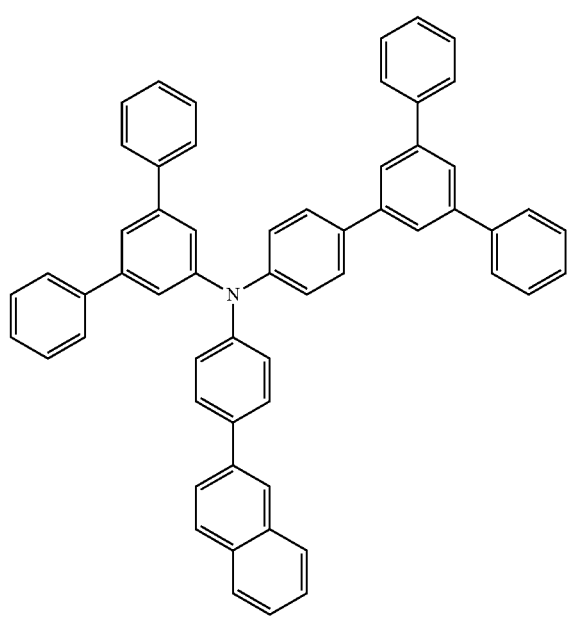

In another aspect of the present invention, there is provided an organic electric element comprising a first electrode, a second electrode, and an organic material layer formed between the first electrode and the second electrode, wherein the organic material layer comprises a hole transport layer, an emission-auxiliary layer and a light emitting layer and the emission-auxiliary comprises compound represented by Formula Formula 7 below.

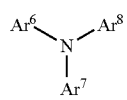

<Formula 7>

In Formula 7, each symbol may be defined as follows.

In the Formula 7, $Ar^6$ and $Ar^7$ may be independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group, -L'-N($R^a$) ($R^b$) and the combination thereof.

Preferably, $Ar^6$ and $Ar^7$ may be independently a $C_6$-$C_{18}$ aryl group, a fluorenyl group, a $C_3$-$C_{12}$ heterocyclic group or -L'-N($R^a$) ($R^b$) and so on, more preferably, a $C_6$, $C_{10}$ or $C_{12}$ aryl group or a $C_{12}$ heterocyclic group, for example, phenyl, naphthyl, biphenyl, fluorene, spirobifluorene, dibenzothiophene, dibenzofuran or diphenylamine and so on, and each of these may be further substituted with methyl, t-butyl, naphthyl, methoxy, phenyl, pyrimidine or fluorophenyl.

Preferably, $Ar^6$ and $Ar^7$ may be independently substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

Further, $Ar^6$ and $Ar^7$ may be linked together to form a ring.

Further, $Ar^8$ may be represented by any one of Formulas 7-a, 7-b and 7-c below:

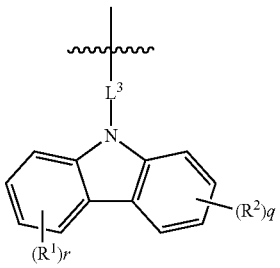

<Formula 7-a>

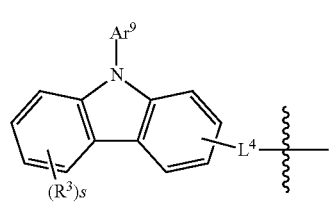

<Formula 7-b>

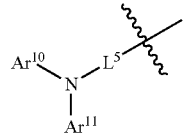

<Formula 7-c>

In Formulas 7-a, 7-b and 7-c, $R^1$ to $R^3$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, a $C_6$-$C_{30}$ aryloxy group, -L'-N($R^a$) ($R^b$) and the combination thereof. q, r and s are each an integer of 0 to 4, and when q, r and s are each an integer of 2 or more, each of plural $R^1$s, $R^2$s and $R^a$s may be same or different each other.

Preferably, $R^1$ to $R^3$ are each independently hydrogen, a $C_6$-$C_{12}$ aryl group or a $C_3$-$C_{12}$ heterocyclic group and so on, more preferably, $C_6$ aryl group or a $C_{12}$ heterocyclic group and so on, and for example, hydrogen, phenyl, carbazole substituted with phenyl and so on.

Preferably, $R^1$ to $R^3$ may be each independently substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

Further, adjacent groups among $R^1$s to $R^a$s may be linked together to form a ring, and the group of $R^1$ to $R^3$ not forming a ring is the same as defined in the above, wherein the formed ring may be a monocyclic or polycyclic ring.

$Ar^9$ to $Ar^{11}$ 은 may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group, -L'-N($R^a$) ($R^b$) and the combination thereof.

Preferably, $Ar^9$ to $Ar^{11}$ may be each independently a $C_6$-$C_{18}$ aryl group, a fluorenyl group or a $C_2$-$C_{12}$ heterocyclic group and so on, more preferably, a $C_6$, $C_{10}$ or $C_{12}$ aryl group, or a $C_{12}$ heterocyclic group, for example, phenyl, naphthyl, biphenyl, fluorene, spirobifluorene, dibenzothiophene, or dibenzofuran and so on, and each of these may be further substituted with methyl or phenyl.

Preferably, $Ar^9$ to $Ar^{11}$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group, $L^3$ and $L^5$ may be each independently selected from the group consisting of a $C_6$-$C_{60}$ arylene group, a fluorenylene group, a fused ring formed by a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si and P, and the combination thereof.

Preferably, $L^3$ and $L^5$ may be each independently a $C_6$-$C_{18}$ arylene group, a fluorenylene group, a $C_3$-$C_{12}$ heterocyclic group and so on, more preferably, a $C_{12}$ arylene group, for example, biphenyl, fluorine and so on, and each of these may be further substituted with methyl.

$L^4$ may be selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si and P, and the combination thereof.

Preferably, $L^4$ may be a $C_6$-$C_{18}$ arylene group or a $C_3$-$C_{12}$ heterocyclic group and so on, more preferably, a $C_6$ or $C_{12}$ arylene group, and for example, phenyl, biphenyl and so on.

Preferably, when $L^3$ to $L^5$ are each an arylene group, a fluorenylene group, a heterocyclic group or a fused ring, each of $L^3$ to $L^5$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

Specifically, the compound of a hole transport layer represented by Formula 7 may be represented by any one of the following compounds.

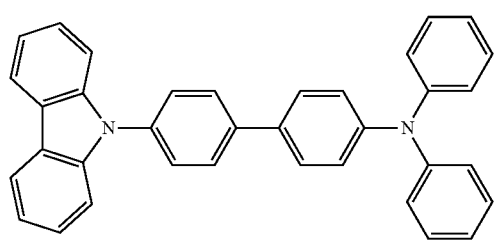

1-1

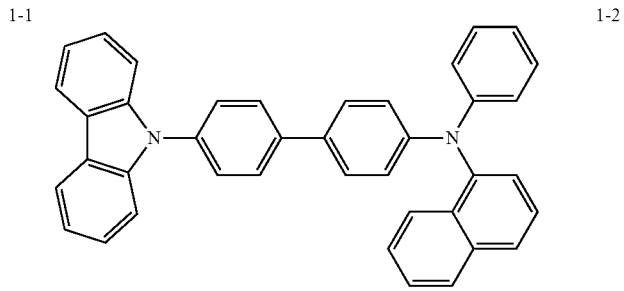

1-2

-continued
1-3
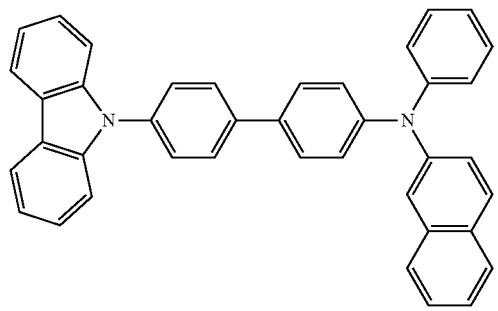
1-4
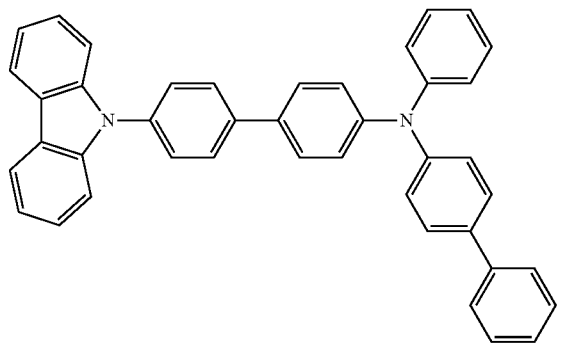
1-5
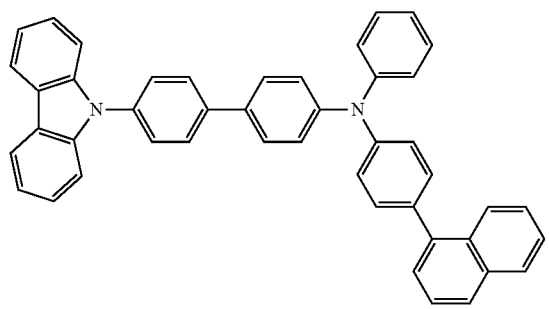
1-6
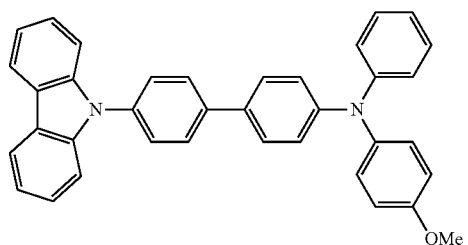
1-7
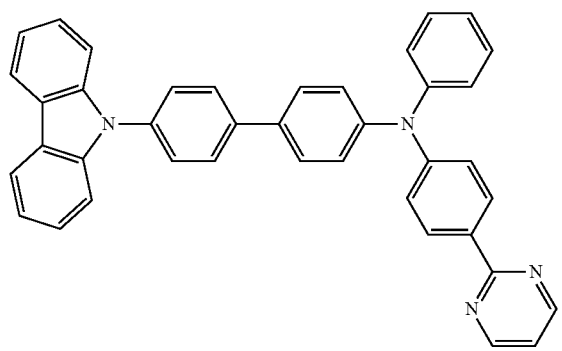
1-8
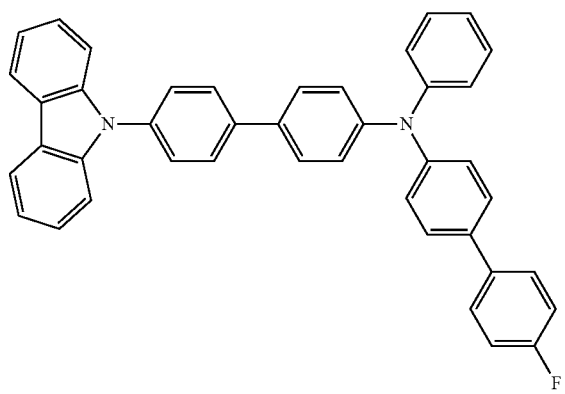
1-9
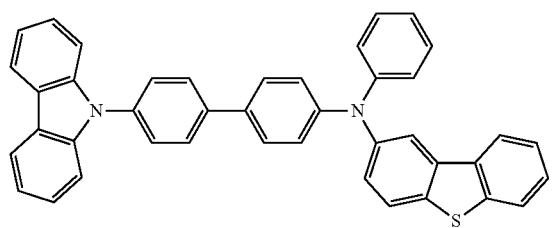
1-10
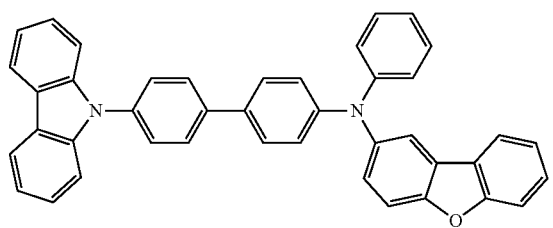

-continued
1-11
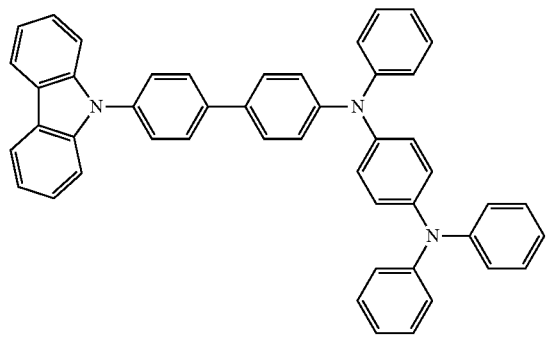
1-12
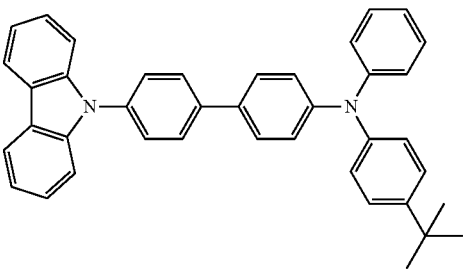
1-13
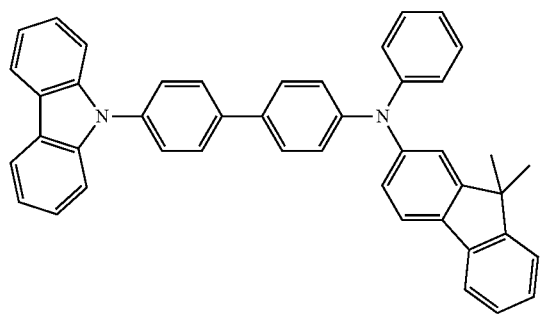
1-14
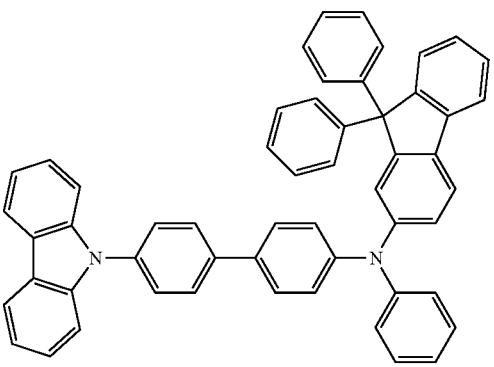
1-15
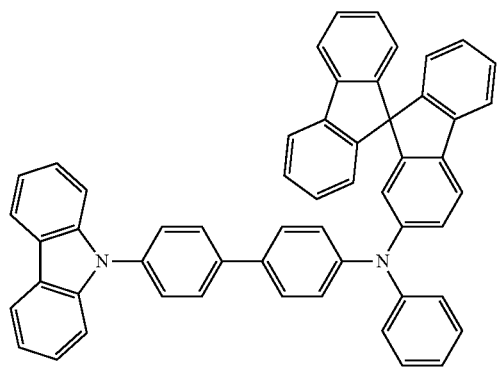
1-16
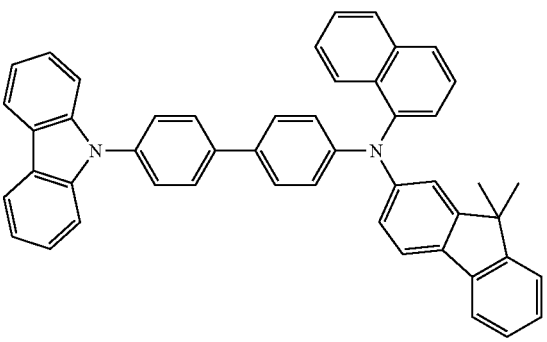
1-17
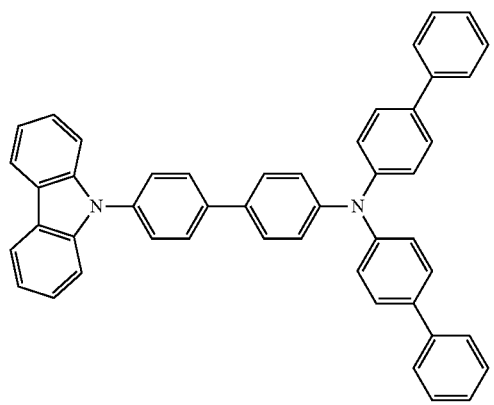
1-18
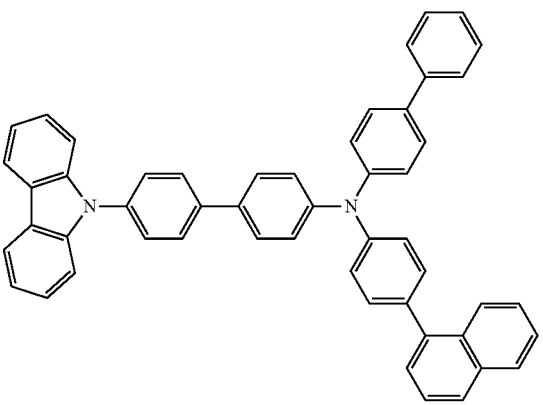

-continued
1-19
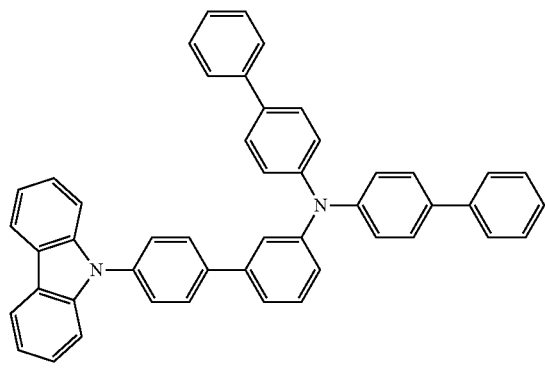
1-20
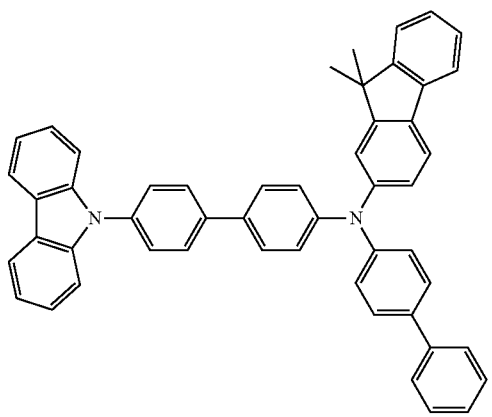
1-21
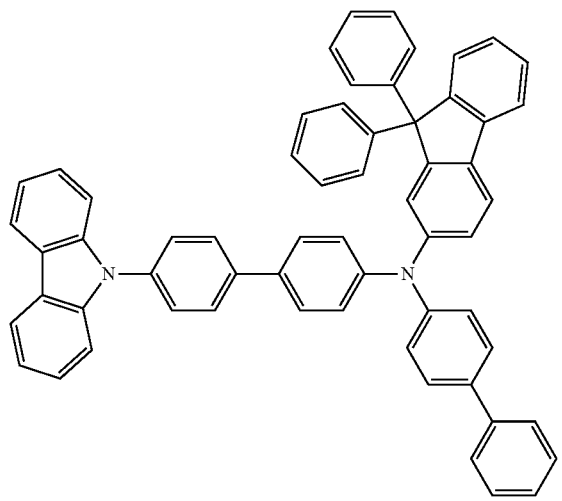
1-22
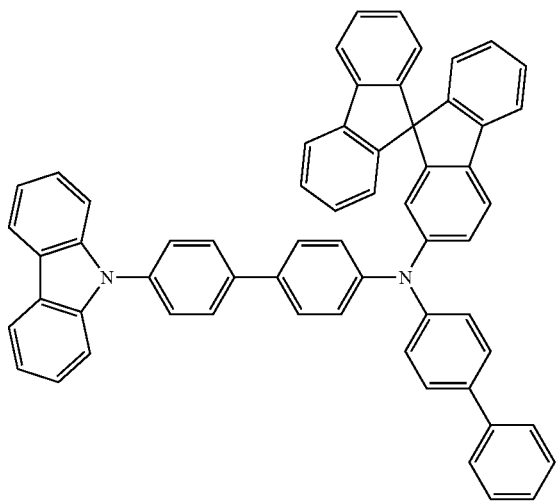
1-23
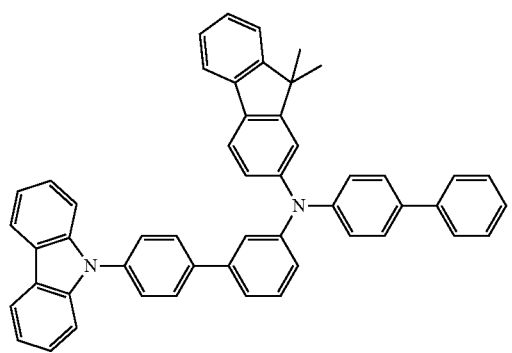
1-24
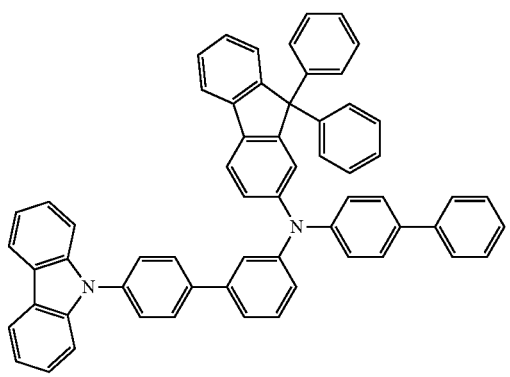

-continued
1-25
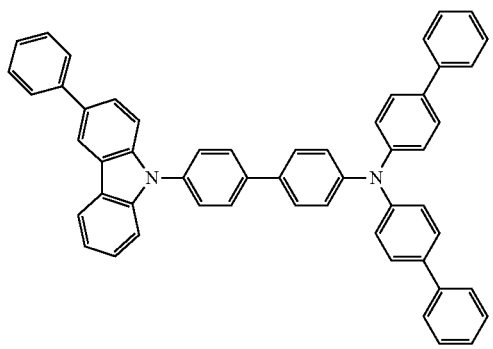
1-26
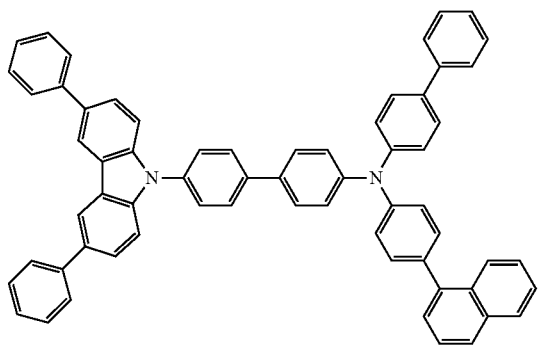
1-27
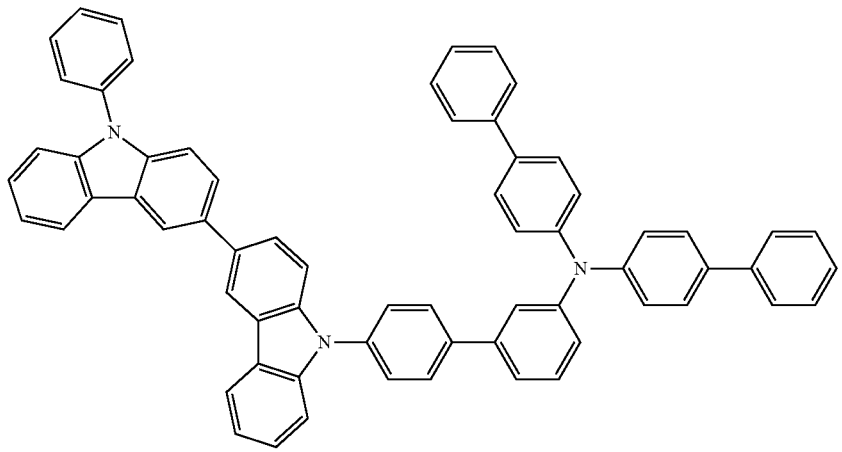
1-28
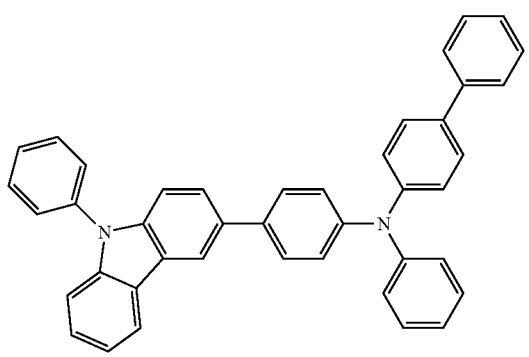
1-29
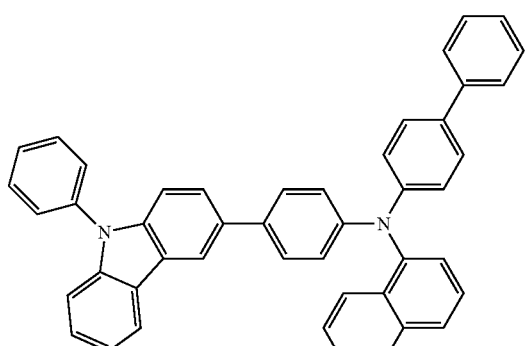
1-30
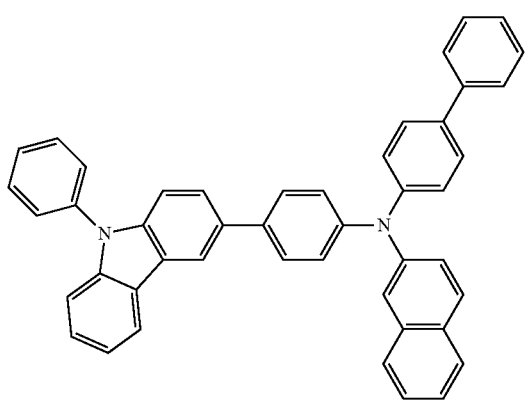
1-31
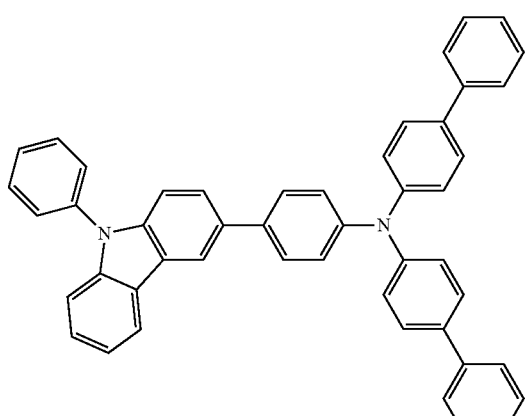

1-32
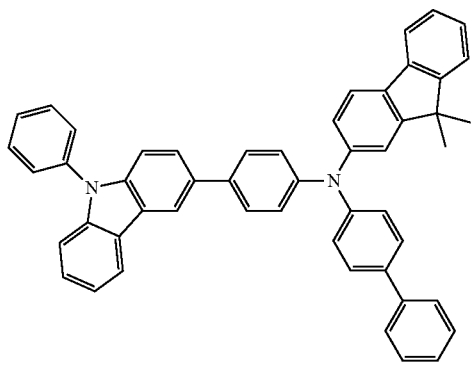
1-33
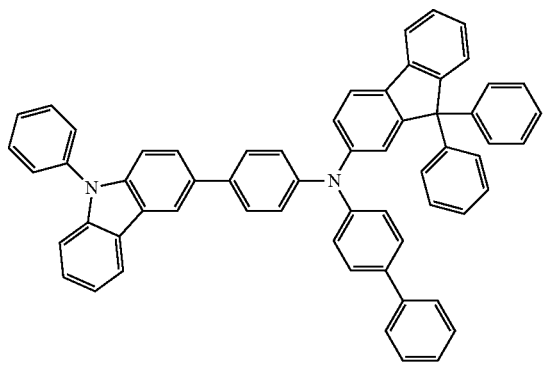
1-34
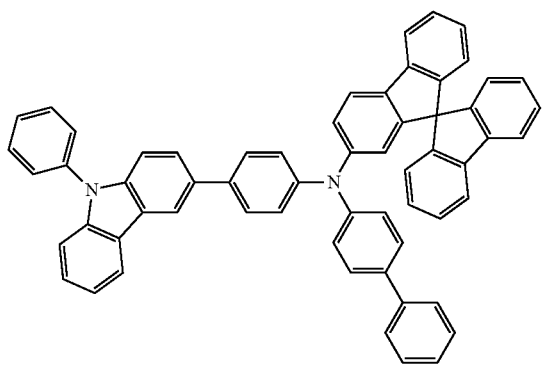
1-35
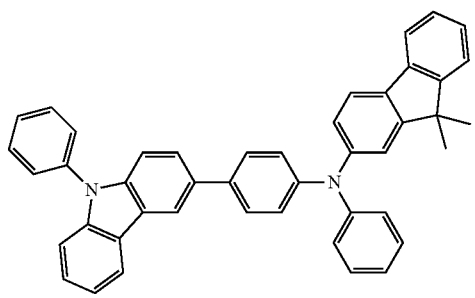
1-36
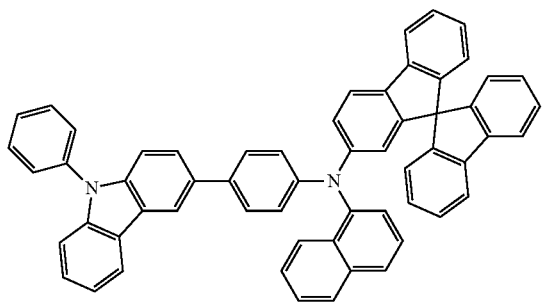
1-37
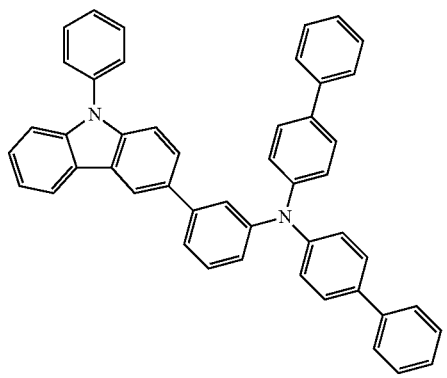
1-38
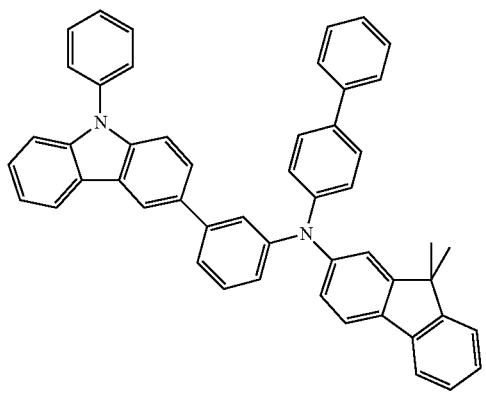
1-39
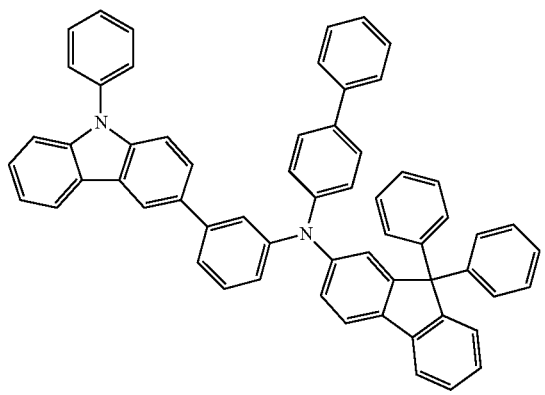

-continued
1-40
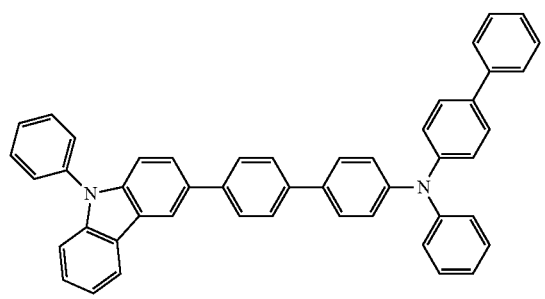
1-41
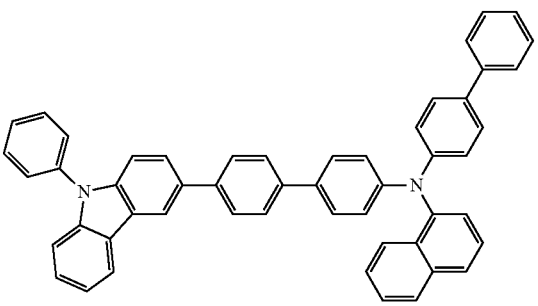
1-42
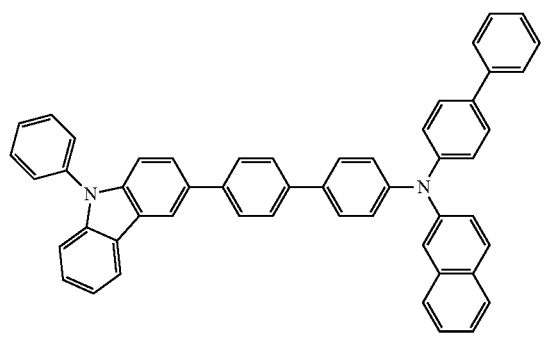
1-43
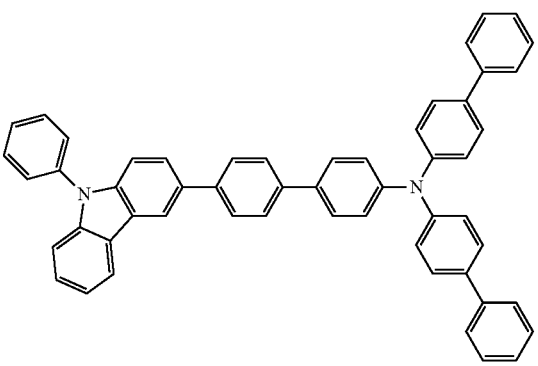
1-44
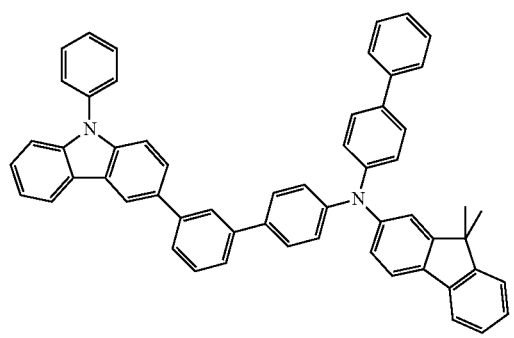
1-45
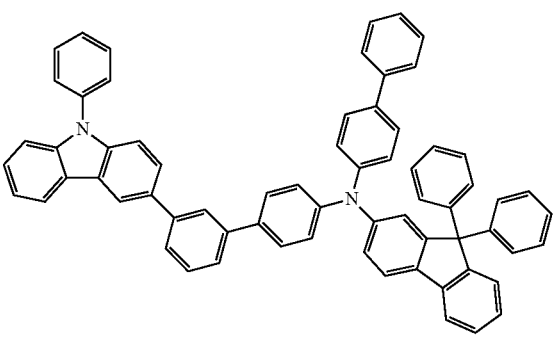
1-46
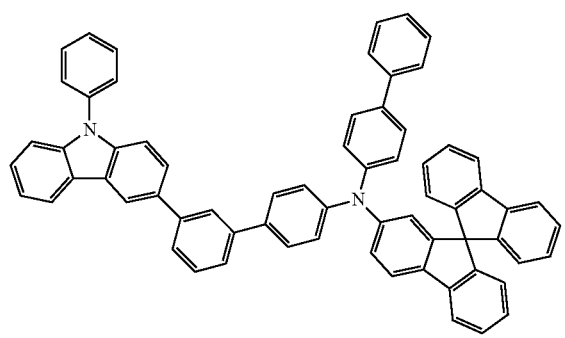
1-47
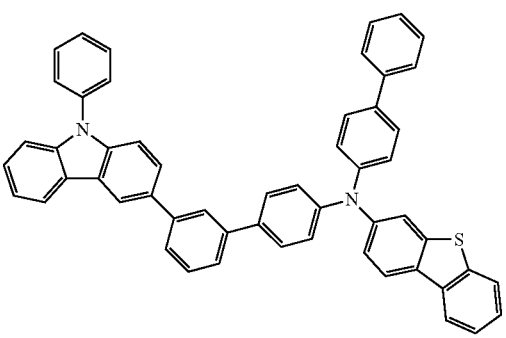

-continued
1-48
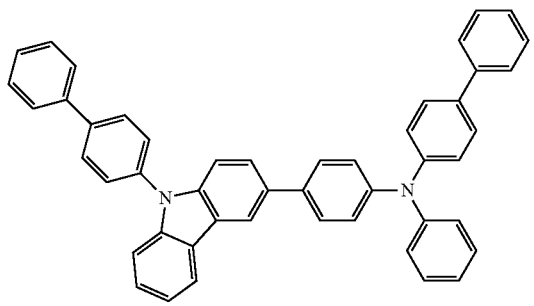
1-49
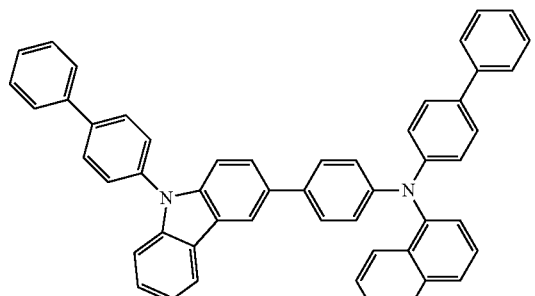
1-50
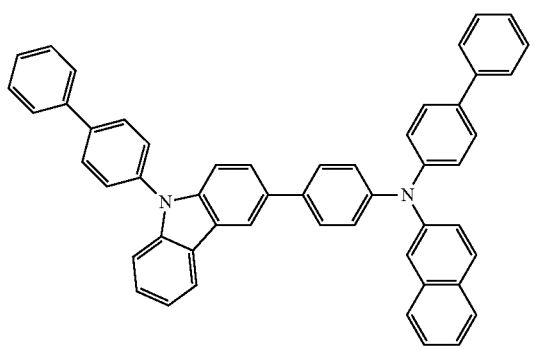
1-51
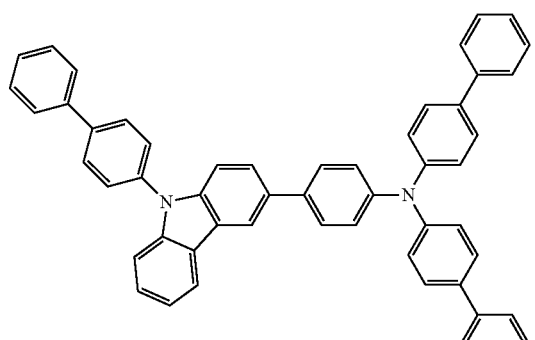
1-52
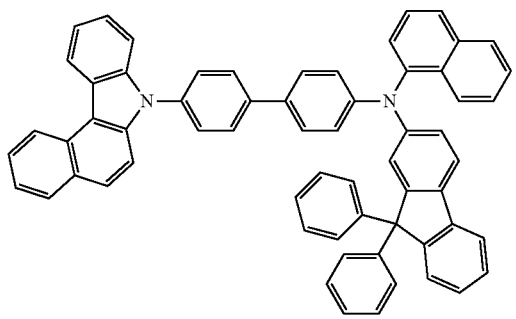
1-53
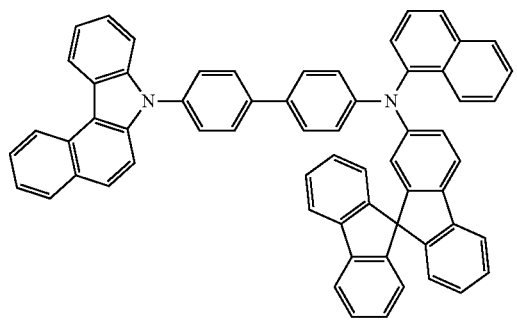
1-54
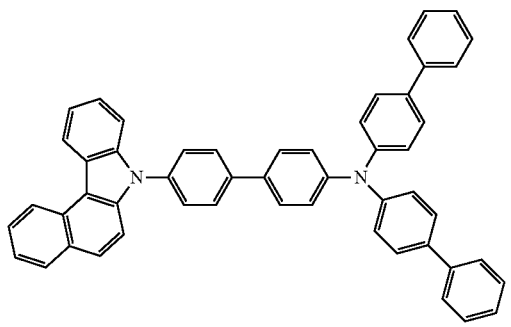
1-55
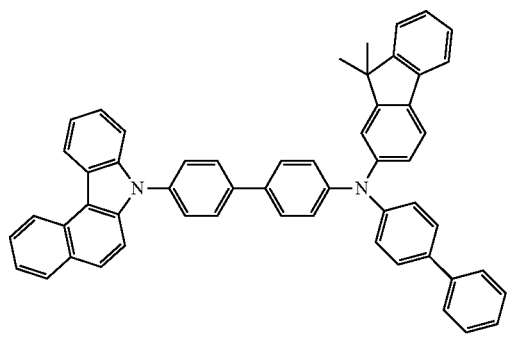

-continued
1-56
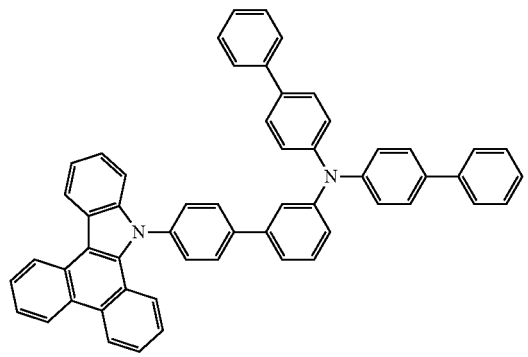
1-57
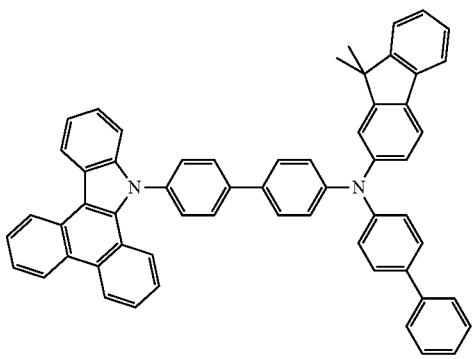
1-58
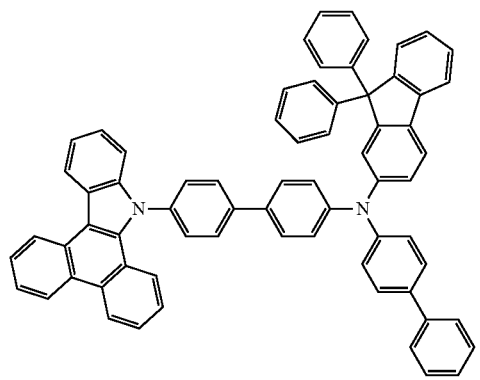
1-59
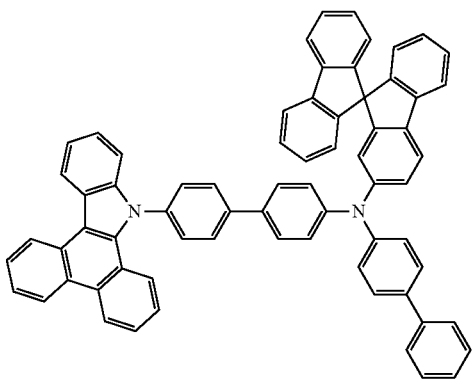
1-60
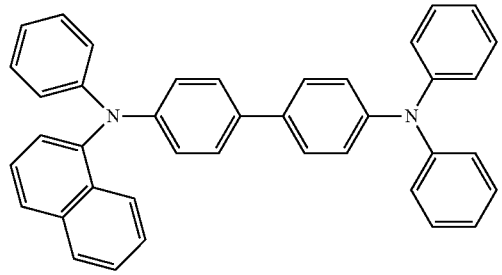
1-61
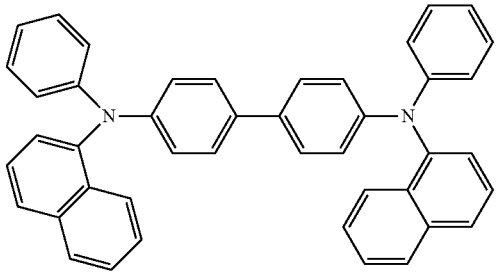
1-62
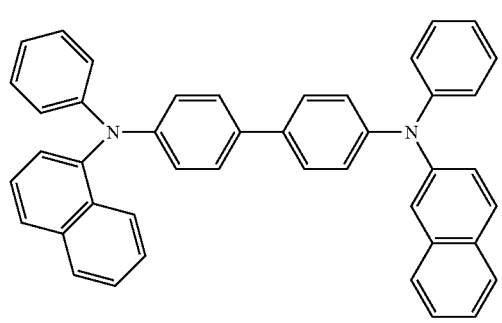
1-63
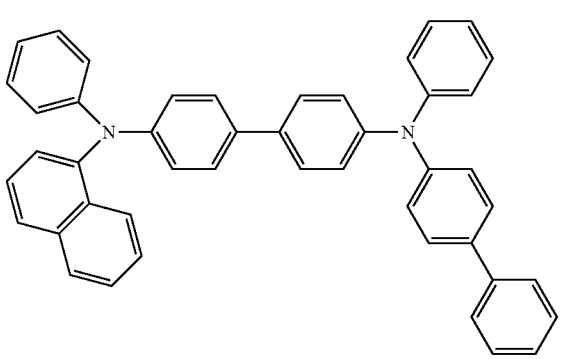

1-64
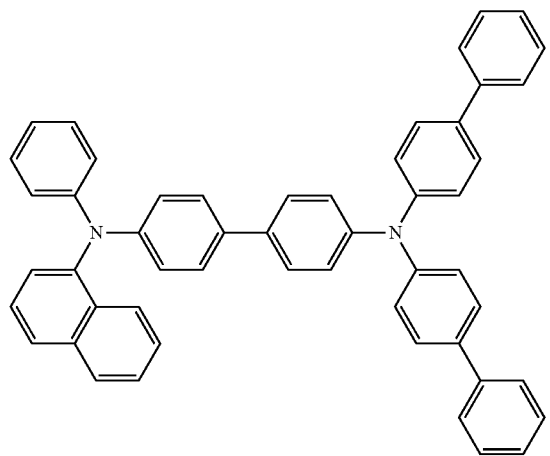
1-65
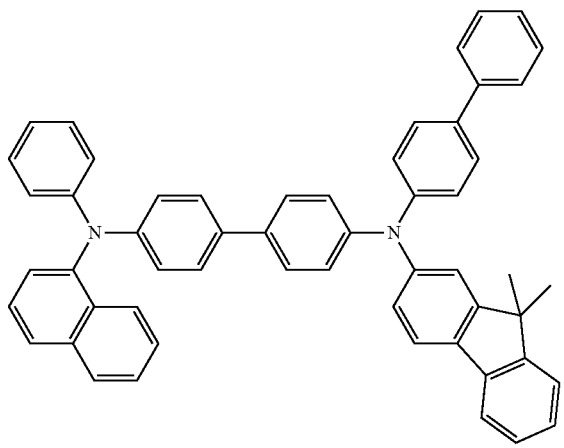
1-66
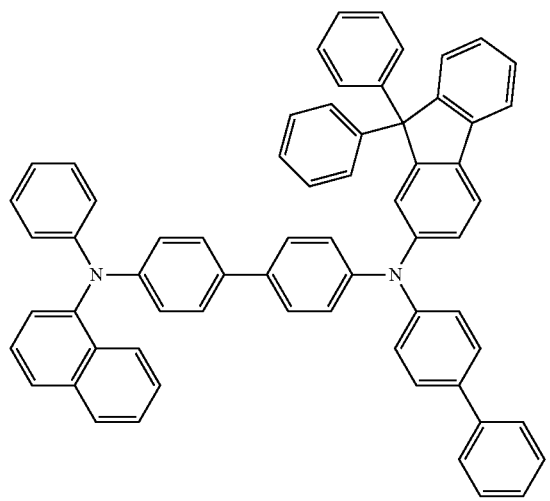
1-67
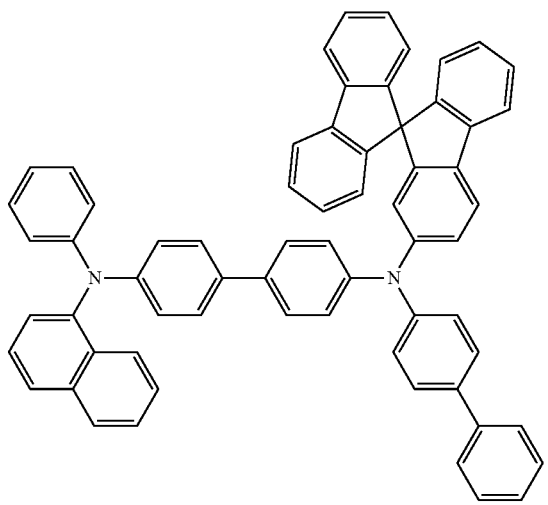
1-68
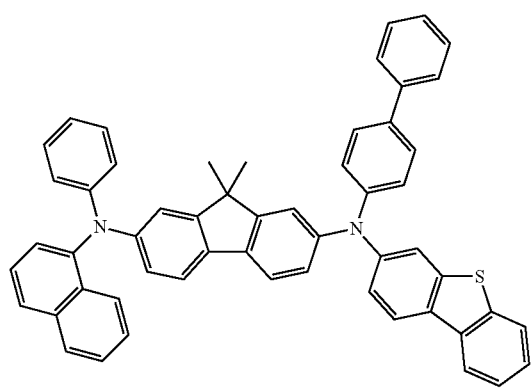
1-69
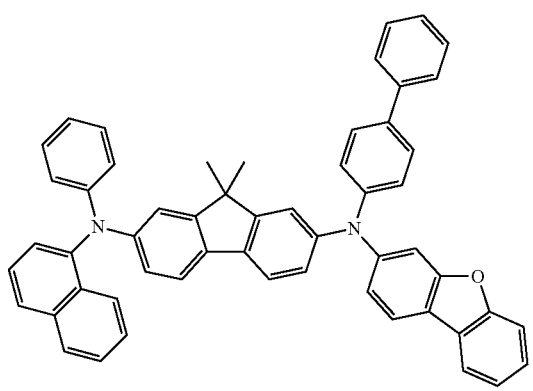

-continued 1-70

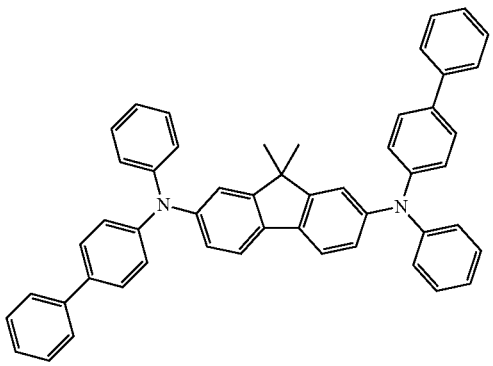

1-71

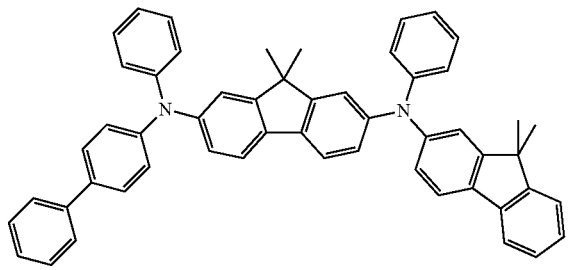

In another aspect of the present invention, compound included in the emission-auxiliary layer of the present invention may be the same kind or a mixture of two or more different kinds represented by Formula 1. For example, the emission-auxiliary layer may be formed as same kind of compound P-1 among compounds, or as mixture of compounds P-1 and P-2.

In another aspect of the present invention, the present invention provides an organic electric element further including a layer to improve luminescent efficiency which is formed on at least one of the sides the first or second electrodes, which is opposite to the organic material layer.

Hereinafter, synthesis method of the inventive compound according to one embodiment of the present invention and Preparation method of an organic electric element will be described in detail by way of example. However, the following examples are only for illustrative purposes and are not intended to limit the scope of the present invention.

SYNTHESIS EXAMPLE

I. Synthesis Example of Compounds Represented by Formula 1

The compounds (final products) of the present invention represented by Formula 1 can be synthesized by reaction of Sub 1 and Sub 2 as illustrated in, but not limited to, the following Reaction Scheme 1.

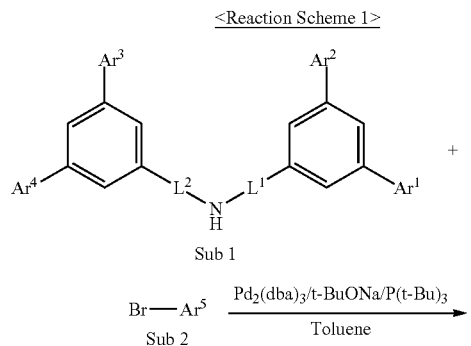

-continued

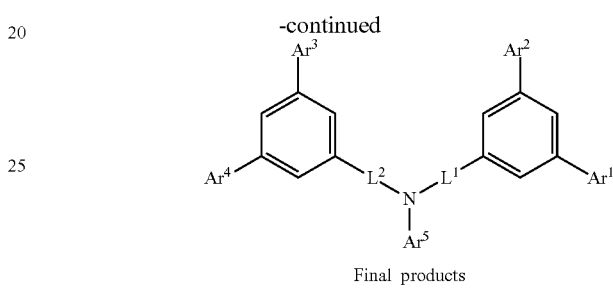

Final products

1. Synthesis Example of Compound Sub 1

Compound Sub 1 of the above Reaction Scheme 1 can be synthesized, but not limited to, by the following Reaction Scheme 2.

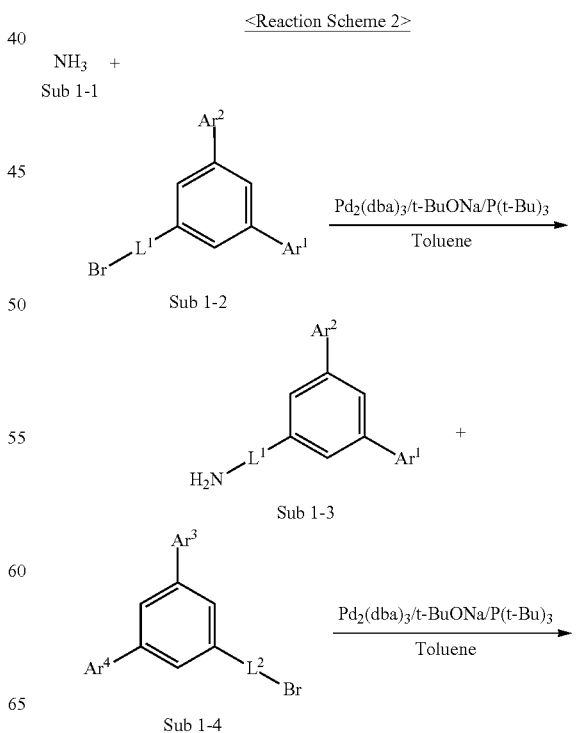

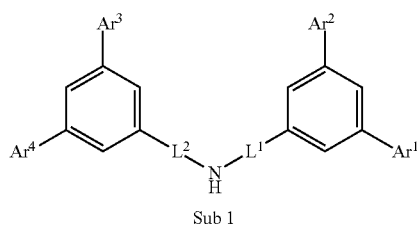

Sub 1

Synthesis Examples of compounds comprised in Sub 1 are as followings.

(1) Synthesis Example of Compound Sub 1(1)

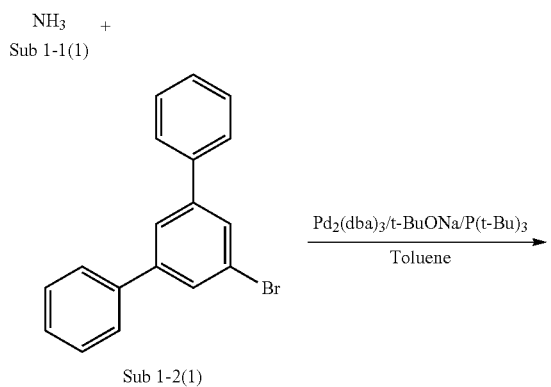

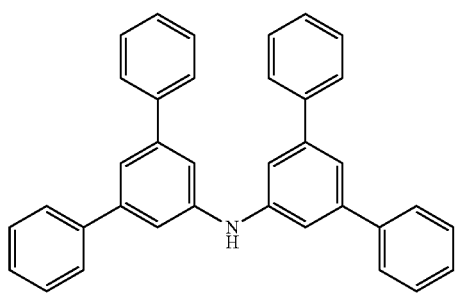

Sub 1(1)

1) Synthesis of Compound Sub 1-3(1)

Sub 1-1(1) (0.3 g, 20 mmol), Sub 1-2(1) (6.2 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with CH$_2$Cl$_2$ and water. The organic layer was dried with MgSO$_4$ and concentrated. The concentrate was separated by silica gel column chromatography and recrystallization, whereby compound Sub 1-3(1) was obtained in the amount of 3.7 g in 76% yield.

2) Synthesis of Compound Sub 1(1)

Sub 1-3(1) (3.7 g, 15.7 mmol), Sub 1-4(1) (4.7 g, 15.7 mmol), Pd$_2$(dba)$_3$ (0.5 g, 0.5 mmol), P(t-Bu)$_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with CH$_2$Cl$_2$ and water. The organic layer was dried with MgSO$_4$ and concentrated. The concentrate was separated by silica gel column chromatography and recrystallization, whereby compound Sub 1(1) was obtained in the amount of 5.6 g (yield: 78%).

(2) Synthesis Example of Compound Sub 1(11)

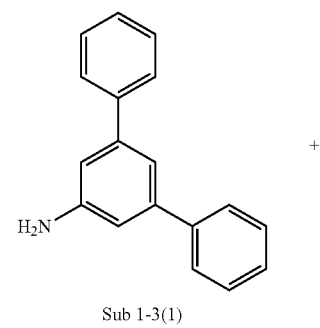

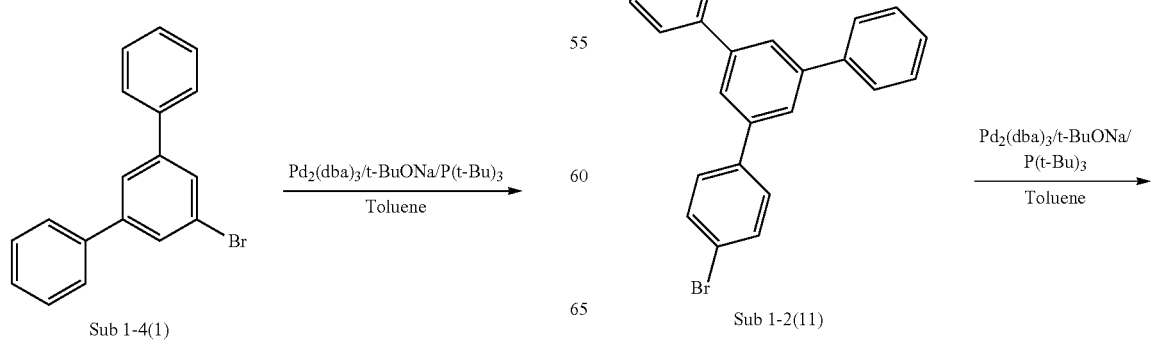

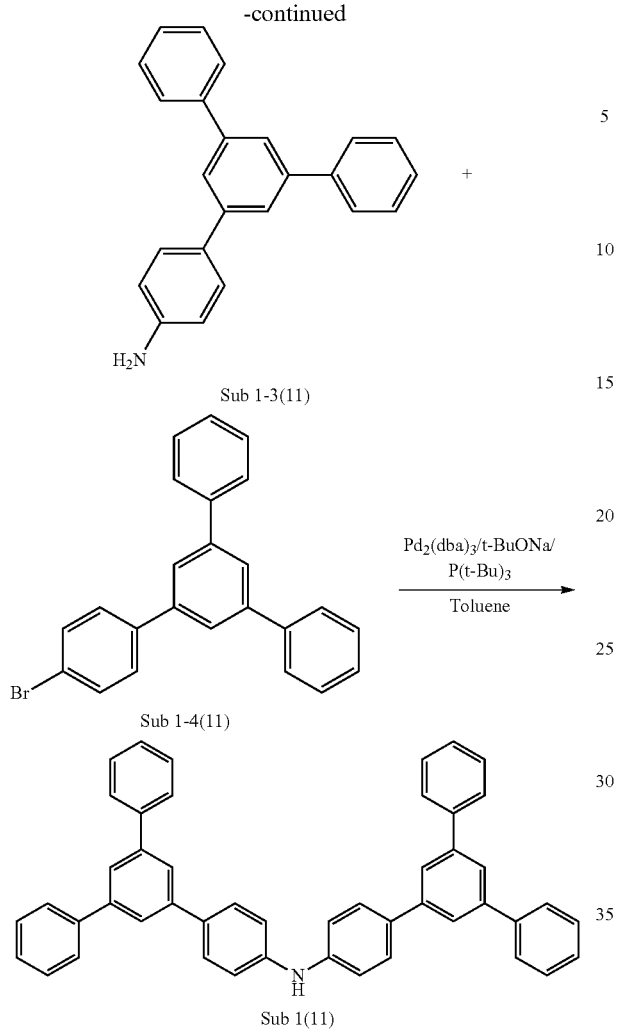

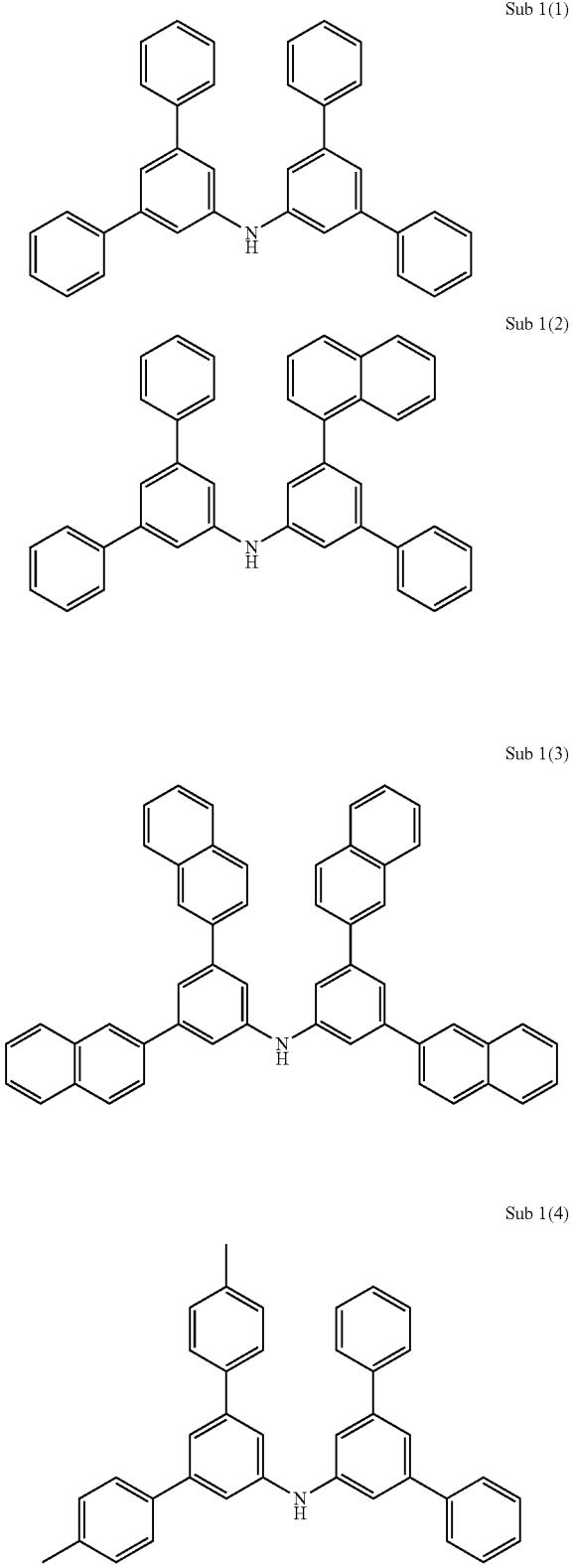

The compounds comprised in Sub 1 may be, but not limited to, the following compounds, and Table 1 below shows FD-MS (Field Desorption-Mass Spectrometry) data of the compounds.

1) Synthesis Example of Compound Sub 1-3(1)

Sub 1-1(1) (0.3 g, 20 mmol), Sub 1-2(11) (7.7 g, 20 mmol), $Pd_2(dba)_3$ (0.5 g, 0.6 mmol), $P(t-Bu)_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with $CH_2Cl_2$ and water. The organic layer was dried with $MgSO_4$ and concentrated. The concentrate was separated by silica gel column chromatography and recrystallization, whereby compound Sub 1-3(11) was obtained in the amount of 4.9 g (yield: 77%).

2) Synthesis Example of Compound Sub 1(11)

Sub 1-3(11) (4.9 g, 15.4 mmol), Sub 1-4(11) (5.9 g, 15.4 mmol), $Pd_2(dba)_3$ (0.5 g, 0.5 mmol), $P(t-Bu)_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with $CH_2Cl_2$ and water. The organic layer was dried with $MgSO_4$ and concentrated. The concentrate was separated by silica gel column chromatography and recrystallization, whereby compound Sub 1(11) was obtained in the amount of 7.7 g (yield: 80%).

Sub 1(5)
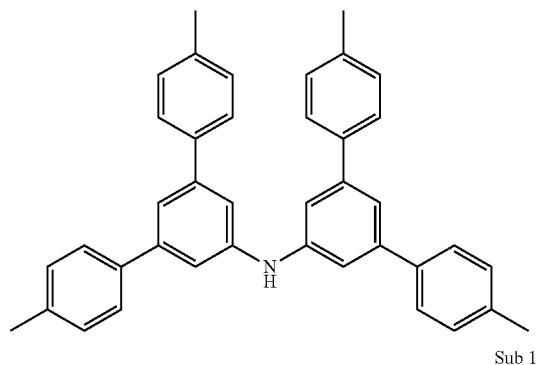
Sub 1(6)
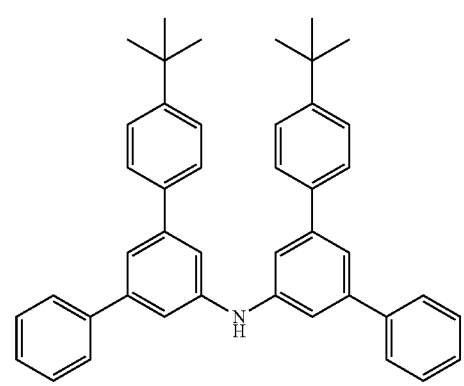
Sub 1(7)
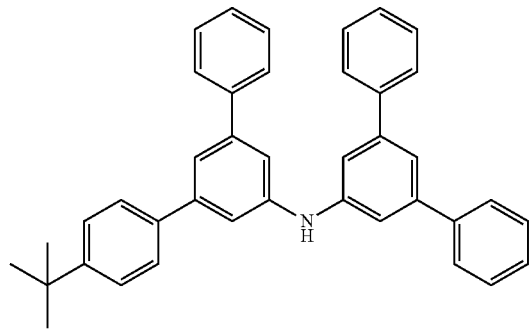
Sub 1(8)
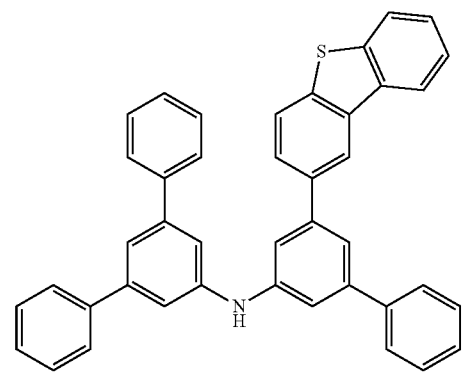
Sub 1(9)
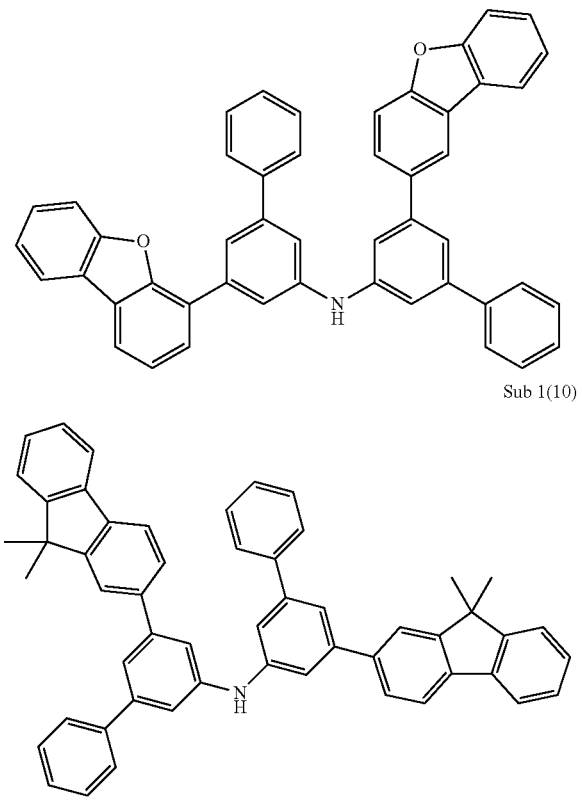
Sub 1(10)
Sub 1(11)
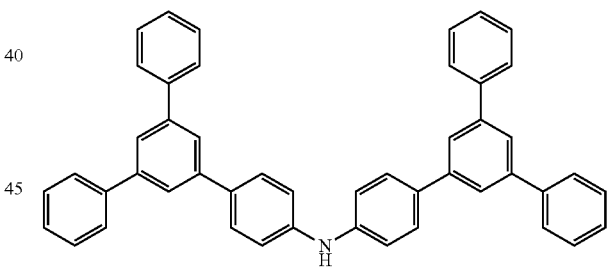
Sub 1(12)
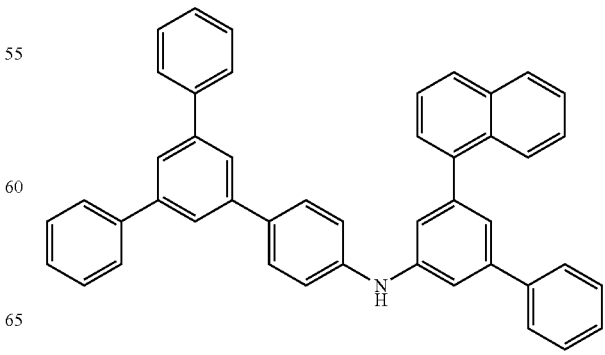

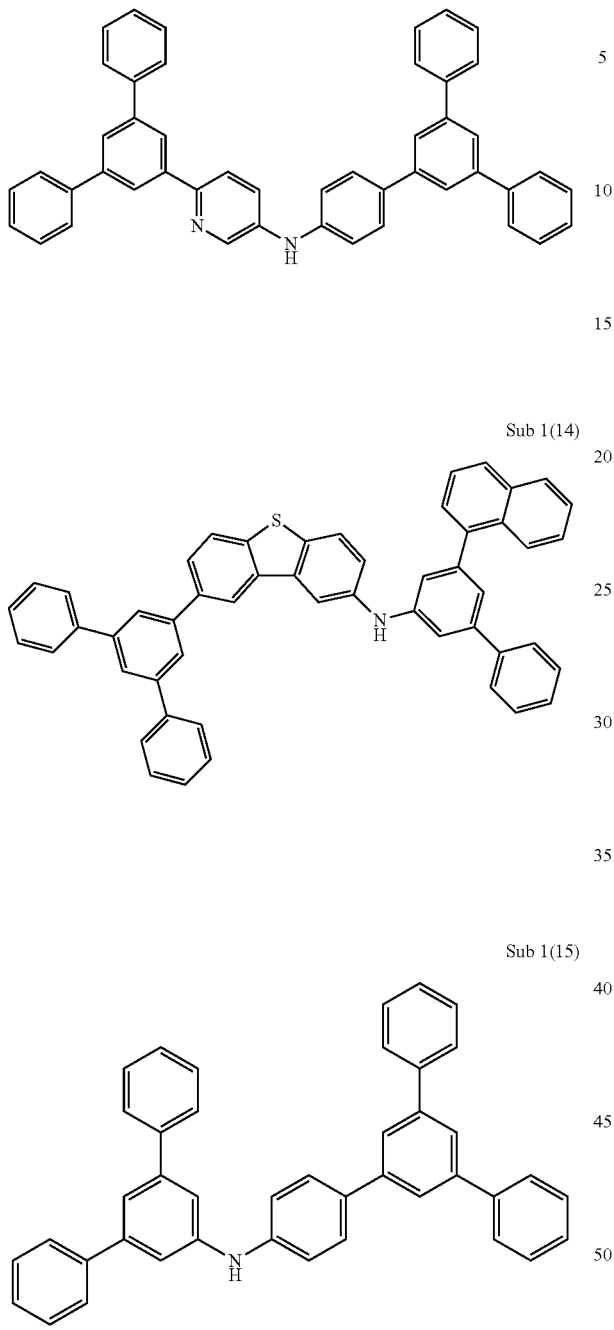

2. Synthesis Example of Compound Sub 2

The compounds comprised in Sub 2 of reaction scheme 1 may be, but not limited to, the following compounds

TABLE 1

| compound | FD-MS | compound | FD-MS |
|---|---|---|---|
| Sub 1(1) | m/z = 473.21($C_{36}H_{27}N$ = 473.61) | Sub 1(2) | m/z = 523.23($C_{40}H_{29}N$ = 523.66) |
| Sub 1(3) | m/z = 673.28($C_{52}H_{35}N$ = 673.84) | Sub 1(4) | m/z = 501.25($C_{38}H_{31}N$ = 501.66) |
| Sub 1(5) | m/z = 529.28($C_{40}H_{35}N$ = 529.71) | Sub 1(6) | m/z = 585.34($C_{44}H_{43}N$ = 585.82) |
| Sub 1(7) | m/z = 529.28($C_{40}H_{35}N$ = 529.71) | Sub 1(8) | m/z = 579.20($C_{42}H_{29}NS$ = 579.75) |
| Sub 1(9) | m/z = 653.24($C_{48}H_{31}NO_2$ = 653.77) | Sub 1(10) | m/z = 705.34($C_{54}H_{43}N$ = 705.93) |
| Sub 1(11) | m/z = 625.28($C_{48}H_{35}N$ = 625.80) | Sub 1(12) | m/z = 599.26($C_{46}H_{33}N$ = 599.76) |
| Sub 1(13) | m/z = 626.27($C_{47}H_{34}N_2$ = 626.79) | Sub 1(14) | m/z = 705.25($C_{52}H_{35}NS$ = 705.91) |
| Sub 1(15) | m/z = 549.25($C_{42}H_{31}N$ = 549.70) | | |

-continued

Sub 2(6)
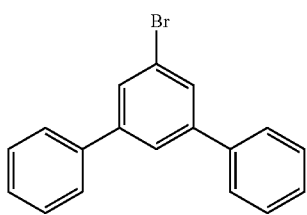

Sub 2(7)
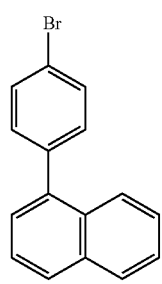

Sub 2(8)
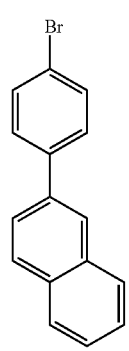

Sub 2(9)
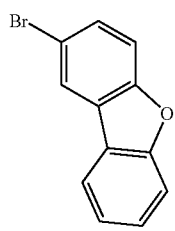

Sub 2(10)
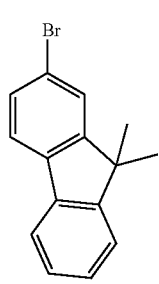

3. Synthesis Example of Compound Represented by Formula 1

(1) Synthesis Example of Compound P-19

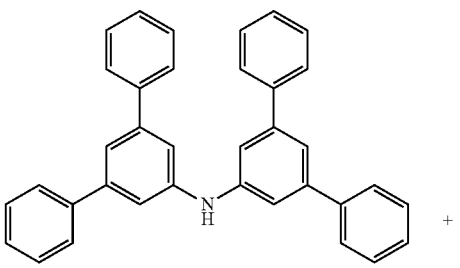
Sub 1(1)

+

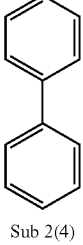
Sub 2(4)

$\xrightarrow{\text{Pd}_2(\text{dba})_3/\text{t-BuONa}/\text{P(t-Bu)}_3}{\text{Toluene}}$

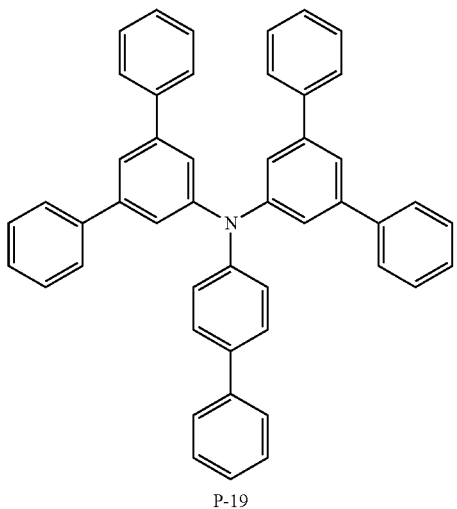
P-19

Sub 1(1) (9.5 g, 20 mmol), Sub 2(4) (4.7 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with CH$_2$Cl$_2$ and water. The organic layer was dried with MgSO$_4$ and concentrated. The concentrate was separated by silica gel column chromatography and recrystallization, whereby compound P-19 was obtained in the amount of 10.3 g (yield: 82%).

(2) Synthesis Example of Compound P-28

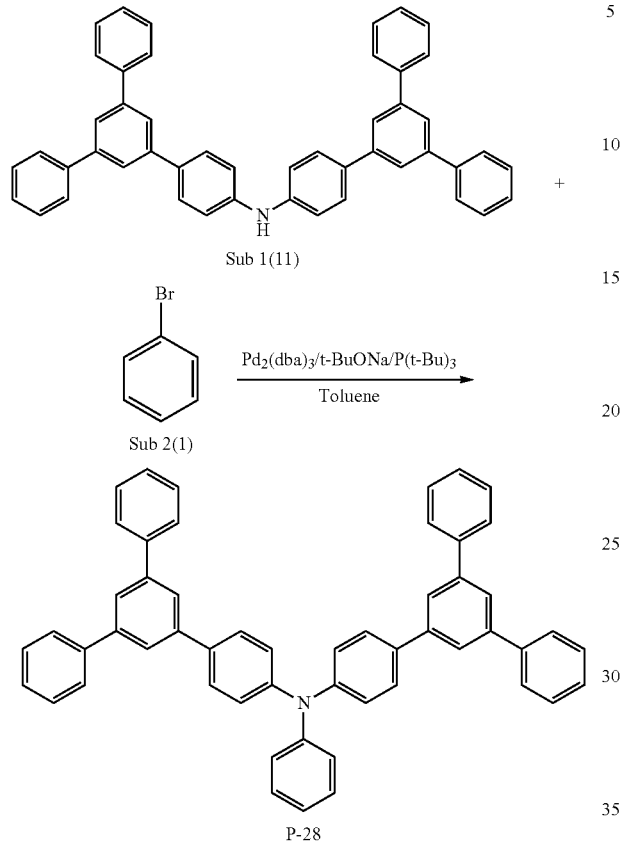

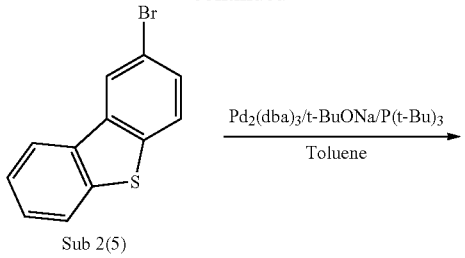

Sub 1(11) (12.5 g, 20 mmol), Sub 2(1) (3.1 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with CH$_2$Cl$_2$ and water. The organic layer was dried with MgSO$_4$ and concentrated. The concentrate was separated by silica gel column chromatography and recrystallization, whereby compound P-28 was obtained in the amount of 11.9 g (yield: 85%).

(3) Synthesis Example of Compound P-34

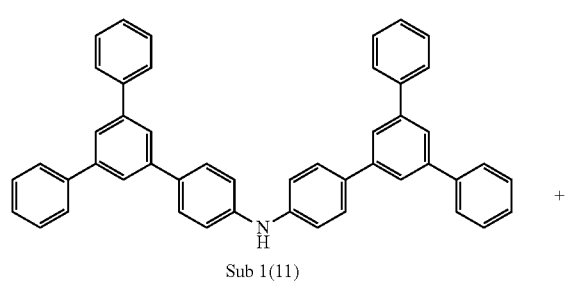

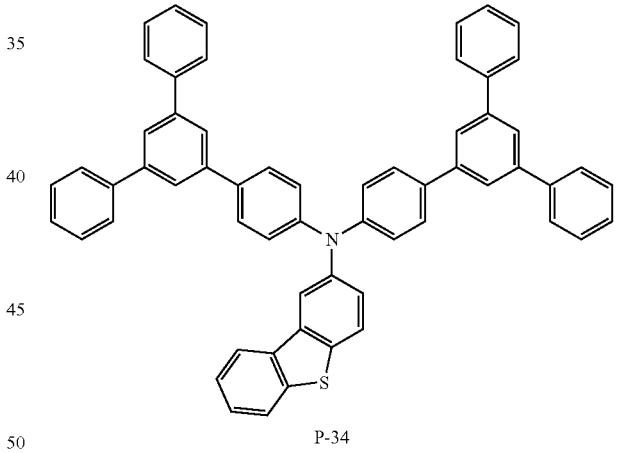

Sub 1(11) (12.5 g, 20 mmol), Sub 2(5) (5.3 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with CH$_2$Cl$_2$ and water. The organic layer was dried with MgSO$_4$ and concentrated. The concentrate was separated by silica gel column chromatography and recrystallization, whereby compound P-34 was obtained in the amount of 12.6 g (yield: 78%).

(4) Synthesis Example of Compound P-36

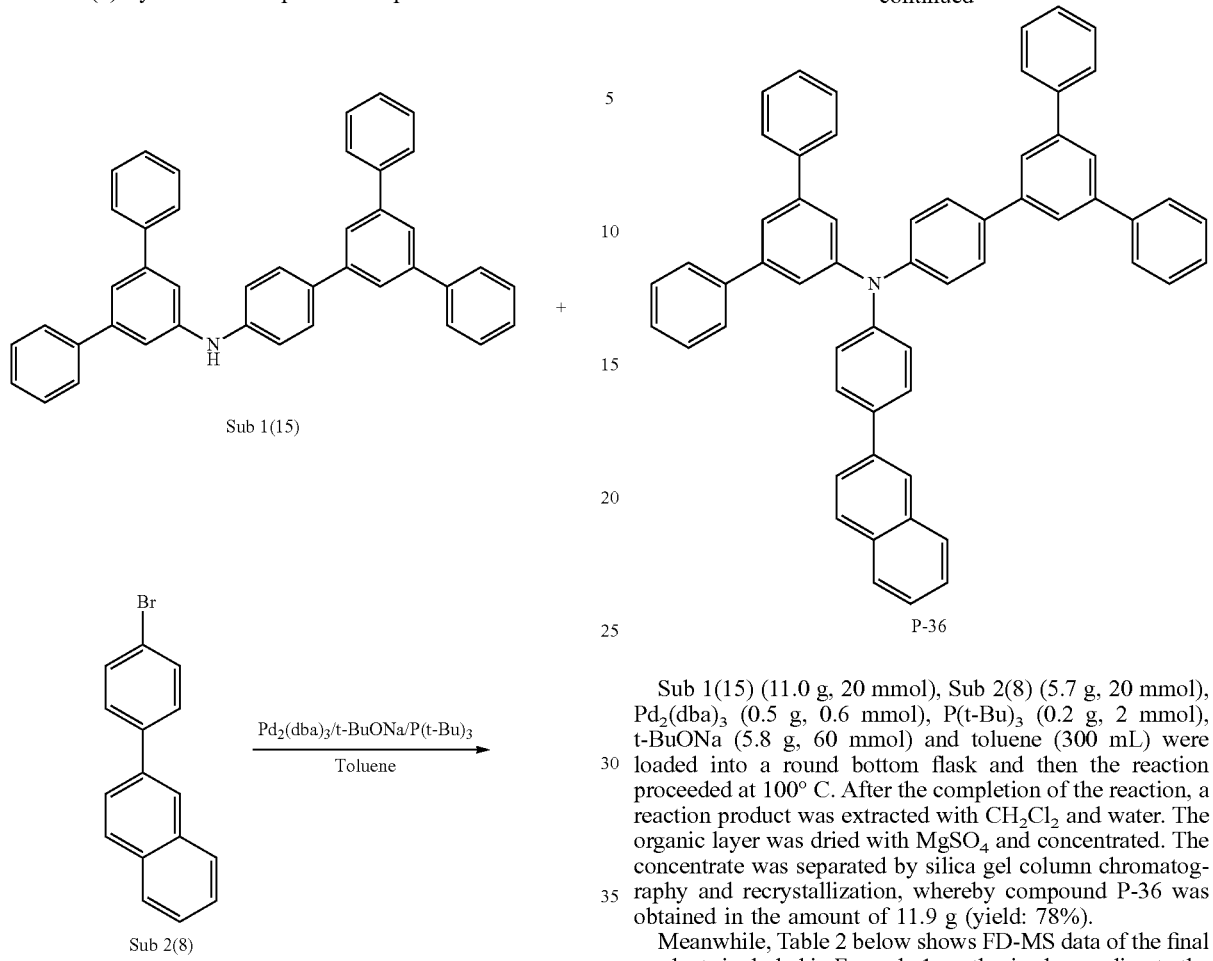

Sub 1(15) (11.0 g, 20 mmol), Sub 2(8) (5.7 g, 20 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were loaded into a round bottom flask and then the reaction proceeded at 100° C. After the completion of the reaction, a reaction product was extracted with CH$_2$Cl$_2$ and water. The organic layer was dried with MgSO$_4$ and concentrated. The concentrate was separated by silica gel column chromatography and recrystallization, whereby compound P-36 was obtained in the amount of 11.9 g (yield: 78%).

Meanwhile, Table 2 below shows FD-MS data of the final products included in Formula 1 synthesized according to the above synthesis.

TABLE 2

| Compound | FD-MS | Compound | FD-MS |
|---|---|---|---|
| P-1 | m/z = 549.25(C$_{42}$H$_{23}$N = 549.70) | P-2 | m/z = 599.26(C$_{46}$H$_{33}$N = 599.76) |
| P-3 | m/z = 749.31(C$_{58}$H$_{39}$N = 749.94) | P-4 | m/z = 577.28(C$_{44}$H$_{35}$N = 577.76) |
| P-5 | m/z = 605.31(C$_{46}$H$_{29}$N = 605.81) | P-6 | m/z = 661.37(C$_{50}$H$_{47}$N = 661.91) |
| P-7 | m/z = 605.31(C$_{46}$H$_{39}$N = 605.81) | P-8 | m/z = 655.23(C$_{48}$H$_{33}$NS = 655.85) |
| P-9 | m/z = 729.27(C$_{54}$H$_{35}$NO$_2$ = 729.86) | P-10 | m/z = 701.31(C$_{54}$H$_{39}$N = 701.89) |
| P-11 | m/z = 649.28(C$_{30}$H$_{35}$N = 649.82) | P-12 | m/z = 799.32(C$_{62}$H$_{41}$N = 800.00) |
| P-13 | m/z = 627.29(C$_{48}$H$_{37}$N = 627.81) | P-14 | m/z = 655.32(C$_{50}$H$_{41}$N = 655.87) |
| P-15 | m/z = 711.39(C$_{54}$H$_{42}$N = 711.97) | P-16 | m/z = 655.32(C$_{50}$H$_{41}$N = 655.87) |
| P-17 | m/z = 731.26(C$_{54}$H$_{37}$NS = 731.94) | P-18 | m/z = 731.26(C$_{54}$H$_{32}$NS = 731.94) |
| P-19 | m/z = 625.28(C$_{48}$H$_{35}$N = 625.80) | P-20 | m/z = 675.29(C$_{52}$H$_{37}$N = 675.86) |
| P-21 | m/z = 825.34(C$_{64}$H$_{43}$N = 826.03) | P-22 | m/z = 681.34(C$_{52}$H$_{43}$N = 681.90) |
| P-23 | m/z = 675.29(C$_{52}$H$_{37}$N = 675.86) | P-24 | m/z = 857.40(C$_{40}$H$_{53}$N = 858.12) |
| P-25 | m/z = 681.34(C$_{52}$H$_{43}$N = 681.90) | P-26 | m/z = 731.26(C$_{54}$H$_{37}$NS = 731.94) |
| P-27 | m/z = 805.30(C$_{60}$H$_{39}$NO$_2$ = 805.96) | P-28 | m/z = 701.31(C$_{54}$H$_{39}$N = 701.89) |
| P-29 | m/z = 725.31(C$_{50}$H$_{39}$N = 725.92) | P-30 | m/z = 853.37(C$_{66}$H$_{47}$N = 854.09) |
| P-31 | m/z = 777.34(C$_{60}$H$_{43}$N = 777.99) | P-32 | m/z = 702.30(C$_{53}$H$_{38}$N$_2$ = 702.88) |
| P-33 | m/z = 831.30(C$_{62}$H$_{41}$NS = 832.06) | P-34 | m/z = 807.30(C$_{60}$H$_{43}$NS = 808.04) |
| P-35 | m/z = 827.36(C$_{64}$H$_{45}$N = 828.05) | P-36 | m/z = 751.32(C$_{58}$H$_{41}$N = 751.95) |

II. Synthesis Example of Compound Represented by Formula 7

The compounds (final product 2) of the present invention represented by Formula 7 can be synthesized by reaction of Sub 3 or Sub 4 with Sub 5 as illustrated in, but not limited to, the following Reaction Scheme 3.

<Reaction Scheme 3>

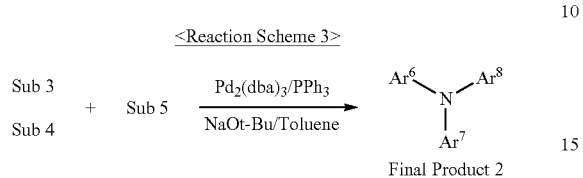

1. Synthesis Example of Compound Sub 3

Compound Sub 3 of the above Reaction Scheme 3 can be synthesized as illustrated in, but not limited to, the following Reaction Scheme 4.

<Reaction Scheme 4>

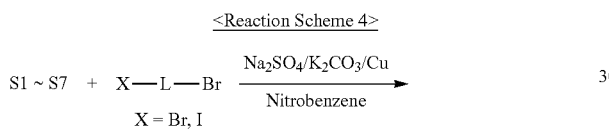

Wherein compounds S1 to S7 may be as follows:

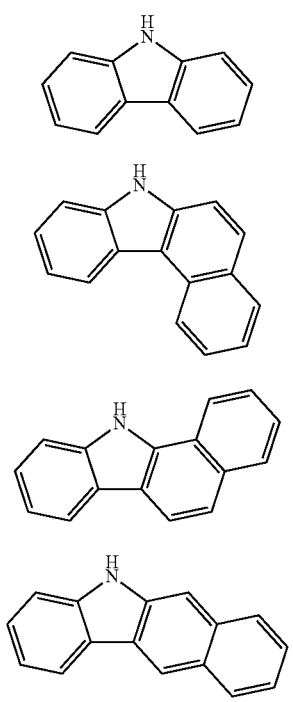

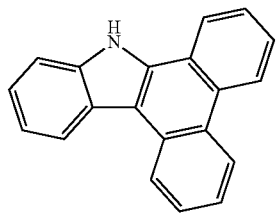

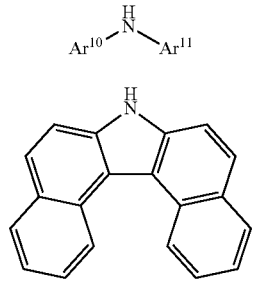

In the above Reaction Scheme 4, L corresponds to $L^3$ or $L^5$ defined in Formulas 7-a and 7-c.

(1) Synthesis Example of Compound Sub 3-1-1 (L=Biphenyl)

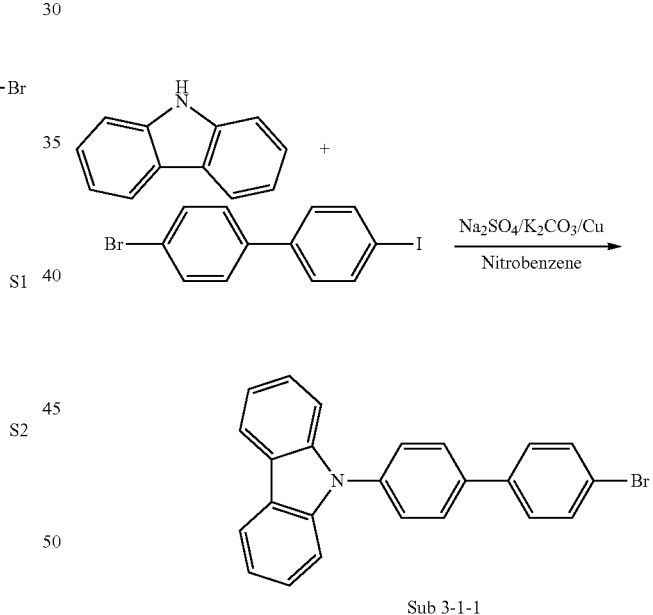

Sub 3-1-1

The starting material, 9H-carbazole (50.16 g, 300 mmol), was dissolved in nitrobenzene (600 ml), 4-bromo-4'-iodo-1,1'-biphenyl (129.2 g, 360 mmol), $Na_2SO_4$ (42.6 g, 300 mmol), $K_2CO_3$ (41.4 g, 300 mmol) and Cu (5.72 g, 90 mmol) were added, and the mixture was stirred at 200° C. Upon the completion of the reaction, nitrobenzene from a reaction product was removed by distillation, followed by extracting with $CH_2Cl_2$ and water. The organic layer was dried with $MgSO_4$ and concentrated. The concentrate was separated by silica gel column chromatography and recrystallization, whereby product was obtained in the amount of 80.05 g (yield: 67%).

(2) Synthesis Example of Compound Sub 3-1-2
(L=9,9-Dimethyl-9H-Fluorene)

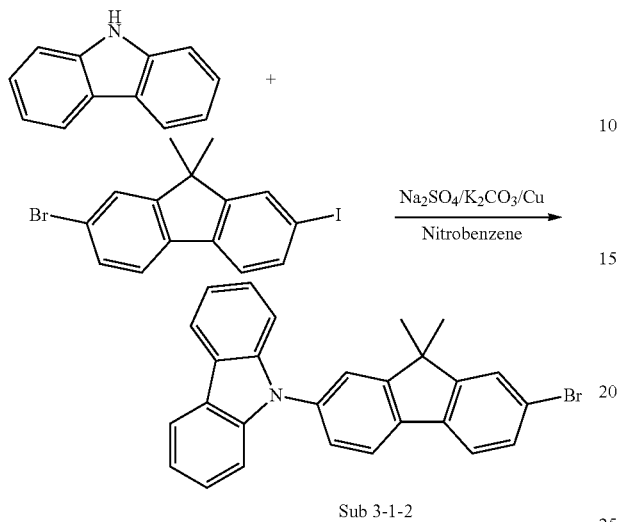

Sub 3-1-2

Product was obtained in the amount of 88.11 g (yield: 67%) where 9H-carbazole (50.16 g, 300 mmol) as a starting material, 2-bromo-7-iodo-9,9-dimethyl-9H-fluorene (143.7 g, 360 mmol), $Na_2SO_4$ (42.6 g, 300 mmol), $K_2CO_3$ (41.4 g, 300 mmol), Cu (5.72 g, 90 mmol) and nitrobenzene were used in the same manner as described above for the synthesis of compound Sub 3-1-1.

(3) Synthesis Example of Compound Sub 3-1-3
(L=9,9-Dimethyl-9H-Fluorene)

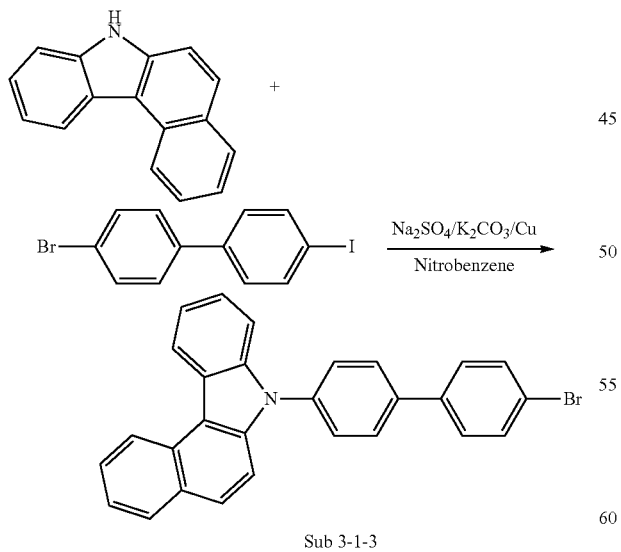

Sub 3-1-3

Product was obtained in the amount of 92.8 g (yield: 69%) where 7H-benzo[c]carbazole (65.18 g, 300 mmol) as a starting material, 4-bromo-4'-iodo-1,1'-biphenyl (129.2 g, 360 mmol), $Na_2SO_4$ (42.6 g, 300 mmol), $K_2CO_3$ (41.4 g, 300 mmol), Cu (5.72 g, 90 mmol) and nitrobenzene were used in the same manner as described above for the synthesis of compound Sub 3-1-1.

(4) Synthesis Example of Compound Sub 3-1-4
(L=9,9-Dimethyl-9H-Fluorene)

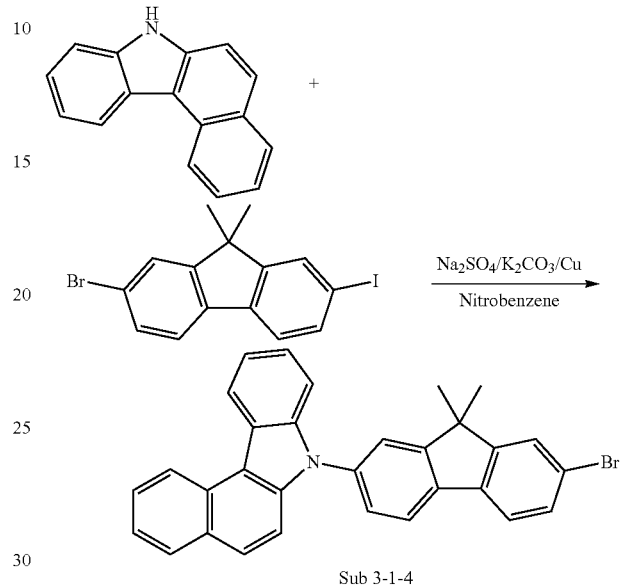

Sub 3-1-4

Product was obtained in the amount of 95.24 g (yield: 65%) where 7H-benzo[c]carbazole (65.18 g, 300 mmol) as a starting material, 2-bromo-7-iodo-9,9-dimethyl-9H-fluorene (143.7 g, 360 mmol), $Na_2SO_4$ (42.6 g, 300 mmol), $K_2CO_3$ (41.4 g, 300 mmol), Cu (5.72 g, 90 mmol) and nitrobenzene were used in the same manner as described above for the synthesis of compound Sub 3-1-1.

(5) Synthesis Example of Compound Sub 3-1-5
(L=Biphenyl)

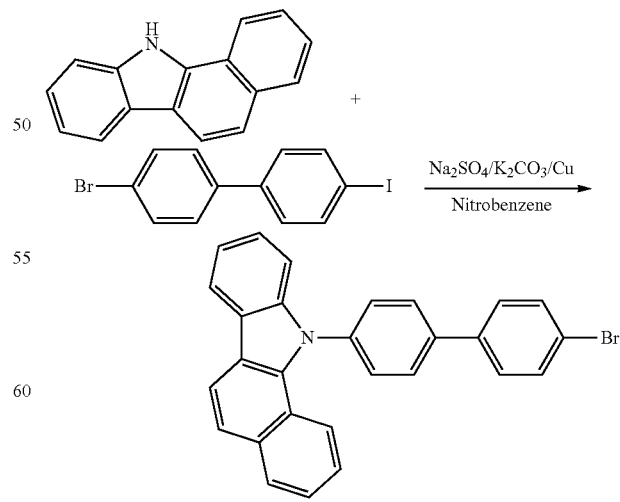

Sub 3-1-5

Product was obtained in the amount of 80.05 g (yield: 62%) where 11H-benzo[a]carbazole (65.18 g, 300 mmol) as a starting material, 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol) and nitrobenzene were used in the same manner as described above for the synthesis of compound Sub 3-1-1.

(6) Synthesis Example of Compound Sub 3-1-6 (L=9,9-Dimethyl-9H-Fluorene)

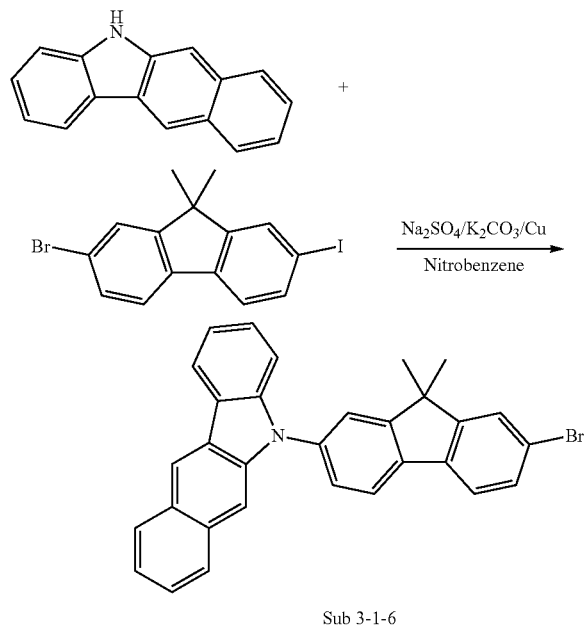

Sub 3-1-6

Product was obtained in the amount of 93.78 g (yield: 64%) where 5H-benzo[b]carbazole (65.18 g, 300 mmol) as a starting material, 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol) and nitrobenzene were used in the same manner as described above for the synthesis of compound Sub 3-1-1.

(7) Synthesis Example of Compound Sub 3-1-7 (L=Biphenyl)

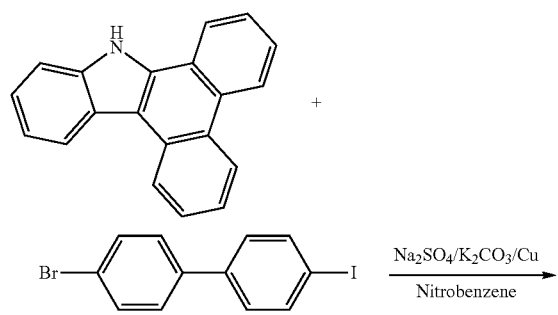

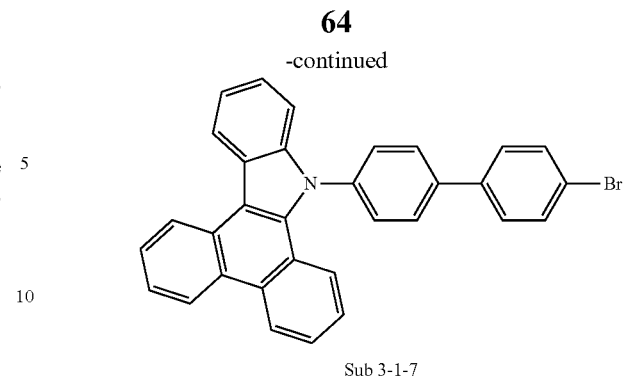

Sub 3-1-7

Product was obtained in the amount of 98.7 g (yield: 66%) where 9H-dibenzo[a,c]carbazole (80.2 g, 300 mmol) as a starting material, 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol) and nitrobenzene were used in the same manner as described above for the synthesis of compound Sub 3-1-1.

(8) Synthesis Example of Compound Sub 3-1-8 (L=Biphenyl)

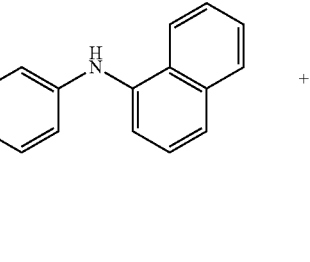

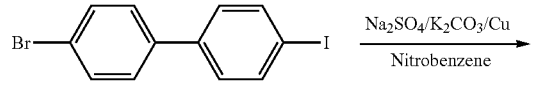

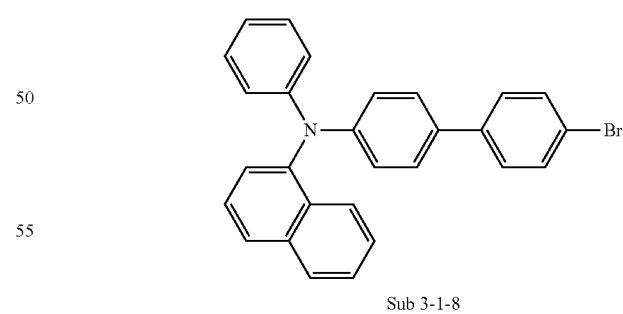

Sub 3-1-8

Product was obtained in the amount of 89.2 g (yield: 66%) where N-phenylnaphthalen-1-amine (65.8 g, 300 mmol) as a starting material, 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol) and nitrobenzene were used in the same manner as described above for the synthesis of compound Sub 3-1-1.

(9) Synthesis Example of Compound Sub 3-1-9 (L=9,9-Dimethyl-9H-Fluorene)

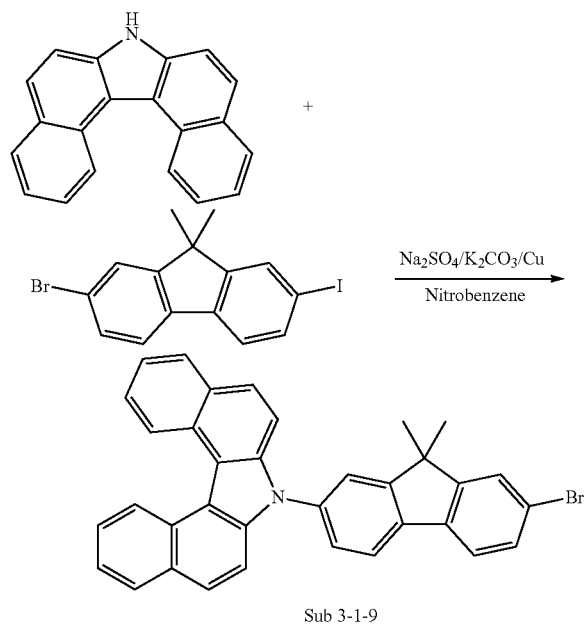

Sub 3-1-9

Product was obtained in the amount of 98.5 g (yield: 61%) where 7H-dibenzo[c,g]carbazole (80.2 g, 300 mmol) as a starting material, 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol) and nitrobenzene were used in the same manner as described above for the synthesis of compound Sub 3-1-1.

2. Synthesis Example of Compound Represented by Sub 4

Compound Sub 4 of the above Reaction Scheme 3 can be synthesized as illustrated in, but not limited to, the following Reaction Scheme 5.

<Reaction Scheme 5>

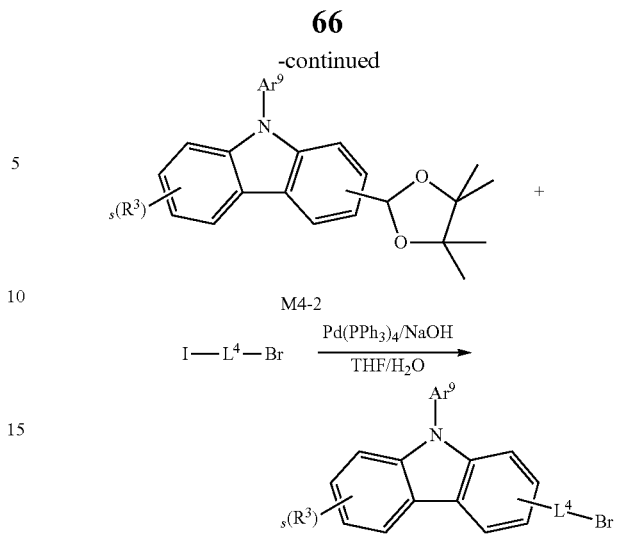

Sub 4

(1) Synthesis Example of Compound M4-2-1 (g=0, Ar$^9$=Phenyl)

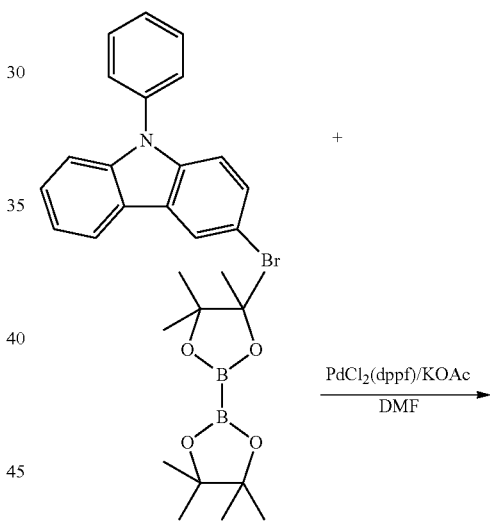

M4-2-1

After dissolving 3-bromo-9-phenyl-9H-carbazole (45.1 g, 140 mmol) in DMF 980 mL, Bispinacolborate (39.1 g, 154 mmol), PdCl$_2$(dppf) catalyst (3.43 g, 4.2 mmol) and KOAc (41.3 g, 420 mmol) were added in order, and then the mixture was stirred for 24 hours, thereby a borate compound was synthesized. The obtained compound was separated by silica gel column chromatography, and was then recrystallized, whereby final borate compound was obtained in the amount of 35.2 g (yield: 68%).

(2) Synthesis Example of Compound M4-2-2 (g=0, Ar⁹=Biphenyl)

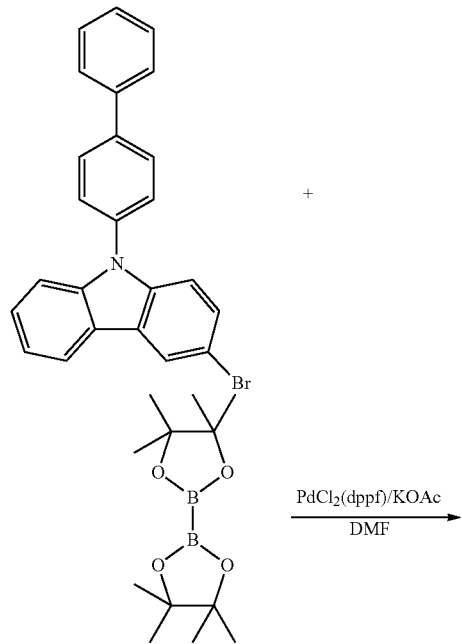

Product was obtained in the amount of 40 g (yield: 64%) where 3-bromo-9-biphenyl-9H-carbazole (45.1 g, 140 mmol), DMF 980 mL, Bispinacolborate (39.1 g, 154 mmol), PdCl₂(dppf) catalyst (3.43 g, 4.2 mmol) and KOAc (41.3 g, 420 mmol) were used in the same manner as described above for the synthesis of compound M4-2-1.

(3) Synthesis Example of Compound Sub 4-1-1 [g=0, Ar⁹=Phenyl, L⁶=Biphenyl (Linear)]

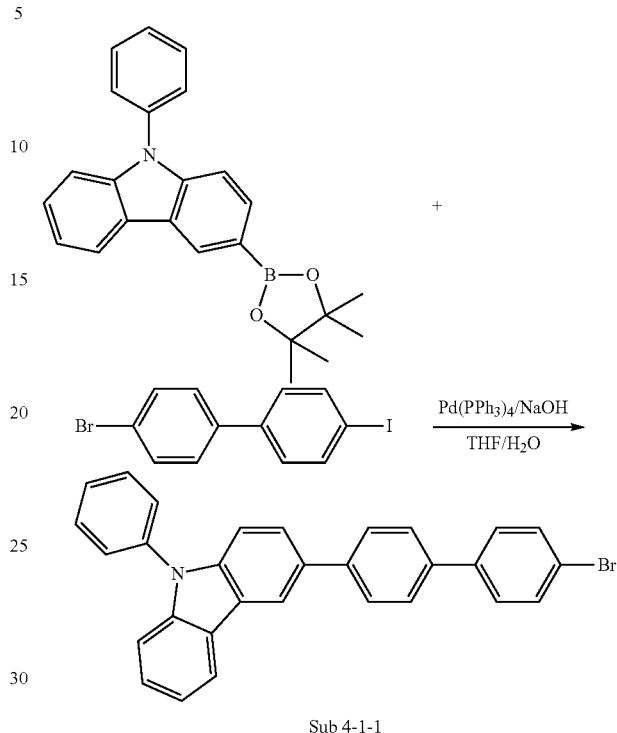

After dissolving M4-2-1 (29.5 g, 80 mmol) in THF 360 mL, 4-bromo-4'-iodo-1,1'-biphenyl (30.16 g, 84 mmol), Pd(PPh₃)₄ (2.8 g, 2.4 mmol), NaOH (9.6 g, 240 mmol) and water 180 mL were added, and then the mixture was refluxed with stirring. Upon the completion of the reaction, a reaction product was extracted with ether and water. The organic layer was dried with MgSO₄ and concentrated. The concentrate was separated by silica gel column chromatography and recrystallization, whereby final product was obtained in the amount of 26.56 g (yield: 70%).

(4) Synthesis Example of Compound Sub 4-1-2 [g=0, Ar⁹=Phenyl, L⁶=Phenyl]

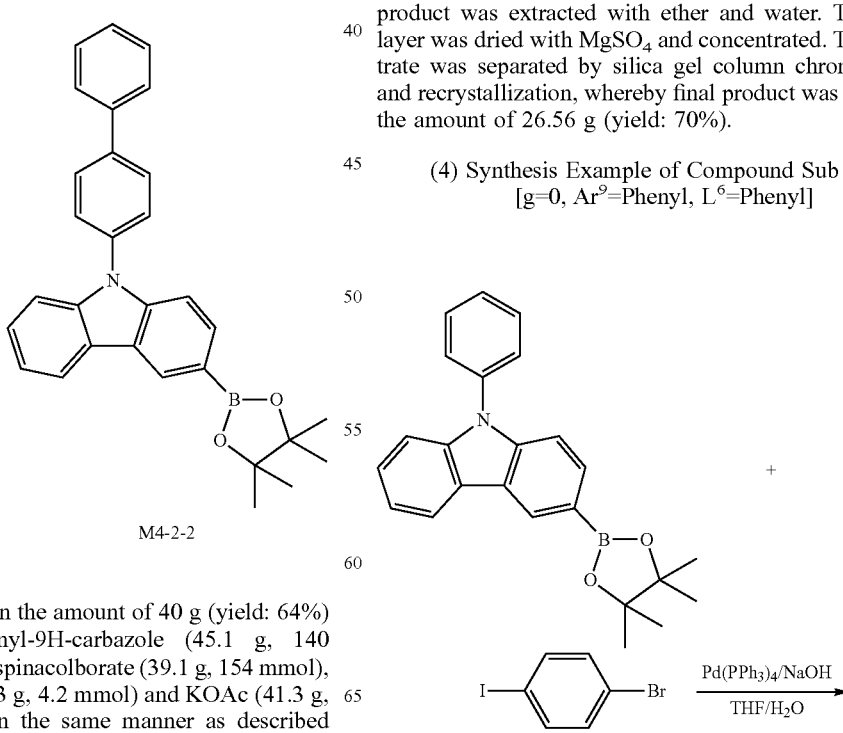

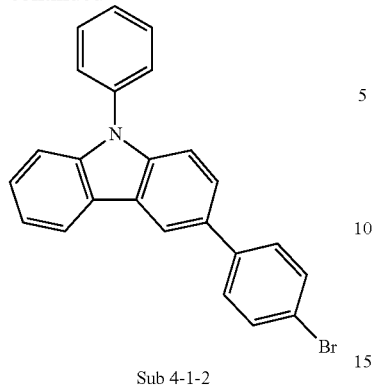

Sub 4-1-2

After dissolving M4-2-1 (29.5 g, 80 mmol) in THF 360 mL, 1-bromo-4-iodobenzene (23.8 g, 84 mmol), Pd(PPh$_3$)$_4$ (2.8 g, 2.4 mmol), NaOH (9.6 g, 240 mmol) and water 180 mL were added, and then the mixture was refluxed with stirring. Upon the completion of the reaction, a reaction product was extracted with ether and water. The organic layer was dried with MgSO$_4$ and concentrated. The concentrate was separated by silica gel column chromatography and recrystallization, whereby compound final product was obtained in the amount of 22.9 g (yield: 72%).

(5) Synthesis Example of Compound Sub 4-1-3
[g=0, Ar$^9$=Phenyl, L$^6$=Biphenyl (Non-Linear)]

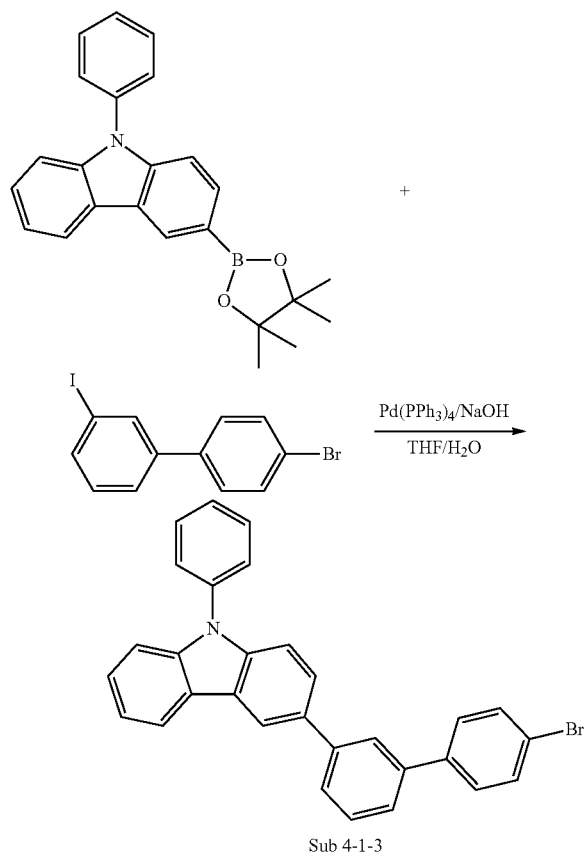

Sub 4-1-3

After dissolving M4-2-1 (29.5 g, 80 mmol) in THF 360 mL, 4'-bromo-3-iodo-1,1'-biphenyl (30.16 g, 84 mmol), Pd(PPh$_3$)$_4$ (2.8 g, 2.4 mmol), NaOH (9.6 g, 240 mmol) and water 180 mL were added, and then the mixture was refluxed with stirring. Upon the completion of the reaction, a reaction product was extracted with ether and water. The organic layer was dried with MgSO$_4$ and concentrated. The concentrate was separated by silica gel column chromatography and recrystallization, whereby compound final product was obtained in the amount of 24.7 g (yield: 65%).

(6) Synthesis Example of Compound Sub 4-1-4
[g=0, Ar$^9$=Biphenyl, L$^6$=Biphenyl (Linear)]

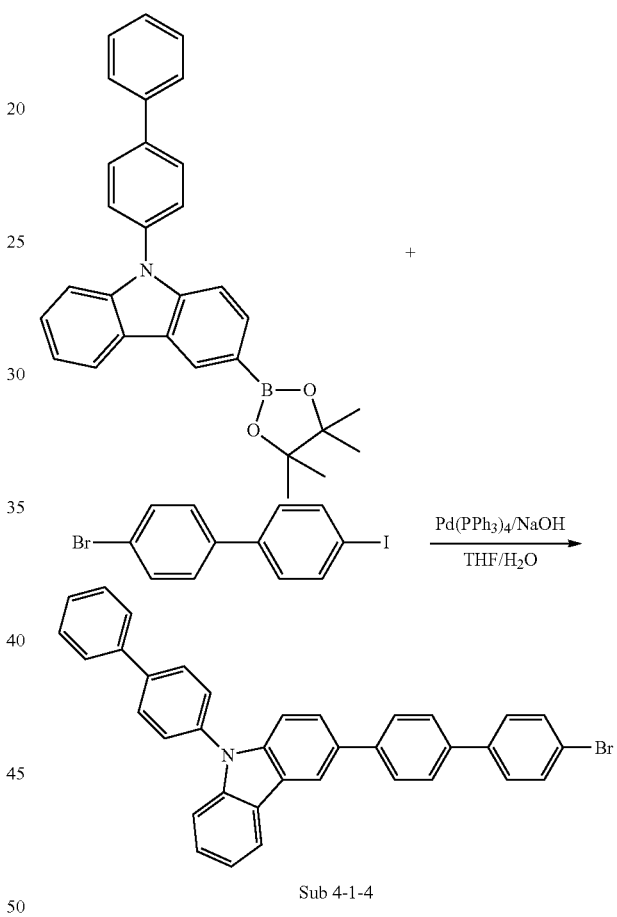

Sub 4-1-4

After dissolving M4-2-2 (35.63 g, 80 mmol) in THF 360 mL, 4-bromo-4'-iodo-1,1'-biphenyl (30.16 g, 84 mmol), Pd(PPh$_3$)$_4$ (2.8 g, 2.4 mmol), NaOH (9.6 g, 240 mmol) and water 180 mL were added, and then the mixture was refluxed with stirring. Upon the completion of the reaction, a reaction product was extracted with ether and water. The organic layer was dried with MgSO$_4$ and concentrated. The concentrate was separated by silica gel column chromatography and recrystallization, whereby compound final product was obtained in the amount of 29.51 g (yield: 67%).

3. Synthesis Example of Compound Sub 5

Compound Sub 5 of the above Reaction Scheme 3 can be synthesized as illustrated in, but not limited to, the following Reaction Scheme 6.

<Reaction Scheme 6>

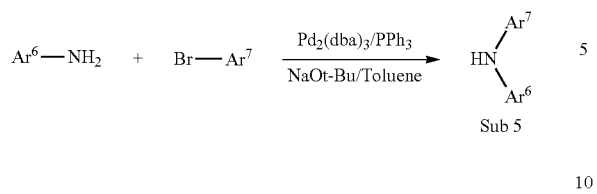

(1) Synthesis Example of Compound Sub 5-28

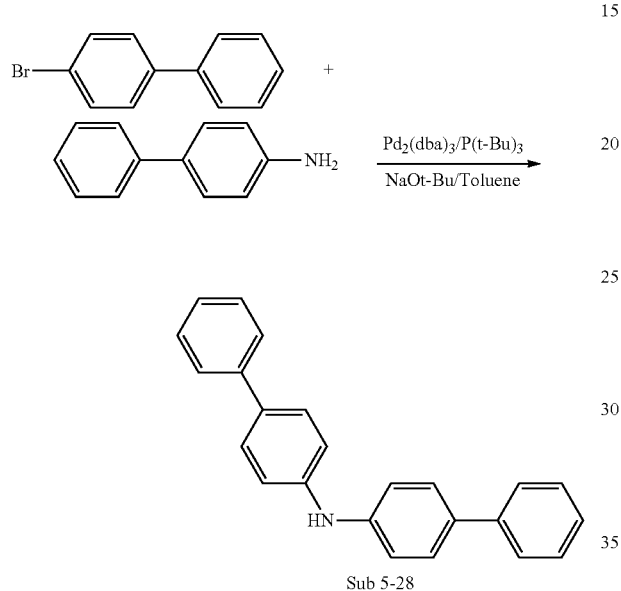

After dissolving 4-bromo-1,1'-biphenyl (37.88 g, 162.5 mmol) in toluene (2200 mL) in a round bottom flask, [1,1'-biphenyl]-4-amine (25 g, 147.7 mmol), $Pd_2(dba)_3$ (6.76 g, 7.4 mmol), $P(t-Bu)_3$ (3 g, 14.8 mmol) and NaOt-Bu (66.62 g, 693.2 mmol) were added in order, and then the mixture was stirred at 100° C. Upon the completion of the reaction, a reaction product was extracted with ether and water. The organic layer was dried with $MgSO_4$ and concentrated. The concentrate was separated by silica gel column chromatography and recrystallization, whereby a product was obtained in the amount of 28 g (yield: 77%).

Meanwhile, the compounds comprised in Sub 5 may be, but not limited to, the following compounds, and Table 3 below shows FD-MS (Field Desorption-Mass Spectrometry) data of the compounds.

Sub 5-1

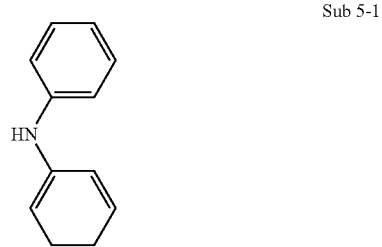

Sub 5-2

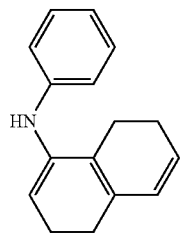

Sub 5-3

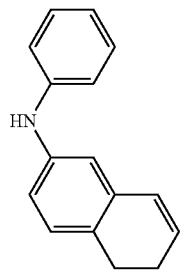

Sub 5-4

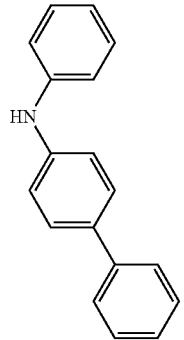

Sub 5-5

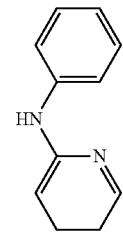

Sub 5-6

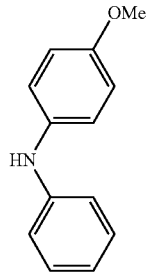

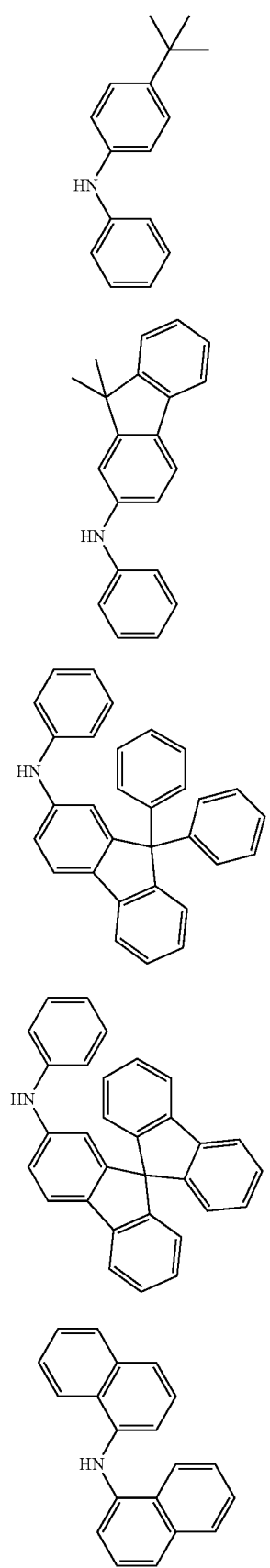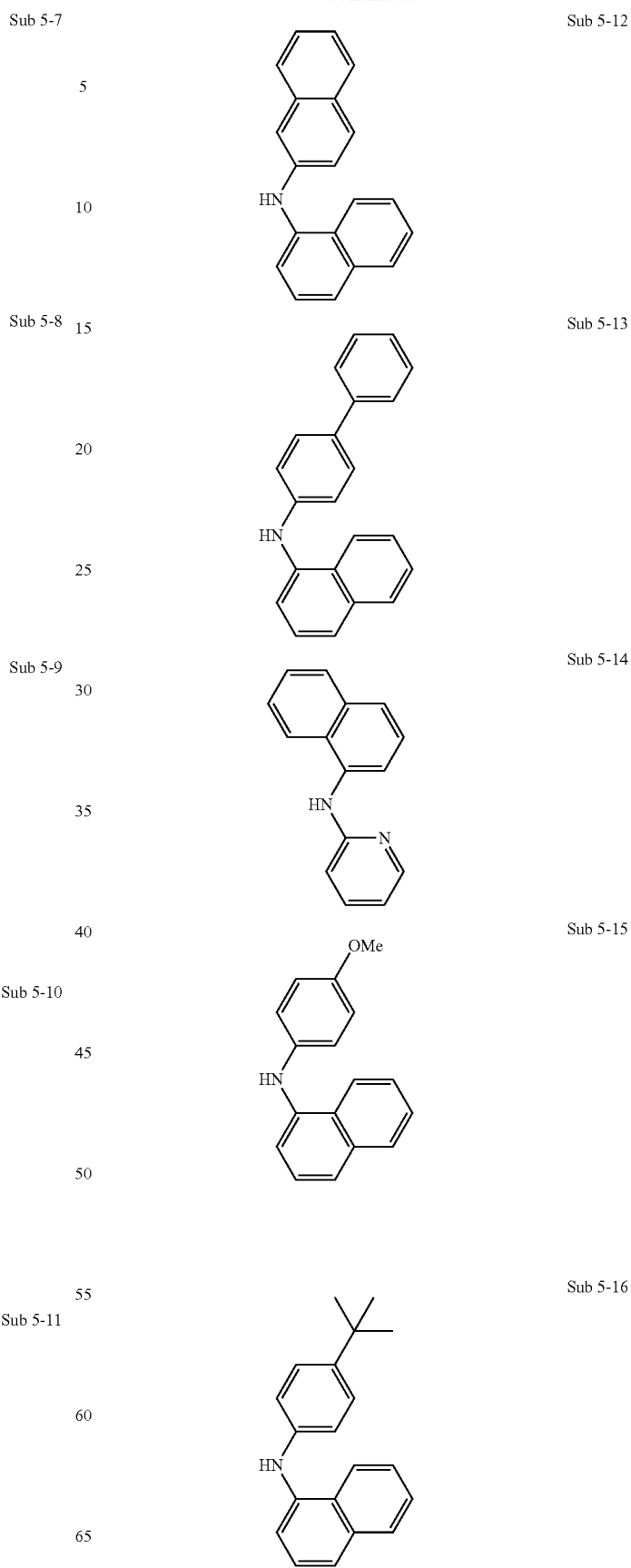

Sub 5-17
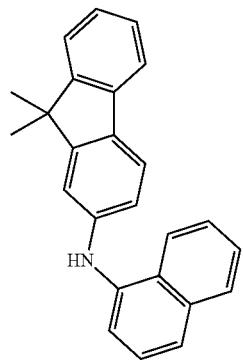
Sub 5-18
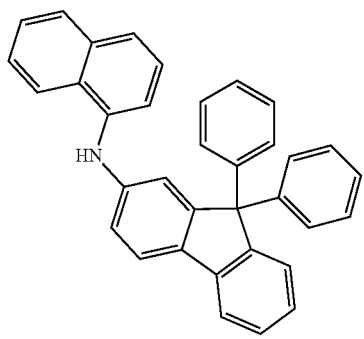
Sub 5-19
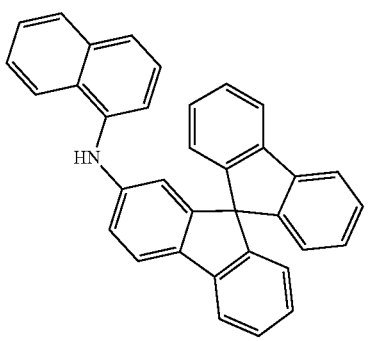
Sub 5-20
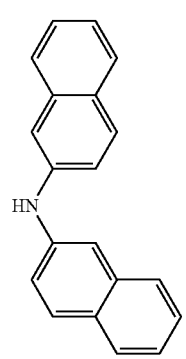
Sub 5-21
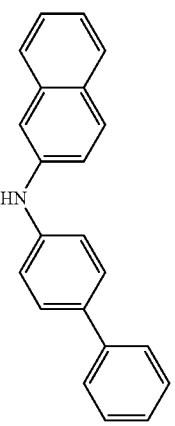
Sub 5-22
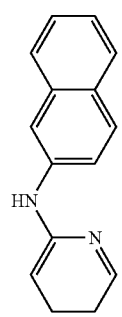
Sub 5-23
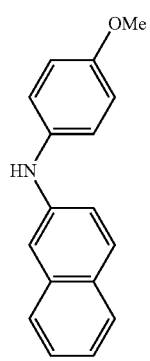
Sub 5-24
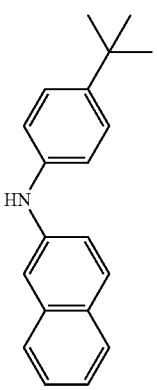

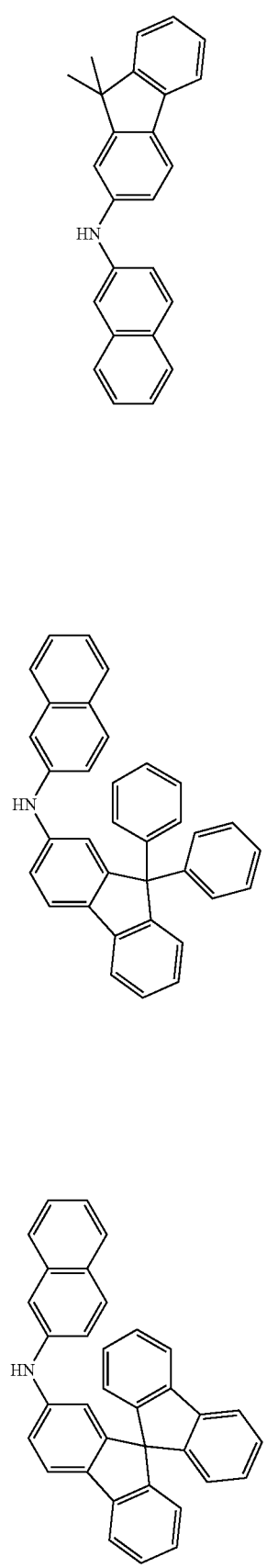
Sub 5-25
Sub 5-26
Sub 5-27
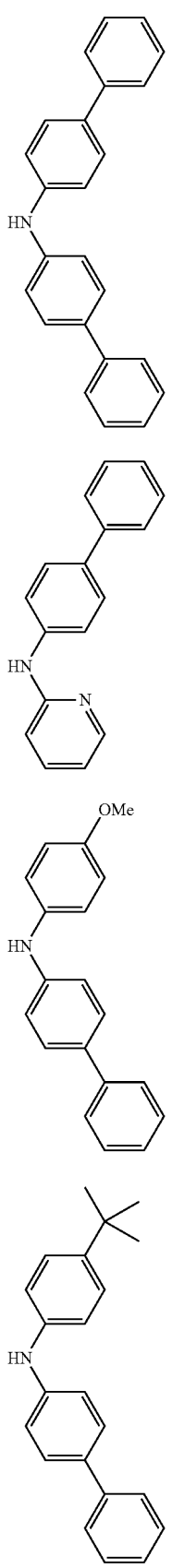
Sub 5-28
Sub 5-29
Sub 5-30
Sub 5-31

Sub 5-32
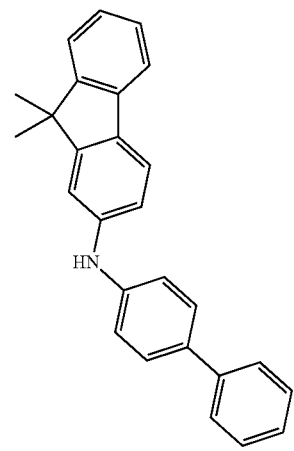
Sub 5-33
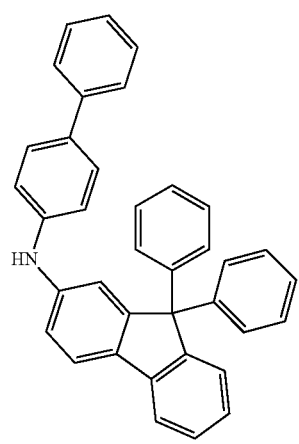
Sub 5-34
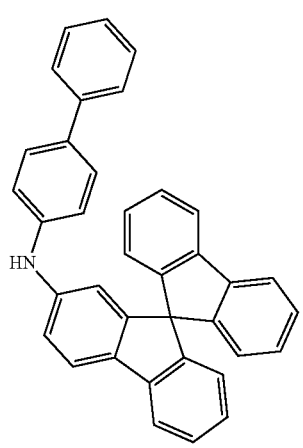
Sub 5-35
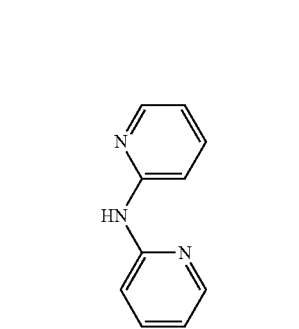
Sub 5-36
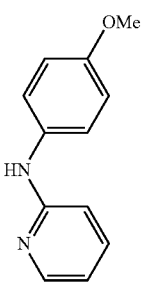
Sub 5-37
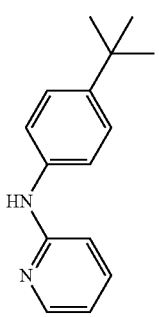
Sub 5-38
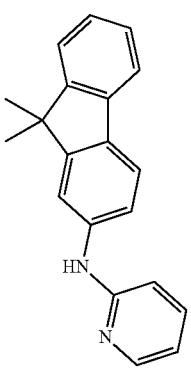
Sub 5-39
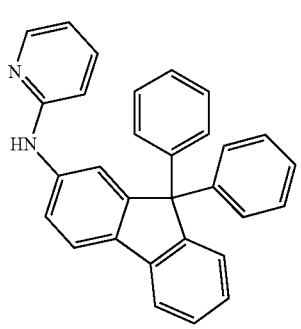
Sub 5-40
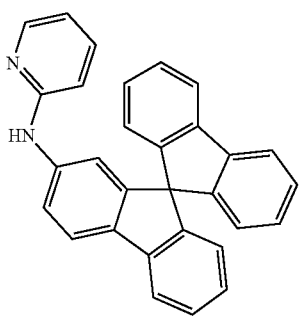

Sub 5-41
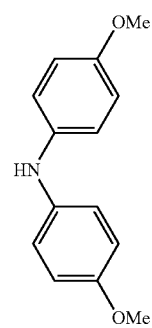
Sub 5-42
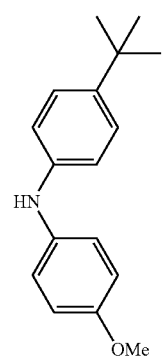
Sub 5-43
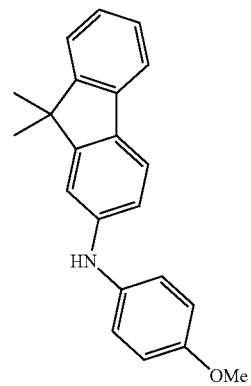
Sub 5-44
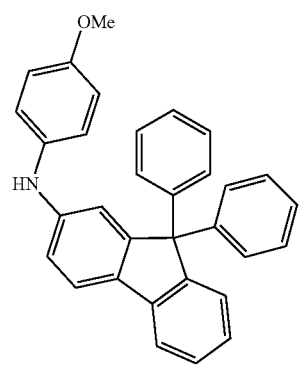
Sub 5-45
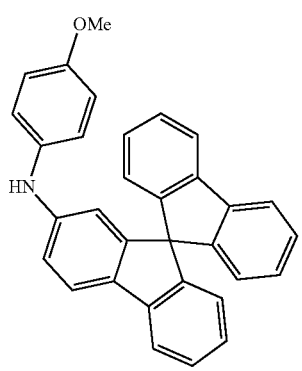
Sub 5-46
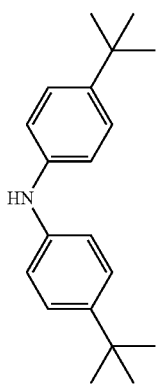
Sub 5-47
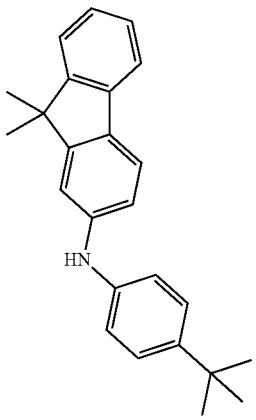
Sub 5-48
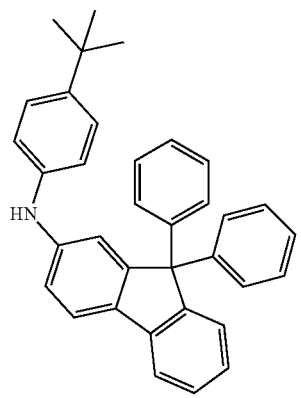

Sub 5-49

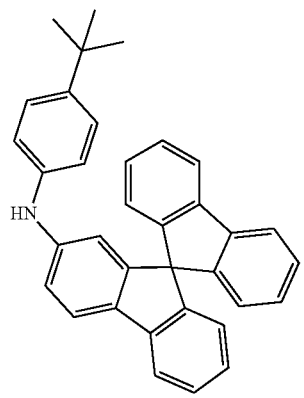

Sub 5-50

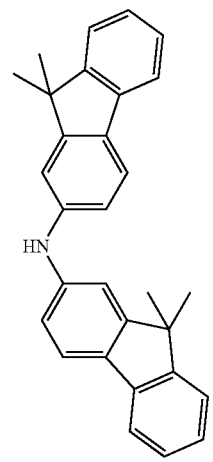

Sub 5-51

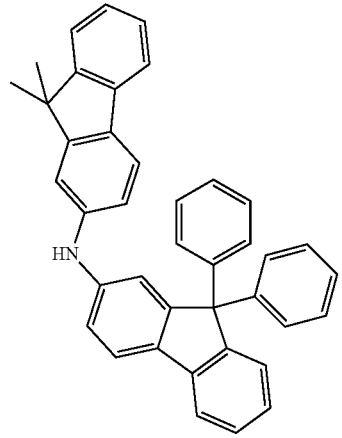

Sub 5-52

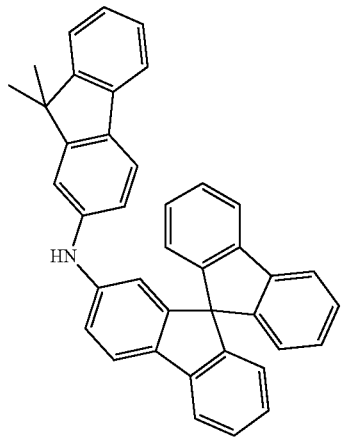

TABLE 3

| Compound | FD-MS | Compound | FD-MS |
|---|---|---|---|
| Sub 5-1 | m/z = 169.09($C_{12}H_{11}N$ = 169.22) | Sub 5-2 | m/z = 219.10($C_{16}H_{13}N$ = 219.28) |
| Sub 5-3 | m/z = 219.10($C_{16}H_{13}N$ = 219.28) | Sub 5-4 | m/z = 245.12($C_{18}H_{15}N$ = 245.32) |
| Sub 5-5 | m/z = 170.08($C_{11}H_{10}N_2$ = 170.21) | Sub 5-6 | m/z = 199.10($C_{10}H_{13}NO$ = 199.25) |
| Sub 5-7 | m/z = 225.15($C_{16}H_{10}N$ = 225.33) | Sub 5-8 | m/z = 285.15($C_{21}H_{19}N$ = 285.38) |
| Sub 5-9 | m/z = 409.18($C_{31}H_{23}N$ = 409.52) | Sub 5-10 | m/z = 407.17($C_{31}H_{23}N$ = 407.51) |
| Sub 5-11 | m/z = 269.12($C_{20}H_{15}N$ = 269.34) | Sub 5-12 | m/z = 269.12($C_{20}H_{15}N$ = 269.34) |
| Sub 5-13 | m/z = 295.14($C_{22}H_{17}N$ = 295.38) | Sub 5-14 | m/z = 220.10($C_{15}H_{12}N_2$ = 220.27) |
| Sub 5-15 | m/z = 249.12($C_{17}H_{12}NO$ = 249.31) | Sub 5-16 | m/z = 275.17($C_{20}H_{21}N$ = 275.39) |
| Sub 5-17 | m/z = 335.17($C_{25}H_{23}N$ = 335.44) | Sub 5-18 | m/z = 459.20($C_{33}H_{25}N$ = 459.58) |
| Sub 5-19 | m/z = 457.18($C_{35}H_{23}N$ = 457.56) | Sub 5-20 | m/z = 269.12($C_{20}H_{15}N$ = 269.34) |
| Sub 5-21 | m/z = 295.14($C_{22}H_{17}N$ = 295.38) | Sub 5-22 | m/z = 220.10($C_{15}H_2N_2$ = 220.27) |
| Sub 5-23 | m/z = 249.12($C_{17}H_{19}NO$ = 249.31) | Sub 5-24 | m/z = 275.17($C_{20}H_{21}N$ = 275.39) |
| Sub 5-25 | m/z = 335.17($C_{25}H_{21}N$ = 335.44) | Sub 5-26 | m/z = 459.20($C_{35}H_{25}N$ = 459.28) |
| Sub 5-27 | m/z = 457.18($C_{35}H_{23}N$ = 457.56) | Sub 5-28 | m/z = 321.15($C_{24}H_{19}N$ = 321.41) |
| Sub 5-29 | m/z = 246.12($C_{17}H_{14}N_2$ = 246.31) | Sub 5-30 | m/z = 275.13($C_{19}H_{17}NO$ = 275.34) |
| Sub 5-31 | m/z = 301.18($C_{22}H_{23}N$ = 301.42) | Sub 5-32 | m/z = 361.18($C_{27}H_{23}N$ = 361.48) |
| Sub 5-33 | m/z = 485.21($C_{37}H_{27}N$ = 485.62) | Sub 5-34 | m/z = 483.20($C_{37}H_{25}N$ = 483.60) |
| Sub 5-35 | m/z = 171.08($C_{10}H_{09}N_3$ = 171.20) | Sub 5-36 | m/z = 200.09($C_{12}H_{12}N_2O$ = 200.24) |
| Sub 5-37 | m/z = 226.15($C_{15}H_{18}N_2$ = 226.32) | Sub 5-38 | m/z = 286.15($C_{20}H_{18}N_2$ = 286.37) |
| Sub 5-39 | m/z = 410.18($C_{30}H_{22}N_2$ = 410.51) | Sub 5-40 | m/z = 408.16($C_{30}H_{20}N_2$ = 408.49) |
| Sub 5-41 | m/z = 229.11($C_{14}H_{19}NO_2$ = 229.27) | Sub 5-42 | m/z = 255.16($C_{17}H_{23}NO$ = 255.35) |
| Sub 5-43 | m/z = 315.16($C_{22}H_{23}NO$ = 315.41) | Sub 5-44 | m/z = 439.19($C_{32}H_{25}NO$ = 439.55) |
| Sub 5-45 | m/z = 437.18($C_{32}H_{23}NO$ = 437.53) | Sub 5-46 | m/z = 281.21($C_{20}H_{27}N$ = 281.44) |
| Sub 5-47 | m/z = 341.21($C_{25}H_{27}N$ = 341.49) | Sub 5-48 | m/z = 465.25($C_{35}H_{31}N$ = 465.63) |
| Sub 5-49 | m/z = 463.23($C_{35}H_{29}N$ = 463.61) | Sub 5-50 | m/z = 401.21($C_{30}H_{27}N$ = 401.54) |
| Sub 5-51 | m/z = 525.25($C_{40}H_{31}N$ = 525.68) | Sub 5-52 | m/z = 523.23($C_{60}H_{29}N$ = 523.66) |

4. Synthesis Example of Compound Represented by Formula 7

(1) Synthesis Example of Compound 1-17

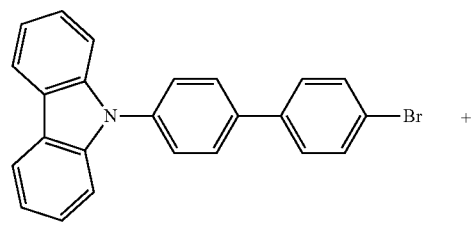

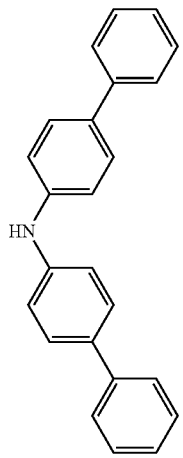

(2) Synthesis Example of Compound 1-32

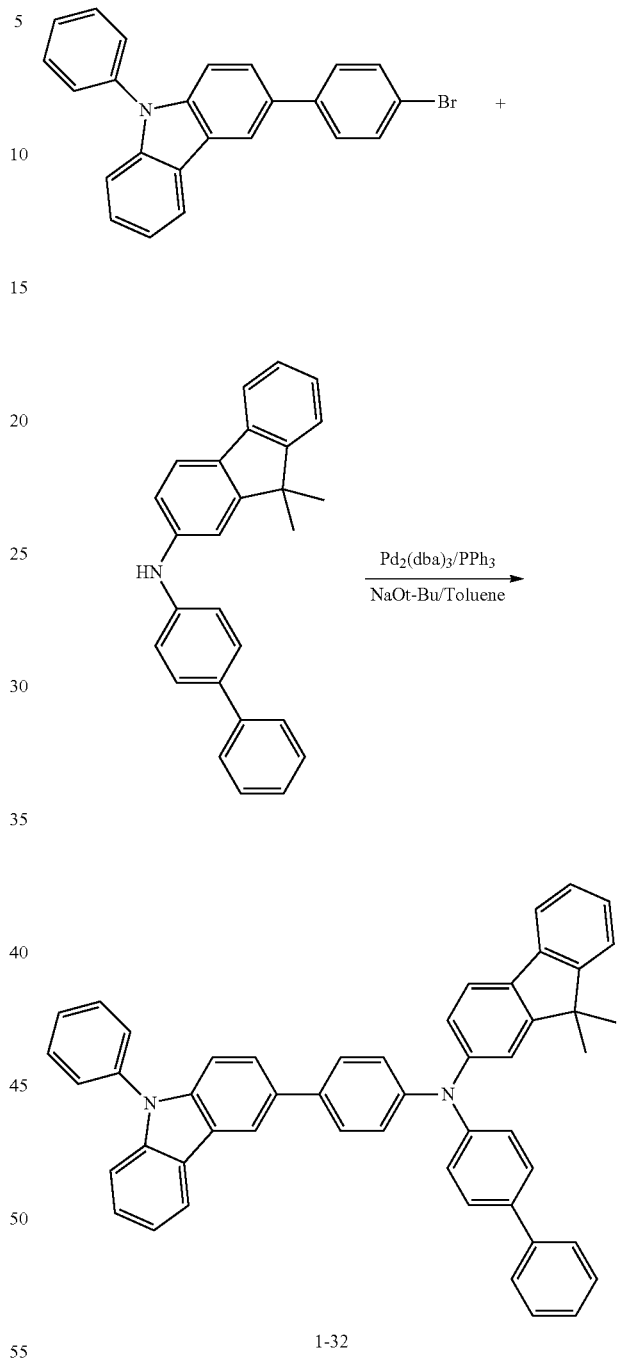

After dissolving 9-(4'-bromo-[1,1'-biphenyl]-4-yl)-9H-carbazole (9.6 g, 24 mmol) in toluene, di([1,1'-biphenyl]-4-yl)amine (6.4 g, 20 mmol), Pd$_2$(dba)$_3$ (0.05 eq.), PPh$_3$ (0.1 eq.) and NaOt-Bu (3 eq.) were added, and then the mixture was refluxed with stirring at 100□ for 24 hours. Upon the completion of the reaction, a reaction product was extracted with ether and water. The organic layer was dried with MgSO$_4$ and concentrated. The concentrate was separated by silica gel column chromatography and recrystallization, whereby a final product was obtained in the amount of 12.9 g (yield: 84%).

After dissolving 3-(4-bromophenyl)-9-phenyl-9H-carbazole (9.6 g, 24 mmol) in toluene, N-([1,1'-biphenyl]-4-yl)-9,9-dimethyl-9H-fluoren-2-amine (7.2 g, 20 mmol), Pd$_2$(dba)$_3$ (0.05 eq.), PPh$_3$ (0.1 eq.) and NaOt-Bu (3 eq.) were added, and then the mixture was refluxed with stirring at 100□ for 24 hours. Upon the completion of the reaction, a reaction product was extracted with ether and water. The organic layer was dried with MgSO$_4$ and concentrated. The concentrate was separated by silica gel column chromatography and recrystallization, whereby a final product was obtained in the amount of 13.8 g (yield: 85%).

(3) Synthesis Example of Compound 1-61

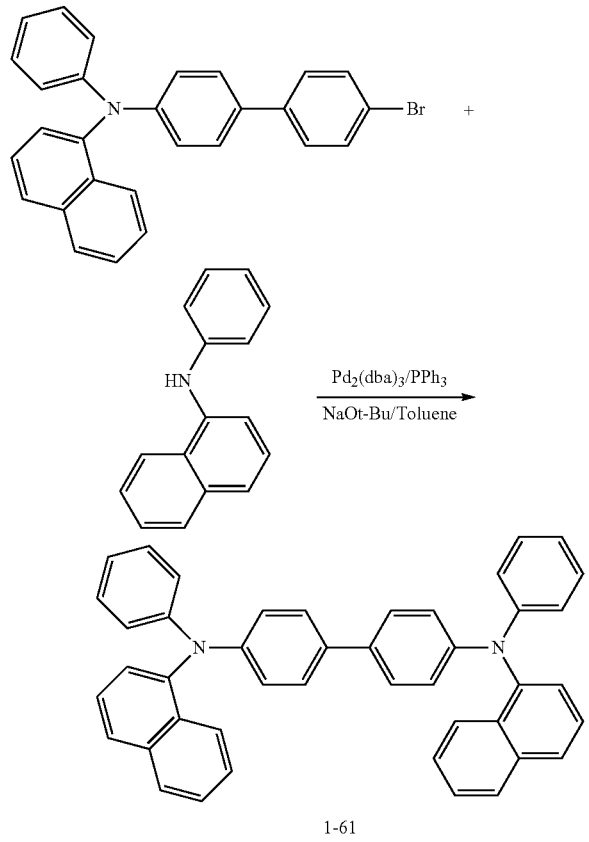

1-61

After dissolving N-(4'-bromo-[1,1'-biphenyl]-4-yl)-N-phenylnaphthalen-1-amine (10.8 g, 24 mmol) in toluene, N-phenylnaphthalen-1-amine (4.4 g, 20 mmol), Pd$_2$(dba)$_3$ (0.05 eq.), PPh$_3$ (0.1 eq.), NaOt-Bu (3 eq.) were added, and then the mixture was refluxed with stirring at 100□ for 24 hours. Upon the completion of the reaction, a reaction product was extracted with ether and water. The organic layer was dried with MgSO$_4$ and concentrated. The concentrate was separated by silica gel column chromatography and recrystallization, whereby a final product was obtained in the amount of 11.4 g (yield: 81%).

Meanwhile, Table 4 below shows FD-MS data of final products included in Formula 7 synthesized according to the above synthesis.

Fabrication and Evaluation of Organic Electronic Element

[Example (1)] Green OLED

First, an ITO layer (anode) was formed on a glass substrate, and then N$^1$-(naphthalen-2-yl)-N$^4$,N$^4$-bis(4-(naphthalen-2-yl(phenyl)amino)phenyl)-N$^1$-phenylbenzene-1,4-diamine (hereinafter, "2-TNATA") was vacuum-deposited on the ITO layer to form a hole injection layer with a thickness of 60 nm.

Subsequently, compound 1-17 of the present invention as compound of a hole transport layer was vacuum-deposited with a thickness of 60 nm on the hole injection layer to form a hole transport layer.

Next, compound P-1 as compound of an emission-auxiliary layer was vacuum-deposited with a thickness of 20 nm on the hole transport layer to form an emission-auxiliary layer.

Next, a light emitting layer with a thickness of 30 nm was formed on the emission-auxiliary layer by using 4,4'-N,N'-dicarbazole-biphenyl (hereinafter, "CBP") as host material and tris(2-phenylpyridine)-iridium (hereinafter, "Ir(ppy)$_3$)") as dopant material in a weight ratio of 95:5.

Next, a film of ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and a film of tris(8-quinolinolato)aluminum (hereinafter, "Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example (2)] to [Example (36)] Green OLED

The OLEDs were each manufactured in the same manner as described in Example (1) except that any one of the compounds P-2 to P-36 listed in Table 5 below was used as an emission-auxiliary layer material, instead of the inventive compound P-1.

[Example (37)] to [Example (72)] Green OLED

The OLEDs were each manufactured in the same manner as described in Example (1) except that compound 1-32 instead of the inventive compound 1-17 was used as a hole transport layer material and any one of compounds P-1 to

TABLE 4

| Compound | FD-MS | Compound | FD-MS |
| --- | --- | --- | --- |
| 1-17 | m/z = 638.27 (C$_{48}$H$_{34}$N$_2$ = 638.80) | 1-20 | m/z = 678.30 (C$_{51}$H$_{38}$N$_2$ = 678.86) |
| 1-21 | m/z = 802.33 (C$_{61}$H$_{42}$N$_2$ = 803.00) | 1-22 | m/z = 800.30 (C$_{61}$H$_{40}$N$_2$ = 800.98) |
| 1-32 | m/z = 678.30 (C$_{51}$H$_{38}$N$_2$ = 678.86) | 1-33 | m/z = 802.33 (C$_{61}$H$_{42}$N$_2$ = 803.00) |
| 1-34 | m/z = 800.32 (C$_{61}$H$_{40}$N$_2$ = 800.98) | 1-43 | m/z = 714.30 (C$_{54}$H$_{38}$N$_2$ = 714.89) |
| 1-44 | m/z = 754.33 (C$_{57}$H$_{42}$N$_2$ = 754.96) | 1-45 | m/z = 878.37 (C$_{67}$H$_{46}$N$_2$ = 879.10) |
| 1-46 | m/z = 876.35 (C$_{67}$H$_{44}$N$_2$ = 877.08) | 1-47 | m/z = 744.26 (C$_{54}$H$_{36}$N$_2$S = 744.94) |
| 1-52 | m/z = 826.33 (C$_{63}$H$_{42}$N$_2$ = 827.02) | 1-53 | m/z = 824.32 (C$_{63}$H$_{40}$N$_2$ = 825.01) |
| 1-54 | m/z = 688.29 (C$_{52}$H$_{36}$N$_2$ = 688.86) | 1-55 | m/z = 728.32 (C$_{55}$H$_{40}$N$_2$ = 728.92) |
| 1-57 | m/z = 778.33 (C$_{59}$H$_{42}$N$_2$ = 778.98) | 1-58 | m/z = 902.37 (C$_{69}$H$_{46}$N$_2$ = 903.12) |
| 1-59 | m/z = 900.53 (C$_{69}$H$_{44}$N$_2$ = 901.10) | 1-60 | m/z = 538.24 (C$_{40}$H$_{30}$N$_2$ = 538.68) |
| 1-61 | m/z = 588.26 (C$_{44}$H$_{82}$N$_2$ = 588.74) | 1-62 | m/z = 586.26 (C$_{44}$H$_{32}$N$_2$ = 588.74) |
| 1-63 | m/z = 614.27 (C$_{40}$H$_{34}$N$_2$ = 614.78) | | |

P-36 listed in Table below was used as an emission-auxiliary layer material instead of the inventive compound P-1.

[Example (73)] to [Example (108)] Green OLED

The OLEDs were each manufactured in the same manner as described in Example (1) except that compound 1-61 instead of the inventive compound 1-17 was used as a hole transport layer material and any one of the P-1 to P-36 listed in Table 5 below was used as an emission-auxiliary layer material instead of the inventive compound P-1.

[Comparative Example (1)] to [Example (3)] Green OLED

The OLEDs were each manufactured in the same manner as described in Example (1) except that any one of compounds 1-17, 1-32 and 1-61 was used as a hole transport layer material and an emission-auxiliary layer was not formed.

A forward bias DC voltage was applied to each of the OLEDs manufactured through the Examples (1) to (108) and the Comparative Examples (1) to (3), and electro-luminescence (EL) characteristics of the OLED were measured by PR-650 (Photoresearch). Also, T95 life span was measured by life span measuring equipment (Mcscience) at reference brightness of 5000 cd/m². Evaluation results are given in the Table 5 below.

TABLE 5

| | HTL com. | EAL com. | Voltage (V) | Current Density (mA/cm²) | Brightness (cd/m²) | Efficiency (cd/A) | Lifetime T(95) |
|---|---|---|---|---|---|---|---|
| comp.Ex(1) | Com.(1-17) | — | 6.3 | 16.1 | 5000.0 | 31.0 | 87.9 |
| comp.Ex(2) | Com.(1-32) | — | 5.9 | 13.2 | 5000.0 | 38.0 | 78.4 |
| comp.Ex(3) | Com.(1-61) | — | 6.5 | 21.7 | 5000.0 | 23.0 | 61.9 |
| Ex.(1) | Com.(1-17) | Com.(P-1) | 6.3 | 10.2 | 5000.0 | 49.2 | 137.9 |
| Ex.(2) | Com.(1-17) | Com.(P-2) | 6.4 | 10.6 | 5000.0 | 47.4 | 149.3 |
| Ex.(3) | Com.(1-17) | Com.(P-3) | 6.4 | 11.0 | 5000.0 | 45.4 | 107.1 |
| Ex.(4) | Com.(1-17) | Com.(P-4) | 6.3 | 12.2 | 5000.0 | 41.0 | 135.9 |
| Ex.(5) | Com.(1-17) | Com.(P-5) | 6.4 | 11.1 | 5000.0 | 45.0 | 96.3 |
| Ex.(6) | Com.(1-17) | Com.(P-6) | 6.4 | 11.5 | 5000.0 | 43.3 | 138.4 |
| Ex.(7) | Com.(1-17) | Com.(P-7) | 6.4 | 11.9 | 5000.0 | 42.1 | 119.9 |
| Ex.(8) | Com.(1-17) | Com.(P-8) | 6.3 | 12.1 | 5000.0 | 41.2 | 108.3 |
| Ex.(9) | Com.(1-17) | Com.(P-9) | 6.2 | 11.3 | 5000.0 | 44.4 | 100.6 |
| Ex.(10) | Com.(1-17) | Com.(P-10) | 6.5 | 10.8 | 5000.0 | 46.1 | 147.6 |
| Ex.(11) | Com.(1-17) | Com.(P-11) | 6.4 | 11.1 | 5000.0 | 45.2 | 98.2 |
| Ex.(12) | Com.(1-17) | Com.(P-12) | 6.3 | 10.7 | 5000.0 | 46.6 | 130.4 |
| Ex.(13) | Com.(1-17) | Com.(P-13) | 6.3 | 10.2 | 5000.0 | 48.9 | 141.2 |
| Ex.(14) | Com.(1-17) | Com.(P-14) | 6.3 | 11.7 | 5000.0 | 42.7 | 100.9 |
| Ex.(15) | Com.(1-17) | Com.(P-15) | 6.4 | 11.6 | 5000.0 | 43.2 | 138.7 |
| Ex.(16) | Com.(1-17) | Com.(P-16) | 6.3 | 11.8 | 5000.0 | 42.2 | 132.7 |
| Ex.(17) | Com.(1-17) | Com.(P-17) | 6.3 | 11.1 | 5000.0 | 45.0 | 115.1 |
| Ex.(18) | Com.(1-17) | Com.(P-18) | 6.4 | 12.1 | 5000.0 | 41.5 | 127.6 |
| Ex.(19) | Com.(1-17) | Com.(P-19) | 6.2 | 10.0 | 5000.0 | 50.0 | 145.0 |
| Ex.(20) | Com.(1-17) | Com.(P-20) | 6.5 | 10.1 | 5000.0 | 49.5 | 104.1 |
| Ex.(21) | Com.(1-17) | Com.(P-21) | 6.3 | 10.5 | 5000.0 | 47.5 | 129.8 |
| Ex.(22) | Com.(1-17) | Com.(P-22) | 6.5 | 11.2 | 5000.0 | 44.5 | 131.3 |
| Ex.(23) | Com.(1-17) | Com.(P-23) | 6.3 | 10.4 | 5000.0 | 47.9 | 126.3 |
| Ex.(24) | Com.(1-17) | Com.(P-24) | 6.5 | 11.2 | 5000.0 | 44.7 | 97.4 |
| Ex.(25) | Com.(1-17) | Com.(P-25) | 6.4 | 11.5 | 5000.0 | 43.6 | 144.2 |
| Ex.(26) | Com.(1-17) | Com.(P-26) | 6.5 | 12.5 | 5000.0 | 40.2 | 100.7 |
| Ex.(27) | Com.(1-17) | Com.(P-27) | 6.3 | 11.5 | 5000.0 | 43.4 | 92.9 |
| Ex.(28) | Com.(1-17) | Com.(P-28) | 6.3 | 10.9 | 5000.0 | 45.9 | 133.5 |
| Ex.(29) | Com.(1-17) | Com.(P-29) | 6.4 | 11.1 | 5000.0 | 45.1 | 131.3 |
| Ex.(30) | Com.(1-17) | Com.(P-30) | 6.4 | 10.1 | 5000.0 | 49.6 | 142.0 |
| Ex.(31) | Com.(1-17) | Com.(P-31) | 6.5 | 10.4 | 5000.0 | 47.9 | 132.9 |
| Ex.(32) | Com.(1-17) | Com.(P-32) | 6.5 | 11.2 | 5000.0 | 44.5 | 91.0 |
| Ex.(33) | Com.(1-17) | Com.(P-33) | 6.5 | 12.2 | 5000.0 | 40.9 | 139.0 |
| Ex.(34) | Com.(1-17) | Com.(P-34) | 6.4 | 11.8 | 5000.0 | 42.3 | 94.5 |
| Ex.(35) | Com.(1-17) | Com.(P-35) | 6.4 | 10.5 | 5000.0 | 47.7 | 147.5 |
| Ex.(36) | Com.(1-17) | Com.(P-36) | 6.4 | 10.8 | 5000.0 | 46.5 | 124.4 |
| Ex.(37) | Com.(1-32) | Com.(P-1) | 6.0 | 9.8 | 5000.0 | 51.1 | 146.2 |
| Ex.(38) | Com.(1-32) | Com.(P-2) | 5.9 | 9.6 | 5000.0 | 52.3 | 132.0 |
| Ex.(39) | Com.(1-32) | Com.(P-3) | 5.9 | 10.0 | 5000.0 | 50.2 | 124.6 |
| Ex.(40) | Com.(1-32) | Com.(P-4) | 6.0 | 11.0 | 5000.0 | 45.5 | 98.2 |
| Ex.(41) | Com.(1-32) | Com.(P-5) | 5.8 | 10.3 | 5000.0 | 48.6 | 130.9 |
| Ex.(42) | Com.(1-32) | Com.(P-6) | 5.8 | 11.1 | 5000.0 | 45.2 | 105.8 |
| Ex.(43) | Com.(1-32) | Com.(P-7) | 6.0 | 10.9 | 5000.0 | 45.7 | 111.4 |
| Ex.(44) | Com.(1-32) | Com.(P-8) | 6.0 | 10.6 | 5000.0 | 47.2 | 147.1 |
| Ex.(45) | Com.(1-32) | Com.(P-9) | 5.9 | 10.3 | 5000.0 | 48.7 | 97.8 |
| Ex.(46) | Com.(1-32) | Com.(P-10) | 6.0 | 9.9 | 5000.0 | 50.4 | 138.0 |
| Ex.(47) | Com.(1-32) | Com.(P-11) | 6.0 | 9.8 | 5000.0 | 50.9 | 125.8 |
| Ex.(48) | Com.(1-32) | Com.(P-12) | 5.9 | 9.8 | 5000.0 | 51.1 | 136.9 |
| Ex.(49) | Com.(1-32) | Com.(P-13) | 5.8 | 10.4 | 5000.0 | 48.2 | 144.7 |
| Ex.(50) | Com.(1-32) | Com.(P-14) | 5.9 | 10.7 | 5000.0 | 46.6 | 119.2 |
| Ex.(51) | Com.(1-32) | Com.(P-15) | 6.0 | 10.3 | 5000.0 | 48.4 | 129.8 |
| Ex.(52) | Com.(1-32) | Com.(P-16) | 5.9 | 10.2 | 5000.0 | 49.2 | 128.8 |
| Ex.(53) | Com.(1-32) | Com.(P-17) | 6.0 | 10.8 | 5000.0 | 46.4 | 104.0 |

TABLE 5-continued

| | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| Ex.(54) | Com.(1-32) | Com.(P-18) | 5.9 | 10.7 | 5000.0 | 46.9 | 111.8 |
| Ex.(55) | Com.(1-32) | Com.(P-19) | 5.9 | 8.9 | 5000.0 | 56.3 | 151.0 |
| Ex.(56) | Com.(1-32) | Com.(P-20) | 5.8 | 9.3 | 5000.0 | 53.7 | 91.6 |
| Ex.(57) | Com.(1-32) | Com.(P-21) | 5.8 | 9.9 | 5000.0 | 50.4 | 134.6 |
| Ex.(58) | Com.(1-32) | Com.(P-22) | 6.0 | 10.0 | 5000.0 | 50.0 | 98.2 |
| Ex.(59) | Com.(1-32) | Com.(P-23) | 5.8 | 9.1 | 5000.0 | 54.7 | 97.9 |
| Ex.(60) | Com.(1-32) | Com.(P-24) | 6.0 | 10.9 | 5000.0 | 45.7 | 96.3 |
| Ex.(61) | Com.(1-32) | Com.(P-25) | 5.9 | 10.1 | 5000.0 | 49.5 | 119.9 |
| Ex.(62) | Com.(1-32) | Com.(P-26) | 6.0 | 10.1 | 5000.0 | 49.4 | 94.4 |
| Ex.(63) | Com.(1-32) | Com.(P-27) | 5.8 | 10.5 | 5000.0 | 47.8 | 121.8 |
| Ex.(64) | Com.(1-32) | Com.(P-28) | 5.9 | 9.3 | 5000.0 | 53.7 | 137.4 |
| Ex.(65) | Com.(1-32) | Com.(P-29) | 5.9 | 9.1 | 5000.0 | 54.7 | 145.9 |
| Ex.(66) | Com.(1-32) | Com.(P-30) | 5.8 | 9.1 | 5000.0 | 54.8 | 94.7 |
| Ex.(67) | Com.(1-32) | Com.(P-31) | 6.0 | 9.9 | 5000.0 | 50.3 | 124.5 |
| Ex.(68) | Com.(1-32) | Com.(P-32) | 5.9 | 10.8 | 5000.0 | 46.3 | 120.1 |
| Ex.(69) | Com.(1-32) | Com.(P-33) | 5.8 | 10.5 | 5000.0 | 47.6 | 95.4 |
| Ex.(70) | Com.(1-32) | Com.(P-34) | 5.8 | 11.1 | 5000.0 | 45.2 | 96.6 |
| Ex.(71) | Com.(1-32) | Com.(P-35) | 5.9 | 9.3 | 5000.0 | 53.9 | 93.0 |
| Ex.(72) | Com.(1-32) | Com.(P-36) | 5.8 | 9.3 | 5000.0 | 53.8 | 144.8 |
| Ex.(73) | Com.(1-61) | Com.(P-1) | 6.4 | 12.9 | 5000.0 | 38.7 | 110.5 |
| Ex.(74) | Com.(1-61) | Com.(P-2) | 6.4 | 12.8 | 5000.0 | 39.0 | 117.3 |
| Ex.(75) | Com.(1-61) | Com.(P-3) | 6.5 | 13.1 | 5000.0 | 38.2 | 111.7 |
| Ex.(76) | Com.(1-61) | Com.(P-4) | 6.6 | 14.4 | 5000.0 | 34.8 | 100.3 |
| Ex.(77) | Com.(1-61) | Com.(P-5) | 6.4 | 14.9 | 5000.0 | 33.5 | 107.2 |
| Ex.(78) | Com.(1-61) | Com.(P-6) | 6.6 | 14.5 | 5000.0 | 34.6 | 111.5 |
| Ex.(79) | Com.(1-61) | Com.(P-7) | 6.6 | 14.9 | 5000.0 | 33.5 | 90.3 |
| Ex.(80) | Com.(1-61) | Com.(P-8) | 6.5 | 14.8 | 5000.0 | 33.8 | 113.8 |
| Ex.(81) | Com.(1-61) | Com.(P-9) | 6.5 | 14.9 | 5000.0 | 33.5 | 115.4 |
| Ex.(82) | Com.(1-61) | Com.(P-10) | 6.6 | 12.6 | 5000.0 | 39.7 | 99.5 |
| Ex.(83) | Com.(1-61) | Com.(P-11) | 6.7 | 14.3 | 5000.0 | 35.1 | 118.9 |
| Ex.(84) | Com.(1-61) | Com.(P-12) | 6.5 | 13.4 | 5000.0 | 37.4 | 92.1 |
| Ex.(85) | Com.(1-61) | Com.(P-13) | 6.5 | 15.0 | 5000.0 | 33.3 | 116.9 |
| Ex.(86) | Com.(1-61) | Com.(P-14) | 6.5 | 14.7 | 5000.0 | 34.0 | 118.8 |
| Ex.(87) | Com.(1-61) | Com.(P-15) | 6.5 | 15.1 | 5000.0 | 33.1 | 97.2 |
| Ex.(88) | Com.(1-61) | Com.(P-16) | 6.6 | 14.7 | 5000.0 | 34.0 | 114.3 |
| Ex.(89) | Com.(1-61) | Com.(P-17) | 6.6 | 14.7 | 5000.0 | 34.1 | 104.0 |
| Ex.(90) | Com.(1-61) | Com.(P-18) | 6.6 | 14.8 | 5000.0 | 33.7 | 116.5 |
| Ex.(91) | Com.(1-61) | Com.(P-19) | 6.6 | 11.6 | 5000.0 | 43.0 | 124.0 |
| Ex.(92) | Com.(1-61) | Com.(P-20) | 6.4 | 13.1 | 5000.0 | 38.1 | 105.3 |
| Ex.(93) | Com.(1-61) | Com.(P-21) | 6.6 | 13.9 | 5000.0 | 35.9 | 95.4 |
| Ex.(94) | Com.(1-61) | Com.(P-22) | 6.5 | 14.5 | 5000.0 | 34.6 | 114.4 |
| Ex.(95) | Com.(1-61) | Com.(P-23) | 6.7 | 14.1 | 5000.0 | 35.4 | 116.2 |
| Ex.(96) | Com.(1-61) | Com.(P-24) | 6.4 | 14.9 | 5000.0 | 33.7 | 100.0 |
| Ex.(97) | Com.(1-61) | Com.(P-25) | 6.5 | 15.1 | 5000.0 | 33.1 | 110.3 |
| Ex.(98) | Com.(1-61) | Com.(P-26) | 6.6 | 15.1 | 5000.0 | 33.2 | 97.2 |
| Ex.(99) | Com.(1-61) | Com.(P-27) | 6.6 | 14.4 | 5000.0 | 34.6 | 109.6 |
| Ex.(100) | Com.(1-61) | Com.(P-28) | 6.5 | 12.6 | 5000.0 | 39.6 | 97.1 |
| Ex.(101) | Com.(1-61) | Com.(P-29) | 6.6 | 13.3 | 5000.0 | 37.7 | 98.7 |
| Ex.(102) | Com.(1-61) | Com.(P-30) | 6.7 | 13.7 | 5000.0 | 36.4 | 94.4 |
| Ex.(103) | Com.(1-61) | Com.(P-31) | 6.5 | 13.4 | 5000.0 | 37.5 | 116.3 |
| Ex.(104) | Com.(1-61) | Com.(P-32) | 6.6 | 15.1 | 5000.0 | 33.0 | 90.9 |
| Ex.(105) | Com.(1-61) | Com.(P-33) | 6.6 | 15.1 | 5000.0 | 33.1 | 96.1 |
| Ex.(106) | Com.(1-61) | Com.(P-34) | 6.6 | 14.4 | 5000.0 | 34.8 | 111.8 |
| Ex.(107) | Com.(1-61) | Com.(P-35) | 6.5 | 12.6 | 5000.0 | 39.7 | 108.7 |
| Ex.(108) | Com.(1-61) | Com.(P-36) | 6.7 | 12.8 | 5000.0 | 39.1 | 118.4 |

[Example (109)] Blue OLED

First, an ITO layer (anode) was formed on a glass substrate, and then 2-TNATA was vacuum-deposited on the ITO layer to form a hole injection layer with a thickness of 60 nm.

Subsequently, compound P1-17 of the present invention as compound of a hole transport layer was vacuum-deposited with a thickness of 60 nm on the hole injection layer to form a hole transport layer.

Next, compound P-1 as compound of an emission-auxiliary layer was vacuum-deposited with a thickness of 20 nm on the hole transport layer to form an emission-auxiliary layer.

Next, a light emitting layer with a thickness of 30 nm was formed on the emission-auxiliary layer by using 9,10-di(naphthalen-2-yl)anthracene as host material and BD-052X (Idemitsu kosan) as dopant material in a weight ratio of 96:4.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example (110)] to [Example (124)] Blue OLED

The OLEDs were each manufactured in the same manner as described in Example (109) except that any one of the P-2, P-3, P-10 to P-12, P-19 to P-21, P-23, P-28 to P-31, P-35 and P-36 listed in Table 6 below was used as an emission-auxiliary layer material, instead of the inventive compound P-1.

[Example (125)] to [Example (140)] Blue OLED

The OLEDs were each manufactured in the same manner as described in Example (109) except that compound 1-32 instead of the inventive compound 1-17 was used as a hole transport layer material and any one of the P-1 to P-3, P-10 to P-12, P-19 to P-21, P-23, P-28 to P-31, P-35 and P-36 listed in Table below was used as an emission-auxiliary layer material instead of the inventive compound P-1.

[Example (141)] to [Example (156)] Blue OLED

The OLEDs were each manufactured in the same manner as described in Example (109) except that compound 1-61 instead of the inventive compound 1-17 was used as a hole transport layer material and any one of the P-1 to P-3, P-10 to P-12, P-19 to P-21, P-23, P-28 to P-31, P-35 and P-36 listed in Table below was used as an emission-auxiliary layer material instead of the inventive compound P-1.

[Comparative Example (4)] to [Example (6)] Blue OLED

The OLEDs were each manufactured in the same manner as described in Example (109) except that any one of compounds 1-17, 1-32 and 1-61 was used as a hole transport layer material and an emission-auxiliary layer was not formed.

A forward bias DC voltage was applied to each of the OLEDs manufactured through the Examples (109) to (156) and the Comparative Examples (4) to (6), and electroluminescence (EL) characteristics of the OLED were measured by PR-650 (Photoresearch). Also, T95 life span was measured by life span measuring equipment (Mcscience) at reference brightness of 5000 cd/m$^2$. Evaluation results are given in the Table 6 below.

TABLE 6

| | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| comp.Ex(4) | Com.(1-17) | — | 4.8 | 11.6 | 500.0 | 4.3 | 91.7 |
| comp.Ex(5) | Com.(1-32) | — | 4.3 | 9.6 | 500.0 | 5.2 | 93.7 |
| comp.Ex(6) | Com.(1-61) | — | 5.3 | 13.5 | 500.0 | 3.7 | 85.3 |
| Ex.(109) | Com.(1-17) | Com.(P-1) | 4.9 | 9.0 | 500.0 | 5.5 | 112.2 |
| Ex.(110) | Com.(1-17) | Com.(P-2) | 4.8 | 9.3 | 500.0 | 5.4 | 131.3 |
| Ex.(111) | Com.(1-17) | Com.(P-3) | 4.8 | 8.4 | 500.0 | 6.0 | 120.0 |
| Ex.(112) | Com.(1-17) | Com.(P-10) | 4.7 | 9.4 | 500.0 | 5.3 | 136.8 |
| Ex.(113) | Com.(1-17) | Com.(P-11) | 4.8 | 7.9 | 500.0 | 6.3 | 123.2 |
| Ex.(114) | Com.(1-17) | Com.(P-12) | 4.7 | 8.9 | 500.0 | 5.6 | 125.5 |
| Ex.(115) | Com.(1-17) | Com.(P-19) | 4.7 | 6.7 | 500.0 | 7.5 | 149.9 |
| Ex.(116) | Com.(1-17) | Com.(P-20) | 4.9 | 7.5 | 500.0 | 6.6 | 115.8 |
| Ex.(117) | Com.(1-17) | Com.(P-21) | 4.8 | 8.7 | 500.0 | 5.8 | 138.5 |
| Ex.(118) | Com.(1-17) | Com.(P-23) | 4.7 | 9.8 | 500.0 | 5.1 | 110.0 |
| Ex.(119) | Com.(1-17) | Com.(P-28) | 4.8 | 9.2 | 500.0 | 5.4 | 104.9 |
| Ex.(120) | Com.(1-17) | Com.(P-29) | 4.8 | 9.8 | 500.0 | 5.1 | 109.0 |
| Ex.(121) | Com.(1-17) | Com.(P-30) | 4.9 | 9.8 | 500.0 | 5.1 | 120.5 |
| Ex.(122) | Com.(1-17) | Com.(P-31) | 4.8 | 7.6 | 500.0 | 6.6 | 96.2 |
| Ex.(123) | Com.(1-17) | Com.(P-35) | 4.7 | 7.6 | 500.0 | 6.6 | 104.1 |
| Ex.(124) | Com.(1-17) | Com.(P-36) | 4.9 | 9.5 | 500.0 | 5.3 | 109.1 |
| Ex.(125) | Com.(1-32) | Com.(P-1) | 4.4 | 7.7 | 500.0 | 6.5 | 113.8 |
| Ex.(126) | Com.(1-32) | Com.(P-2) | 4.3 | 7.3 | 500.0 | 6.8 | 114.1 |
| Ex.(127) | Com.(1-32) | Com.(P-3) | 4.2 | 6.5 | 500.0 | 7.6 | 139.6 |
| Ex.(128) | Com.(1-32) | Com.(P-10) | 4.4 | 6.6 | 500.0 | 7.5 | 147.4 |
| Ex.(129) | Com.(1-32) | Com.(P-11) | 4.4 | 6.6 | 500.0 | 7.6 | 92.0 |
| Ex.(130) | Com.(1-32) | Com.(P-12) | 4.4 | 7.2 | 500.0 | 6.9 | 122.3 |
| Ex.(131) | Com.(1-32) | Com.(P-19) | 4.4 | 6.2 | 500.0 | 8.1 | 148.3 |
| Ex.(132) | Com.(1-32) | Com.(P-20) | 4.3 | 6.3 | 500.0 | 7.9 | 93.6 |
| Ex.(133) | Com.(1-32) | Com.(P-21) | 4.5 | 7.2 | 500.0 | 6.9 | 146.8 |
| Ex.(134) | Com.(1-32) | Com.(P-23) | 4.5 | 7.6 | 500.0 | 6.6 | 106.1 |
| Ex.(135) | Com.(1-32) | Com.(P-28) | 4.3 | 6.9 | 500.0 | 7.2 | 124.2 |
| Ex.(136) | Com.(1-32) | Com.(P-29) | 4.3 | 6.3 | 500.0 | 8.0 | 128.7 |
| Ex.(137) | Com.(1-32) | Com.(P-30) | 4.3 | 6.9 | 500.0 | 7.2 | 138.1 |
| Ex.(138) | Com.(1-32) | Com.(P-31) | 4.4 | 7.0 | 500.0 | 7.1 | 96.4 |
| Ex.(139) | Com.(1-32) | Com.(P-35) | 4.3 | 6.7 | 500.0 | 7.5 | 142.1 |
| Ex.(140) | Com.(1-32) | Com.(P-36) | 4.2 | 7.3 | 500.0 | 6.9 | 131.9 |
| Ex.(141) | Com.(1-61) | Com.(P-1) | 5.2 | 9.5 | 500.0 | 5.3 | 99.3 |
| Ex.(142) | Com.(1-61) | Com.(P-2) | 5.3 | 10.3 | 500.0 | 4.8 | 117.9 |
| Ex.(143) | Com.(1-61) | Com.(P-3) | 5.3 | 8.5 | 500.0 | 5.9 | 126.2 |
| Ex.(144) | Com.(1-61) | Com.(P-10) | 5.3 | 10.5 | 500.0 | 4.8 | 118.9 |
| Ex.(145) | Com.(1-61) | Com.(P-11) | 5.2 | 9.6 | 500.0 | 5.2 | 124.5 |
| Ex.(146) | Com.(1-61) | Com.(P-12) | 5.3 | 9.7 | 500.0 | 5.2 | 106.2 |
| Ex.(147) | Com.(1-61) | Com.(P-19) | 5.3 | 7.9 | 500.0 | 6.3 | 142.1 |
| Ex.(148) | Com.(1-61) | Com.(P-20) | 5.3 | 9.8 | 500.0 | 5.1 | 146.6 |
| Ex.(149) | Com.(1-61) | Com.(P-21) | 5.3 | 11.0 | 500.0 | 4.5 | 92.7 |
| Ex.(150) | Com.(1-61) | Com.(P-23) | 5.4 | 9.2 | 500.0 | 5.5 | 123.1 |
| Ex.(151) | Com.(1-61) | Com.(P-28) | 5.3 | 8.8 | 500.0 | 5.7 | 144.9 |
| Ex.(152) | Com.(1-61) | Com.(P-29) | 5.2 | 9.2 | 500.0 | 5.4 | 141.6 |
| Ex.(153) | Com.(1-61) | Com.(P-30) | 5.3 | 8.6 | 500.0 | 5.8 | 118.5 |
| Ex.(154) | Com.(1-61) | Com.(P-31) | 5.3 | 8.5 | 500.0 | 5.9 | 123.7 |

TABLE 6-continued

| | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| Ex.(155) | Com.(1-61) | Com.(P-35) | 5.3 | 8.6 | 500.0 | 5.8 | 120.4 |
| Ex.(156) | Com.(1-61) | Com.(P-36) | 5.5 | 9.5 | 500.0 | 5.2 | 107.4 |

It can be seen from the results in Tables 5 and 6 above, that Examples of the present employing the inventive compounds represented by Formula 7 as a hole transport layer material and the inventive compounds represented by Formula 1 as an emission-auxiliary layer material showed a similar or slightly increased driving voltage, predominantly improved luminescent efficiency and lifespan, compared to Comparative examples employing the inventive compounds represented by Formula 7 as a hole transport layer material and not forming an emission-auxiliary layer.

Further, the electrical properties of the OLED employing compound 1-32 among compounds 1-17, 1-32 and 1-61 represented by Formula 7 was the most excellent, when compound represented by Formula 1 was employed as an emission-auxiliary layer material or an emission-auxiliary layer was not formed.

This may be caused by the fact that when compound of the present invention is used as a material of an emission-auxiliary layer, an appropriate amount of holes can be efficiently transferred into a light emitting layer from a hole transport layer due to deeper HOMO energy levels which is unique characteristics of the inventive compound, and thus a charge balance of the holes and electrons keeps in the light emitting layer and high T1 prevents electrons from transferring from the light emitting layer resulting in improving color purity and maximizing an efficiency by emitting in interface of a hole transport layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. An organic electric element, comprising:
a first electrode,
a second electrode, and
an organic material layer formed between the first electrode and the second electrode and comprising at least an emission-auxiliary layer and a hole transport layer, wherein the emission-auxiliary layer comprises a compound represented by Formula 1 below,

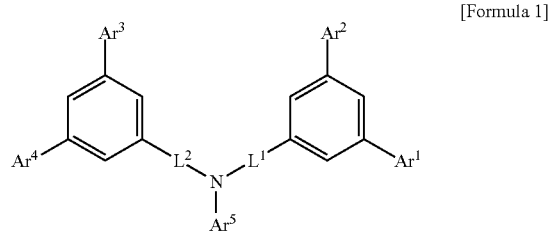

[Formula 1]

wherein, $Ar^1$ to $Ar^5$ are each independently selected from the group consisting of a $C_6$-$C_{24}$ aryl group; a fluorenyl group; a $C_2$-$C_{25}$ heterocyclic group containing at least one heteroatom selected from the group consisting of O, N, S, Si and P; a fused ring formed by a $C_3$-$C_{24}$ aliphatic ring and a $C_6$-$C_{24}$ aromatic ring; a $C_1$-$C_{20}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group and the combination thereof, $L^1$ and $L^2$ are each independently selected from the group consisting of a single bond, a $C_6$-$C_{24}$ arylene group, a fluorenylene group, a $C_2$-$C_{24}$ heterocyclic group containing at least one heteroatom selected from the group consisting of O, N, S, Si, and P, a fused ring formed by a $C_3$-$C_{24}$ aliphatic ring and a $C_6$-$C_{24}$ aromatic ring and the combination thereof, when $Ar^1$ to $Ar^5$ are each independently an aryl group, a fluorenyl group, a heterocyclic group, a fused ring, an alkyl group, an alkenyl group, an alkynyl group, an alkoxy group, or an aryloxy group, each of $Ar^1$ to $Ar^5$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group, and when $L^1$ and $L^2$ are each independently an arylene group, a fluorenylene group, a heterocyclic group or a fused ring, each of $L^1$ and $L^2$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

2. The organic electric element of claim 1, wherein Formula 1 is represented by one of Formulas 2 to 6 below:

<Formula 2>

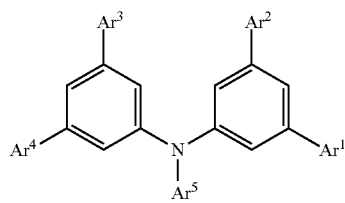

<Formula 3>

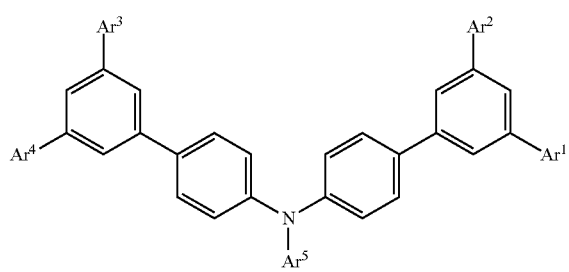

<Formula 4>

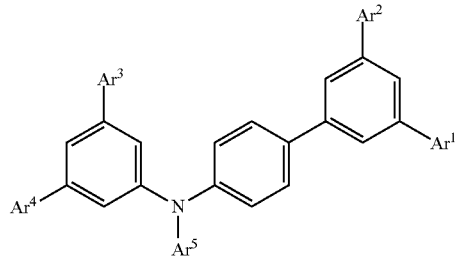

<Formula 5>

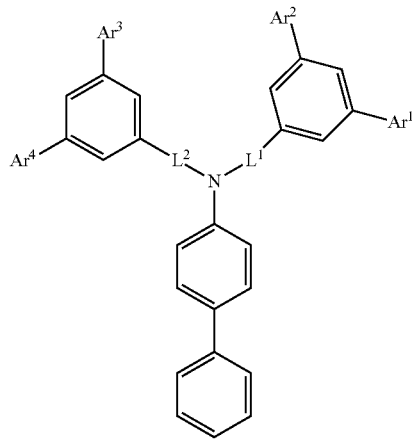

<Formula 6>

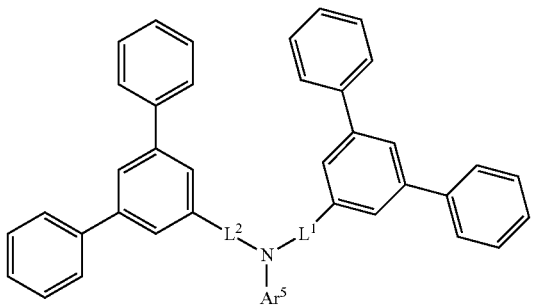

in formulas 2 to 6, $Ar^1$ to $Ar^5$, $L^1$ and $L^2$ are each the same as defined in claim 1.

3. The organic electric element of claim 1, wherein $Ar^1$ to $Ar^5$ are each independently a $C_6$-$C_{12}$ aryl group and both $L^1$ and $L^2$ are a single bond.

4. The organic electric element of claim 1, wherein $Ar^1$ to $Ar^4$ are each phenyl, $Ar^5$ is biphenyl, and $L^1$ and $L^2$ are each independently a single bond or phenylene.

5. The organic electric element of claim 1, wherein the compound represented by Formula 1 is any one of the compounds below:

P-1

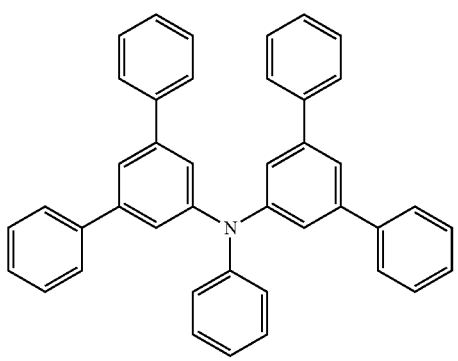

P-2

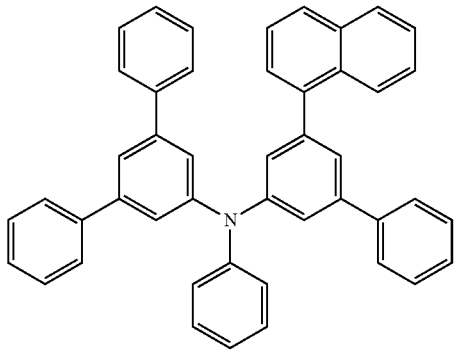

P-3
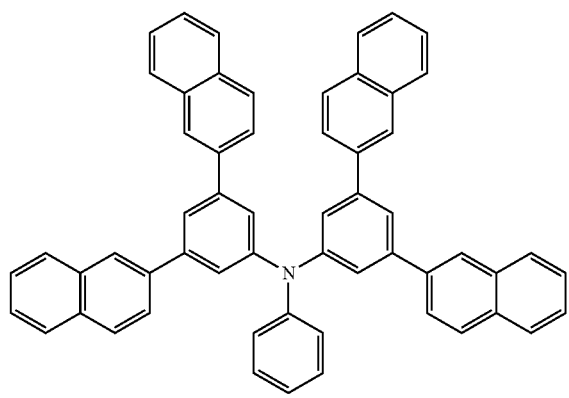
P-6
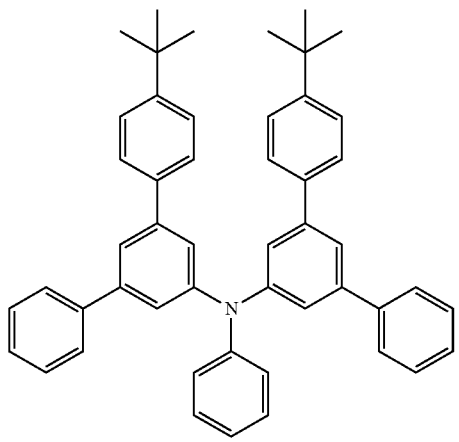
P-4
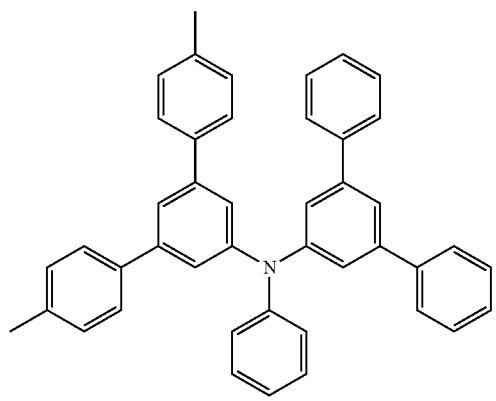
P-7
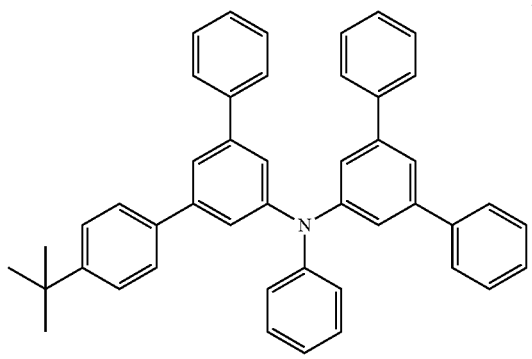
P-5
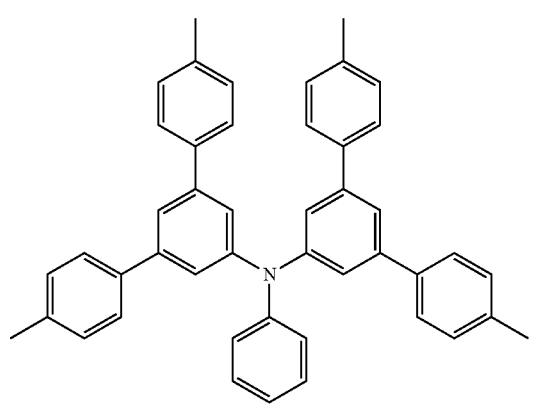
P-8
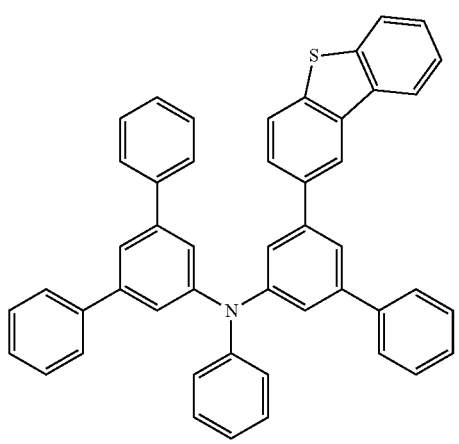

-continued
P-9
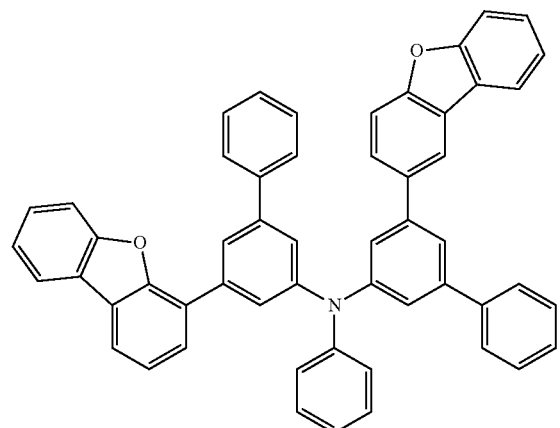
P-10
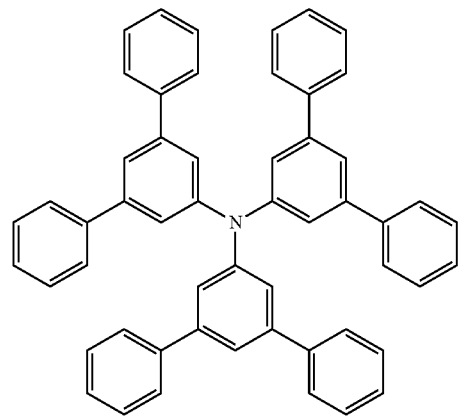
P-11
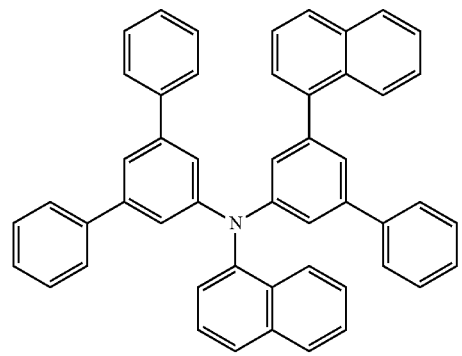
P-12
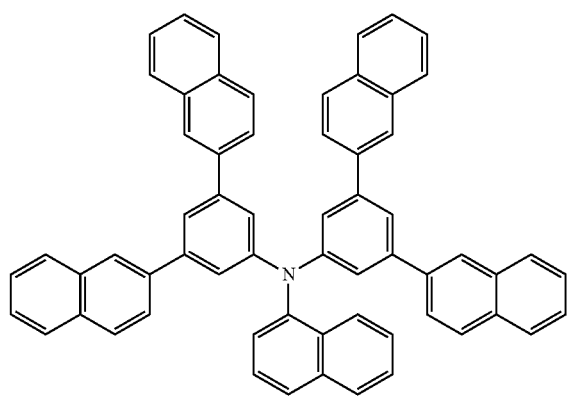
-continued
P-13
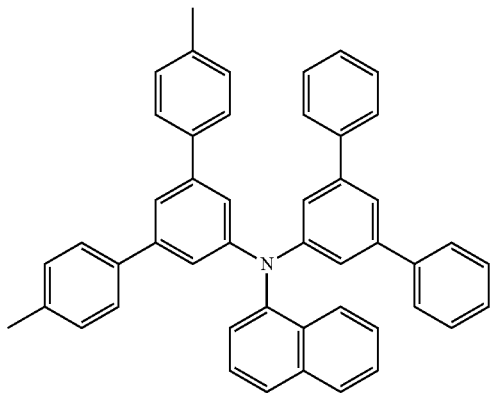
P-14
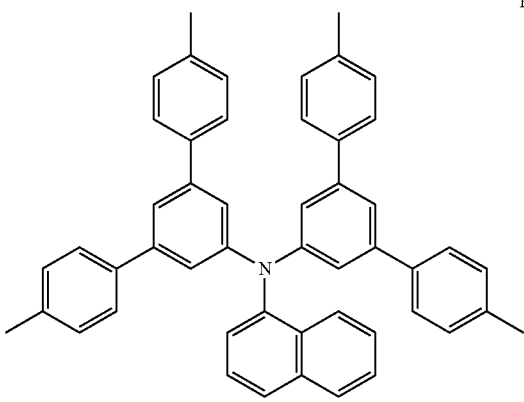
P-15
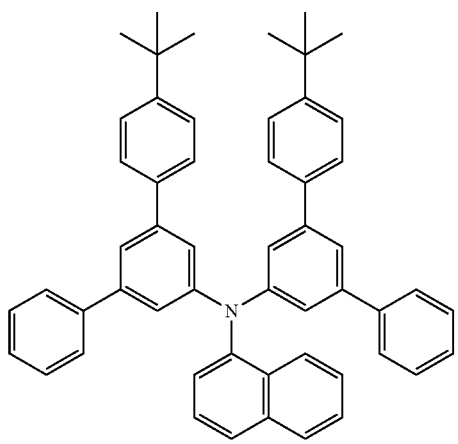

-continued
P-16
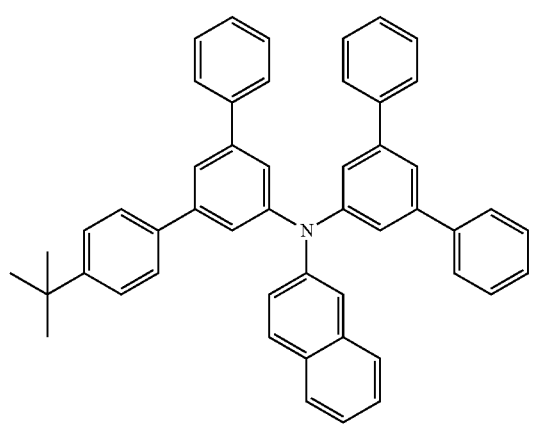
P-17
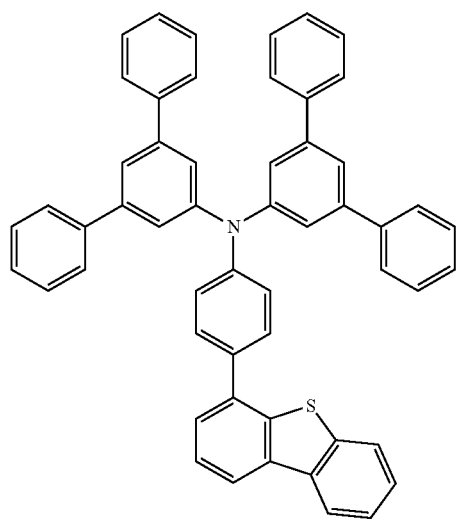
P-18
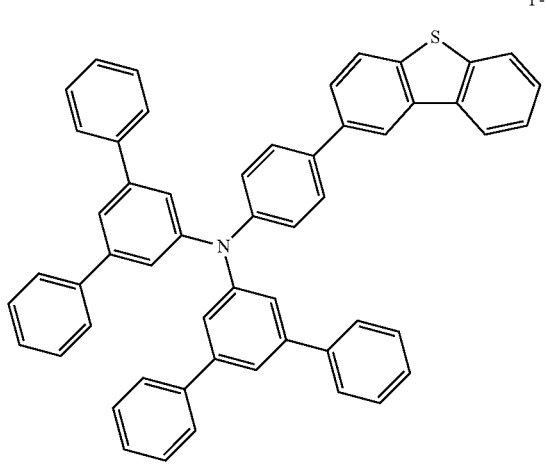
-continued
P-19
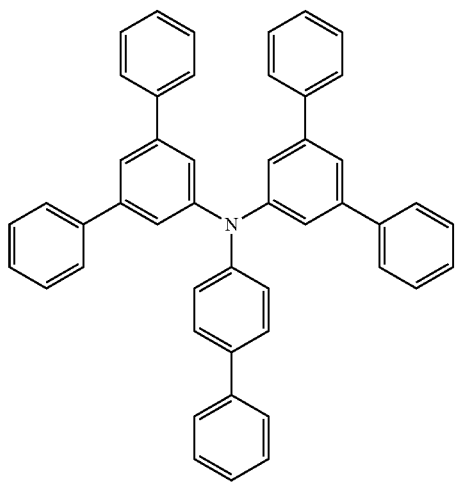
P-20
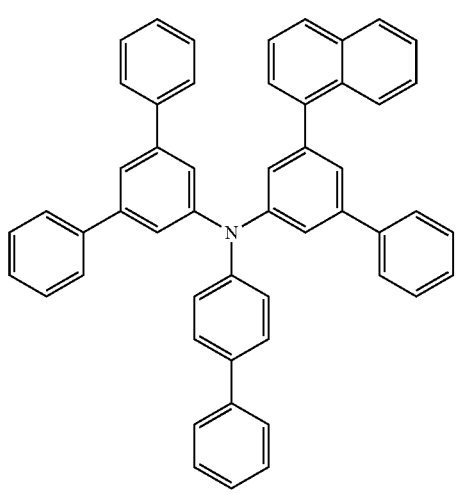
P-21
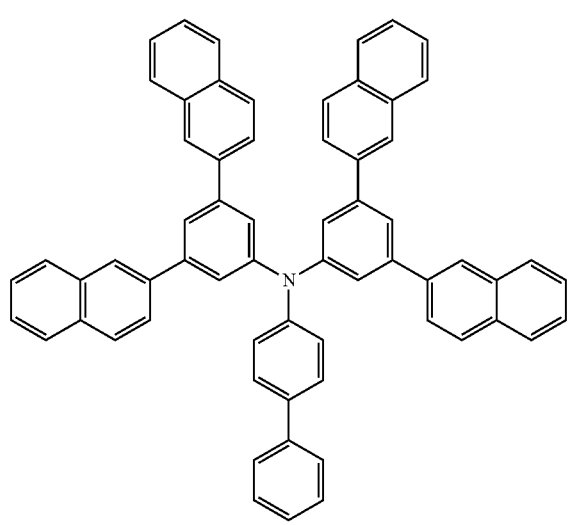

P-22
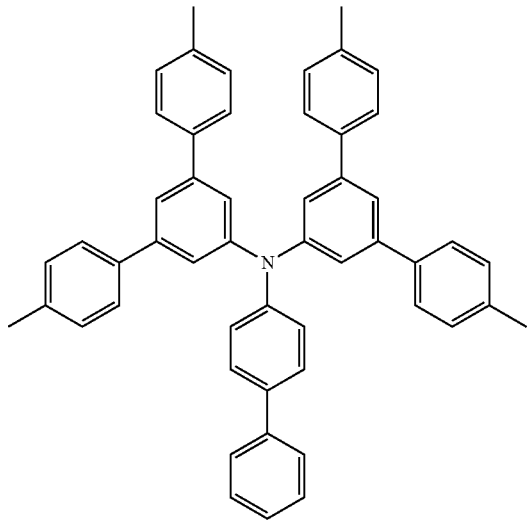
P-25
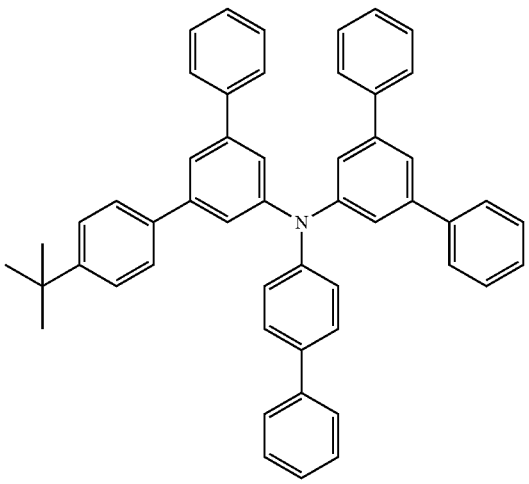
P-23
P-26
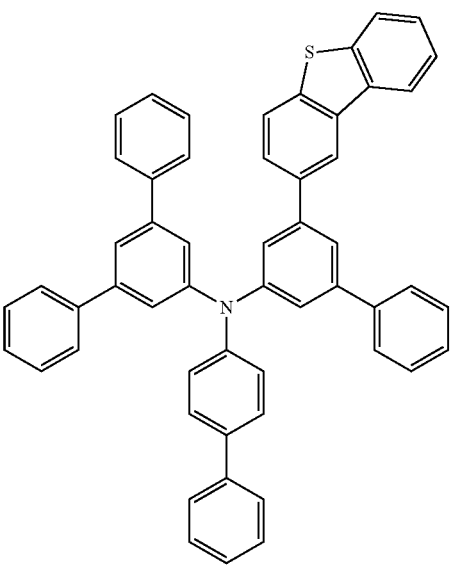
P-24
P-27
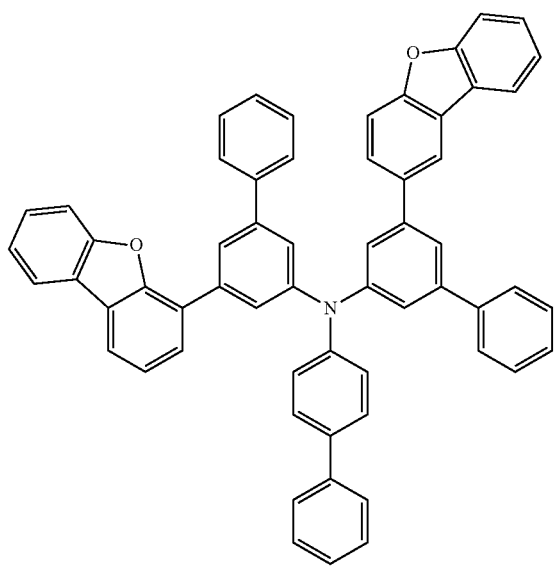

P-28
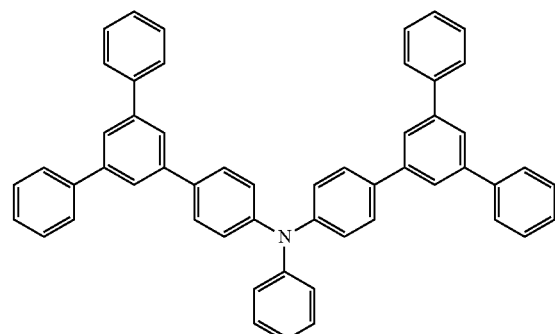
P-29
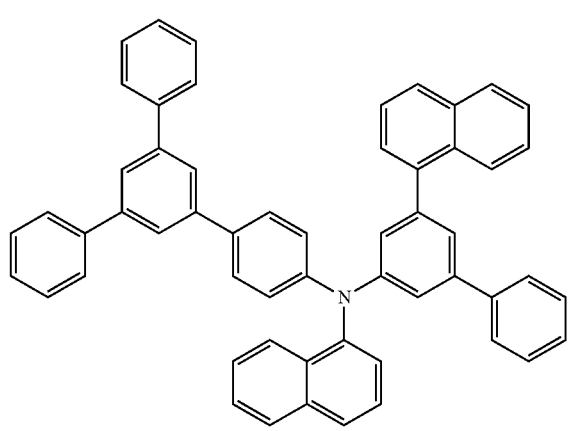
P-30
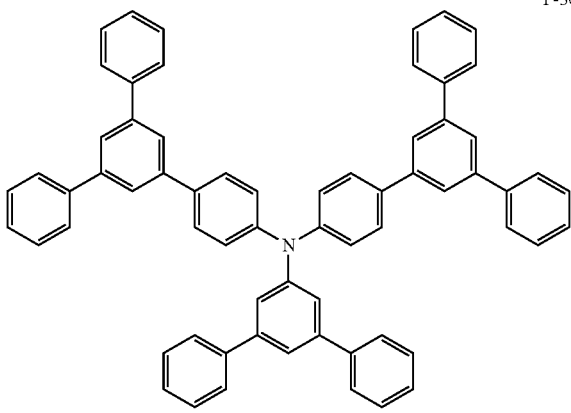
P-31
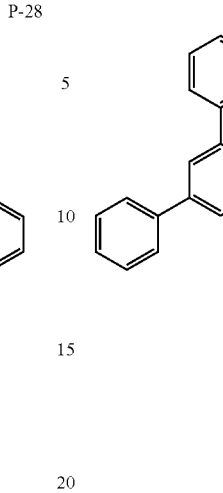
P-32
P-33
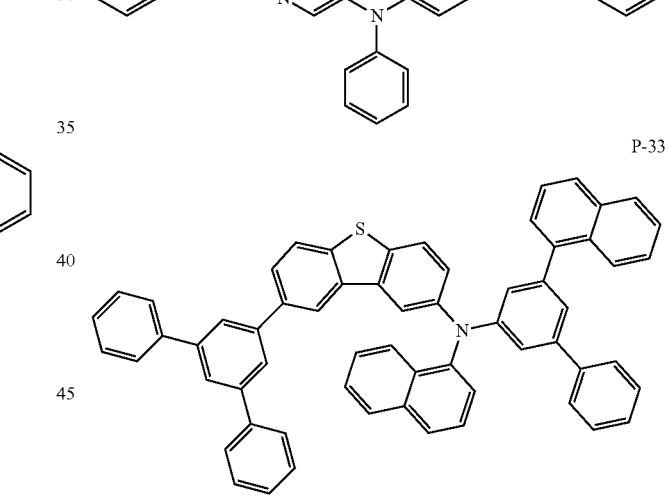
P-34
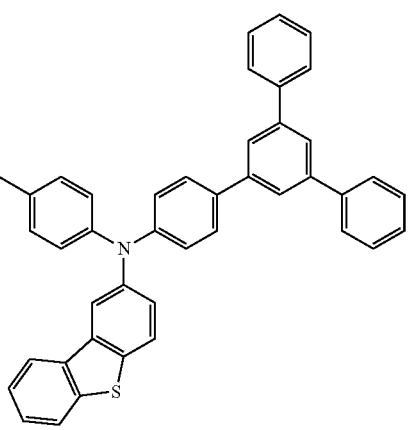

-continued

P-35

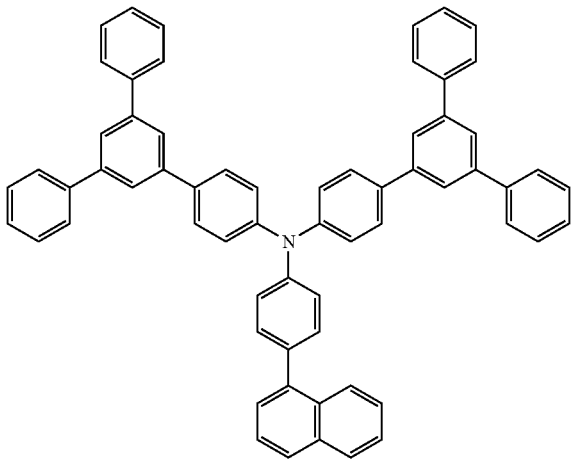

P-36

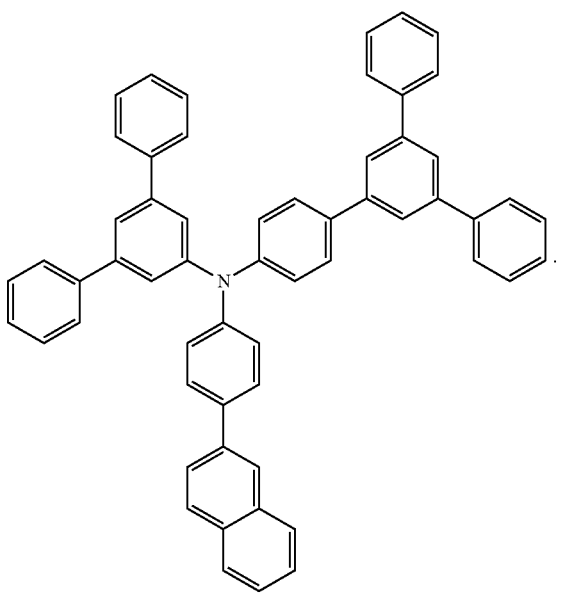

6. The organic electric element of claim 1, wherein the compound is a single compound or a mixture of two or more different compounds.

7. An organic electric element, comprising:
a first electrode,
a second electrode, and
an organic material layer formed between the first electrode and the second electrode, and comprising at least one of a hole transport layer, an emission-auxiliary layer and a light emitting layer, wherein the emission-auxiliary layer comprises a compound represented by Formula 1 below, and the light emitting layer comprises a compound represented by Formula 7 below,

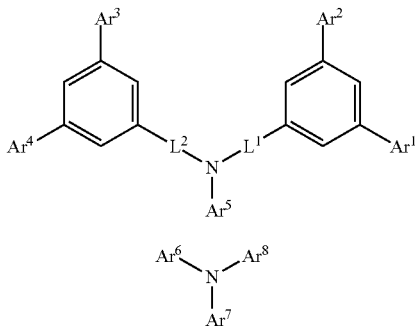

<Formula 1>

<Formula 7> wherein, $Ar^1$ to $Ar^5$ are each independently selected from the group consisting of a $C_6$-$C_{24}$ aryl group; a fluorenyl group; a $C_2$-$C_{25}$ heterocyclic group containing at least one heteroatom selected from the group consisting of O, N, S, Si and P; a fused ring formed by a $C_3$-$C_{24}$ aliphatic ring and a $C_6$-$C_{24}$ aromatic ring; a $C_1$-$C_{20}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group and the combination thereof, $L^1$ and $L^2$ are each independently selected from the group consisting of a single bond, a $C_6$-$C_{24}$ arylene group, a fluorenylene group, a $C_2$-$C_{24}$ heterocyclic group containing at least one heteroatom selected from the group consisting of O, N, S, Si and P, a fused ring formed by a $C_3$-$C_{24}$ aliphatic ring and a $C_6$-$C_{24}$ aromatic ring and the combination thereof, i) $Ar^6$ and $Ar^7$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group, -$L'$-$N(R^a)(R^b)$ and the combination thereof, and ii) $Ar^6$ and $Ar^7$ may be linked together to form a ring, $Ar^8$ is any one of Formulas 7-a, 7-b and 7-c below,

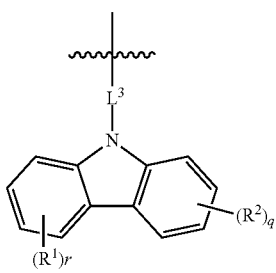

<Formula 7-a>

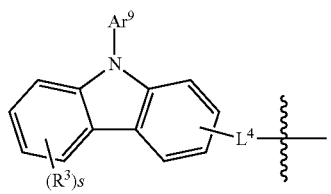

<Formula 7-b>

-continued

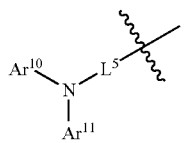

<Formula 7-c> in formulas 7-a, 7-b and 7-c, $Ar^9$ to $Ar^{11}$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group, -L'-N($R^a$)($R^b$) and the combination thereof, i) $R^1$ to $R^3$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, a $C_6$-$C_{30}$ aryloxy group, -L-N($R^a$)($R^b$) and the combination thereof, and ii) adjacent groups of $R^1$s to $R^3$s may be linked together to form a ring, and the group not forming a ring is the same as defined in the above i), q, r and s are each an integer of 0 to 4, and each of plural $R^1$s, $R^2$s and $R^3$s may be same to or different from each other when q, r and s are each an integer of 2 or more, $L^3$ and $L^5$ are each independently selected from the group consisting of a $C_6$-$C_{60}$ arylene group, a fluorenylene group, a fused ring formed by a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si and P, and the combination thereof, $L^4$ is selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, and the combination thereof, L' in $Ar^6$, $Ar^7$, $Ar^9$ to $Ar^{11}$ and $R^1$ to $R^3$ is selected from the group consisting of a single bond, a $C_6$-$C_{60}$ arylene group, a fluorenylene group, a fused ring formed by a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si and P, and $R^a$ and $R^b$ in $Ar^6$, $Ar^7$, $Ar^9$ to $Ar^{11}$ and $R^1$ are each independently selected from the group consisting of a $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si and P, when $Ar^1$ to $Ar^7$, $Ar^9$ to $Ar^{11}$ and $R^1$ to $R^3$ are each independently an aryl group, a fluorenyl group, a heterocyclic group, a fused ring, an alkyl group, an alkenyl group, an alkoxy group, or an aryloxy group, each of $Ar^1$ to $Ar^7$, $Ar^9$ to $Ar^{11}$, and $R^1$ to $R^3$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group, and when $L^1$ to $L^5$ are each independently an arylene group, a fluorenylene group, a heterocyclic group or a fused ring, each of $L^1$ to $L^5$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

8. The organic electric element of claim 7, wherein Formula 7 is any one of the compounds below:

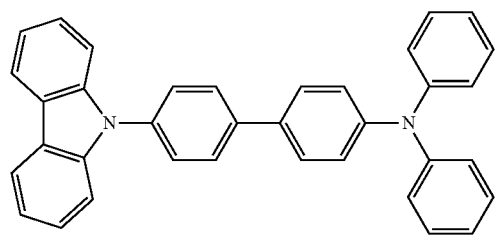

1-1

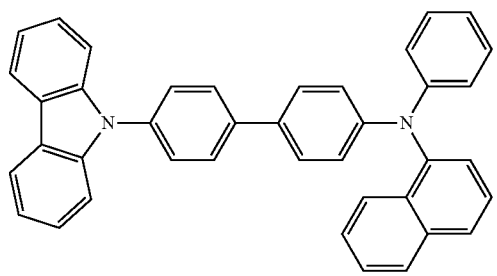

1-2

-continued
1-3
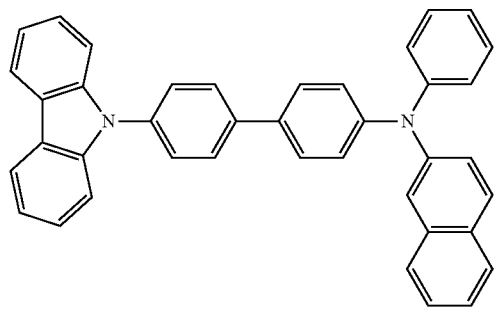
1-4
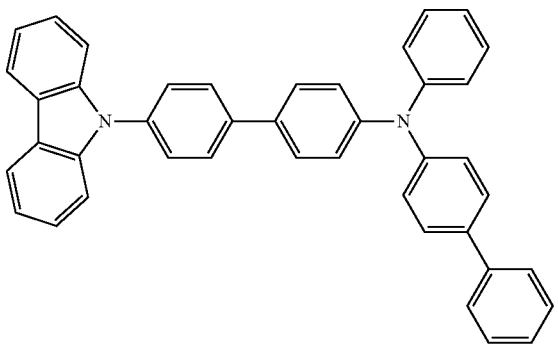
1-5
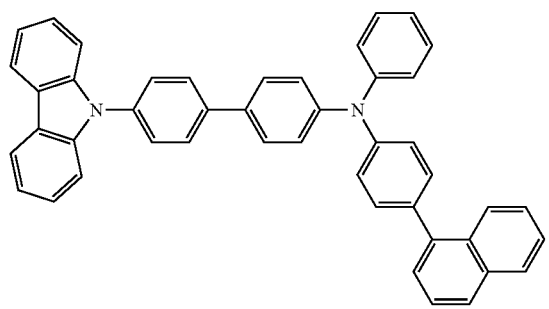
1-6
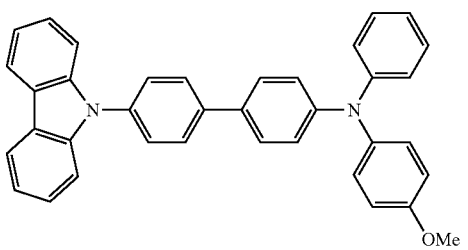
1-7
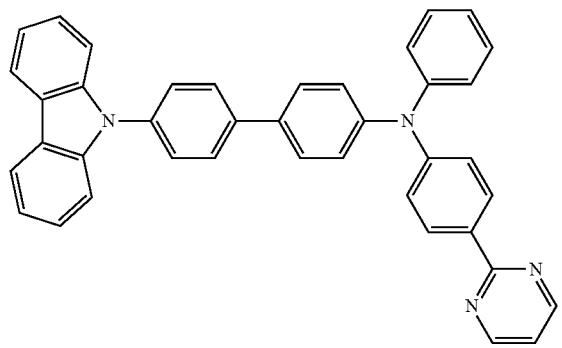
1-8
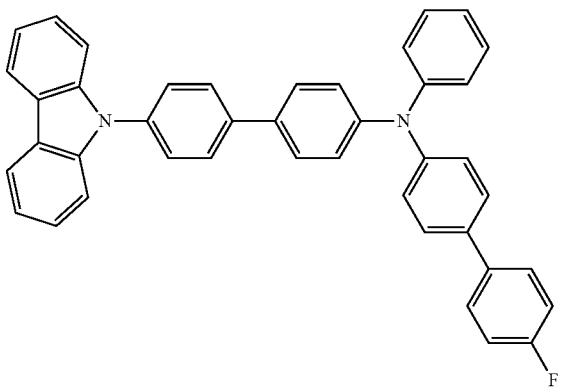
1-9
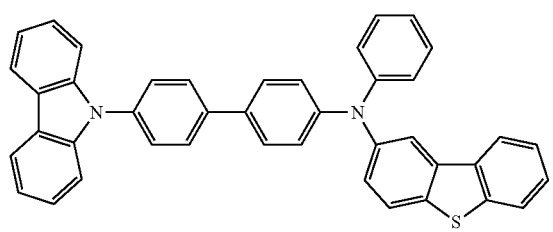
1-10
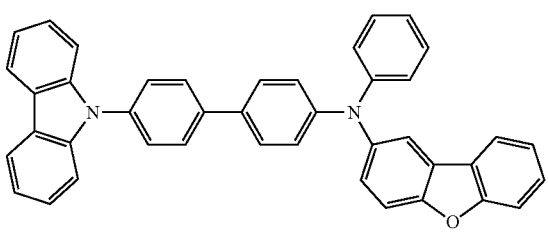

-continued
1-11
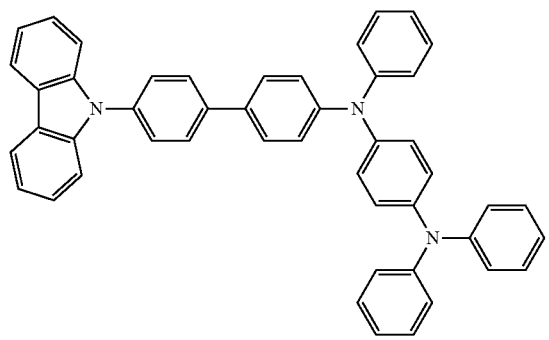
1-12
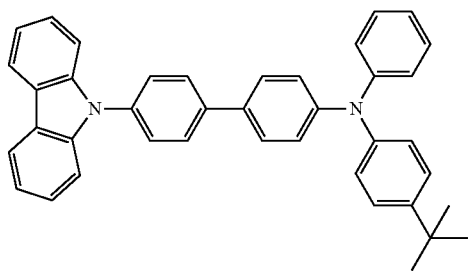
1-13
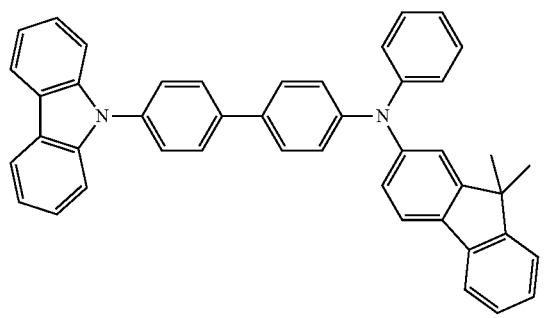
1-14
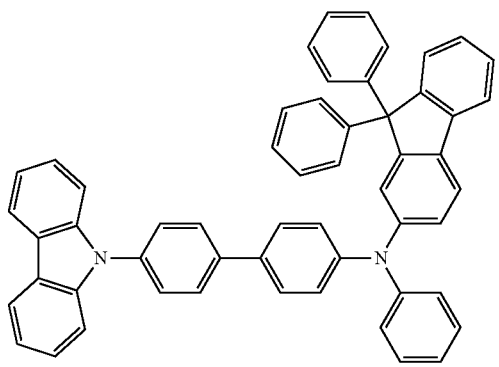
1-15
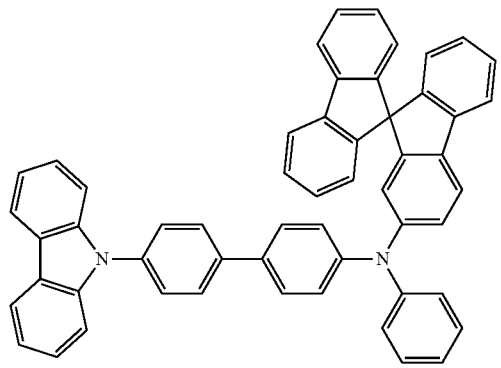
1-16
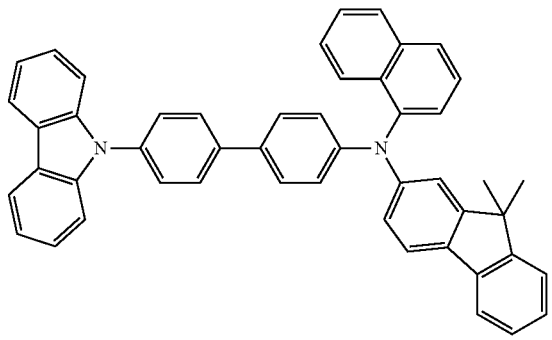
1-17
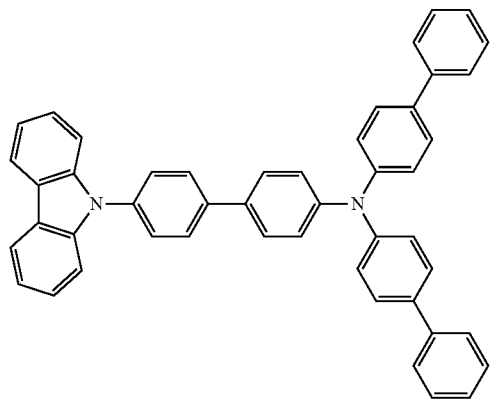
1-18
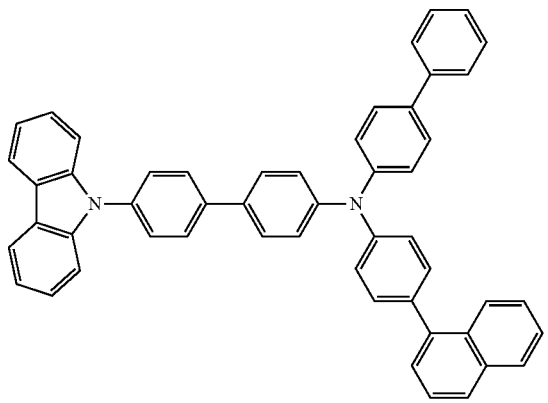

-continued
1-19
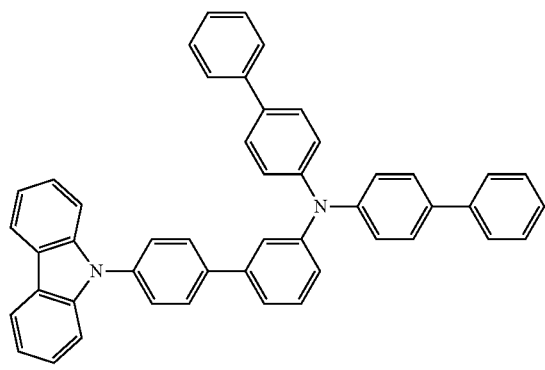
1-20
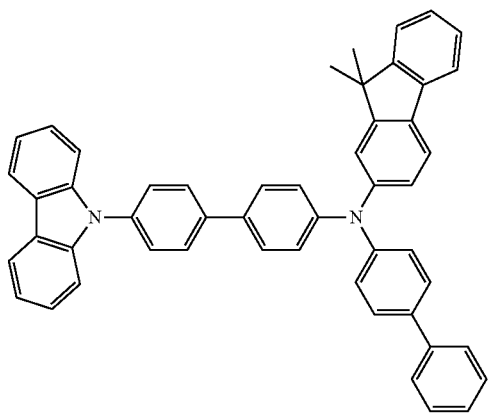
1-21
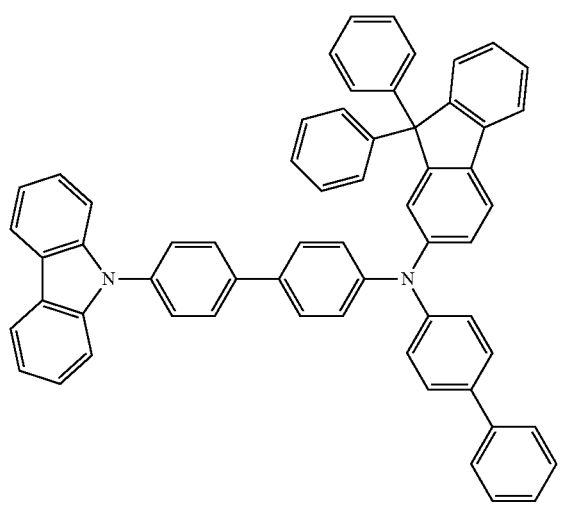
1-22
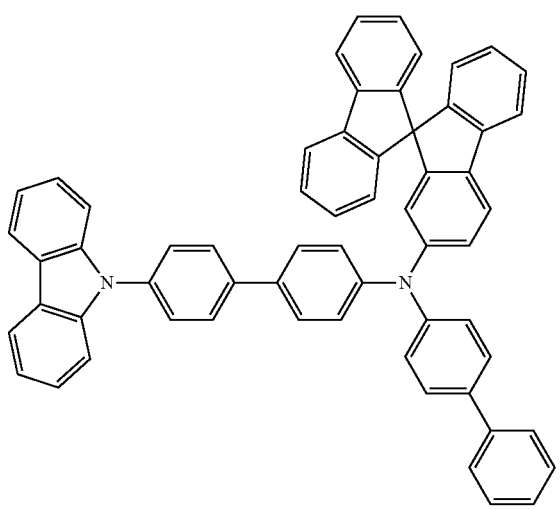
1-23
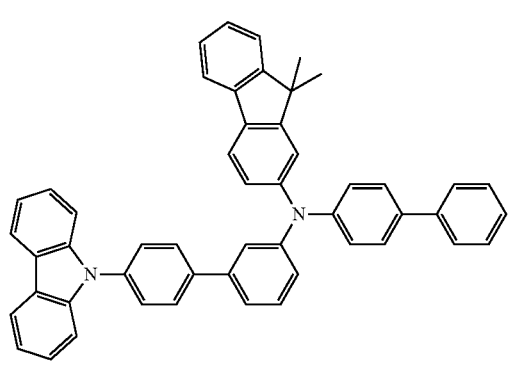
1-24
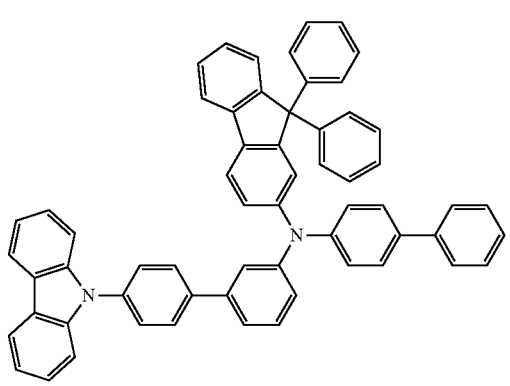

-continued
1-25
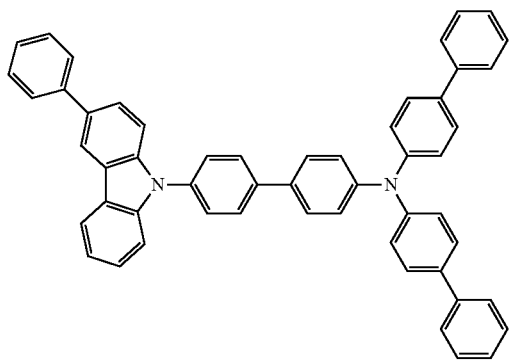
1-26
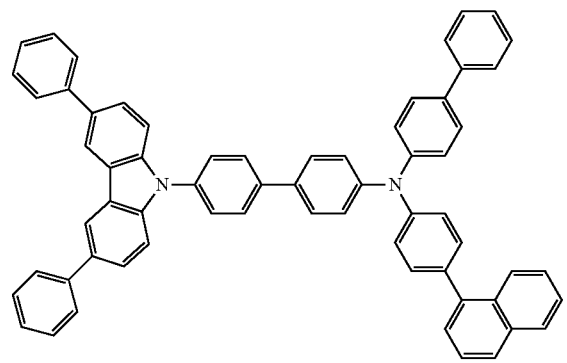
1-27
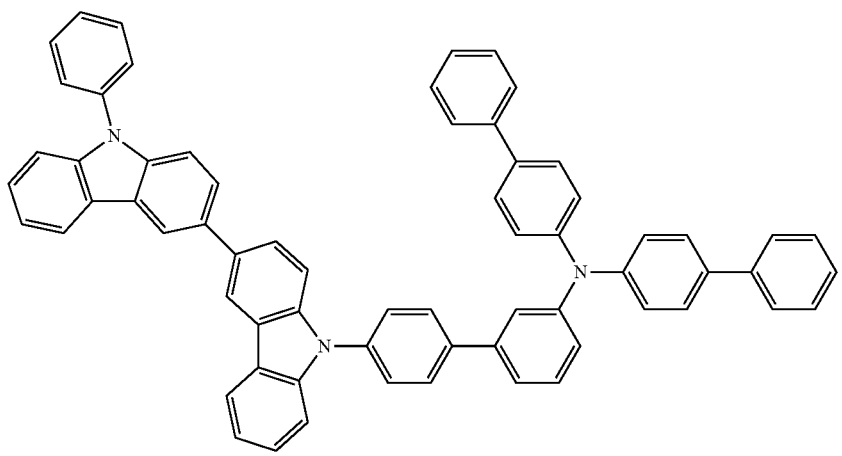
1-28
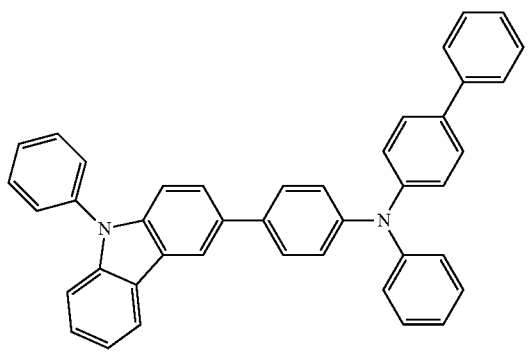
1-29
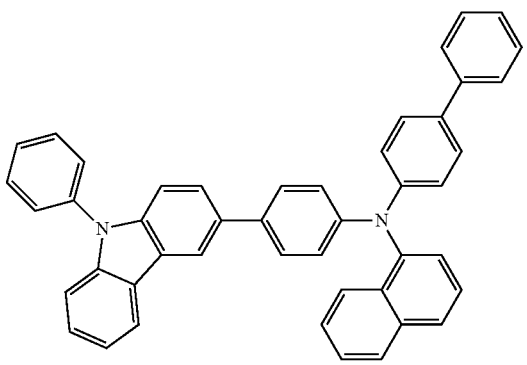

-continued
1-30
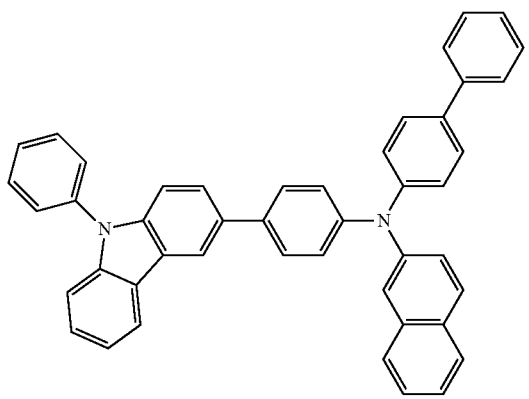
1-31
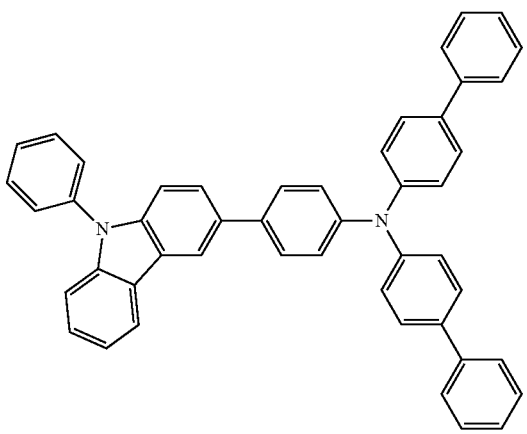
1-32
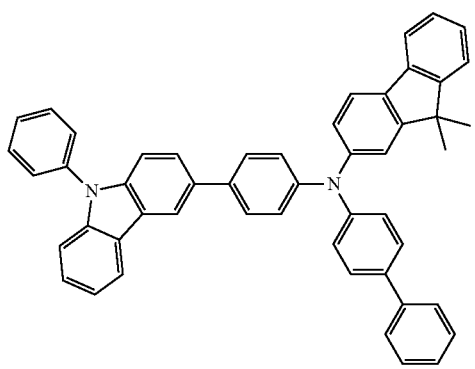
1-33
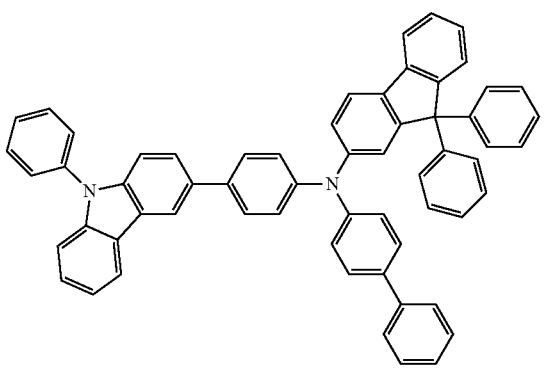
1-34
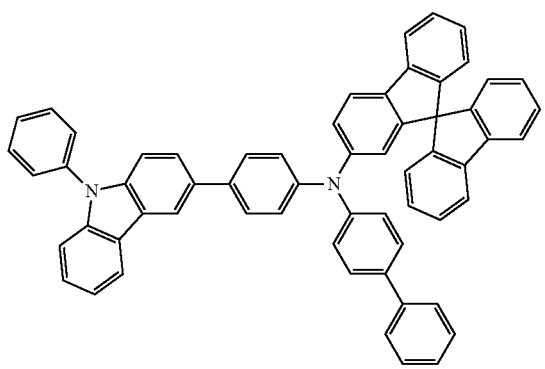
1-35
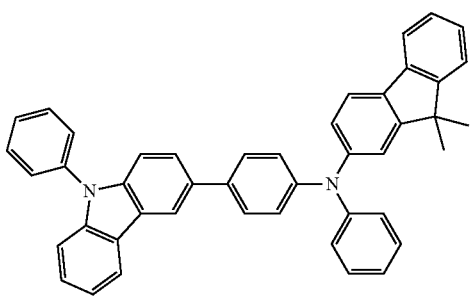
1-36
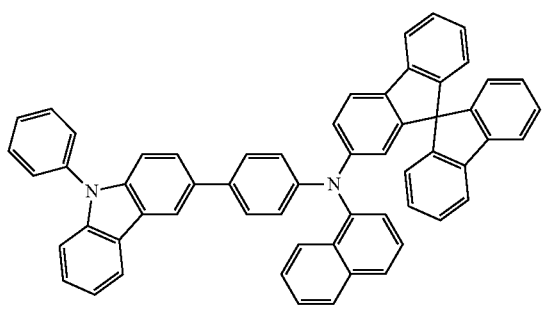
1-37
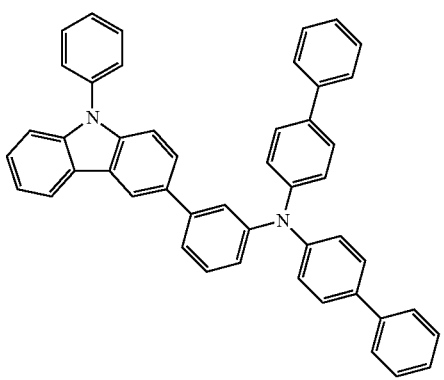

-continued
1-38
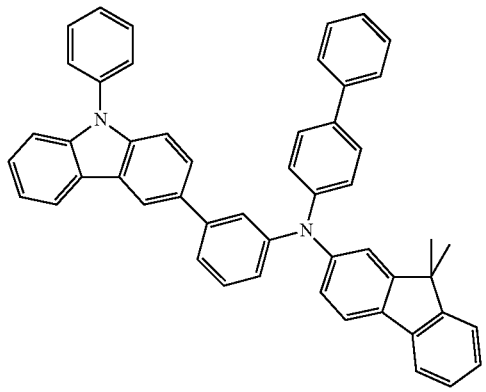
1-39
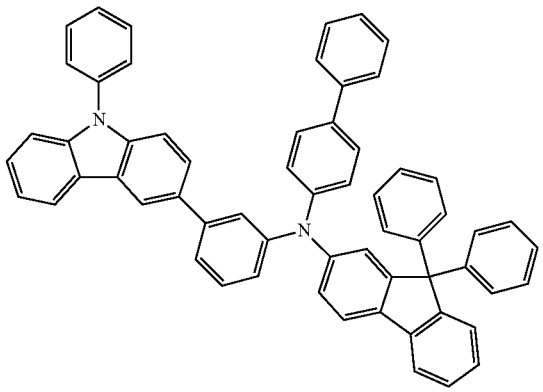
1-40
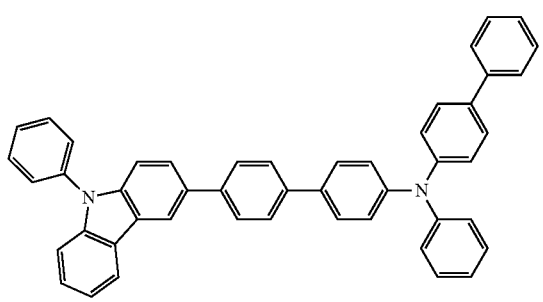
1-41
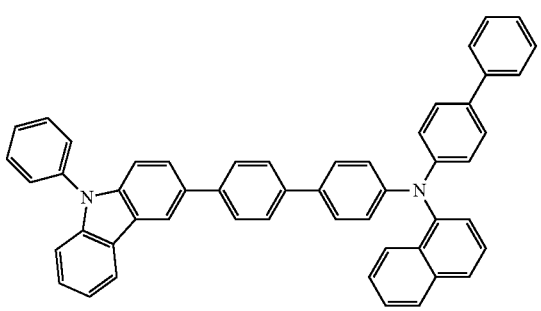
1-42
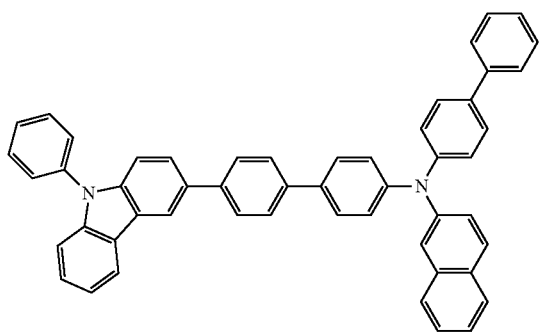
1-43
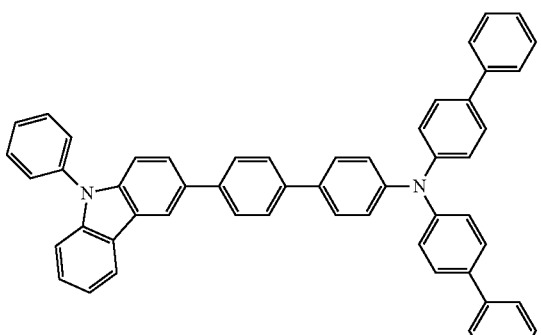
1-44
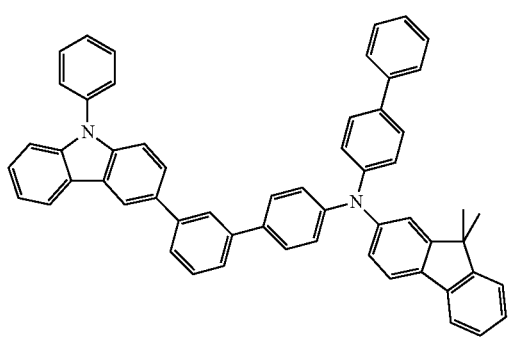
1-45
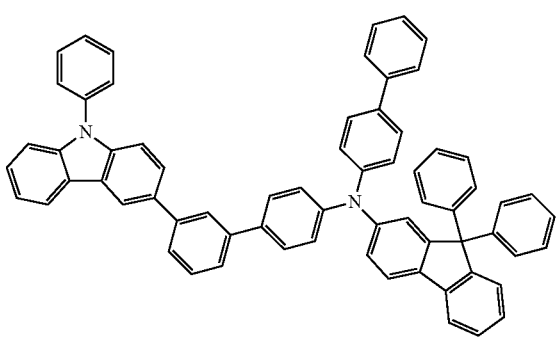

-continued
1-46
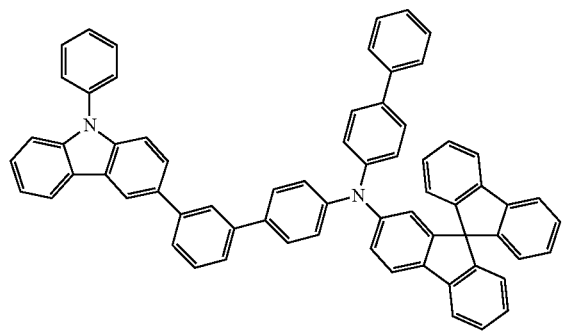
1-47
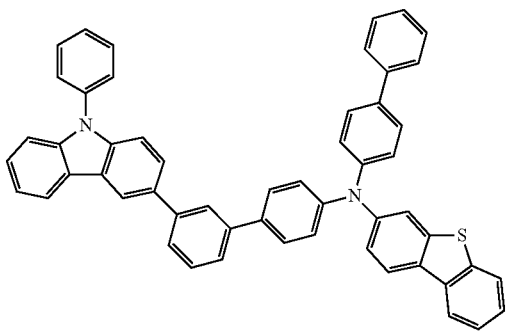
1-48
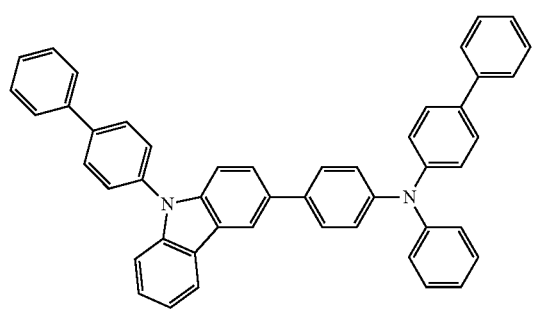
1-49
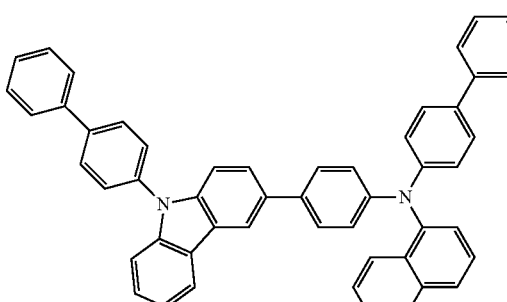
1-50
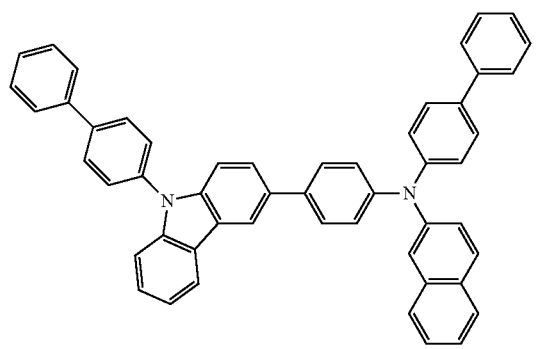
1-51
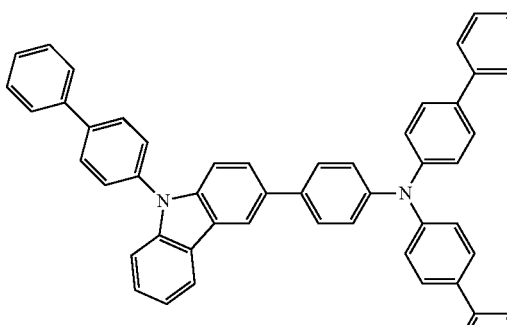
1-52
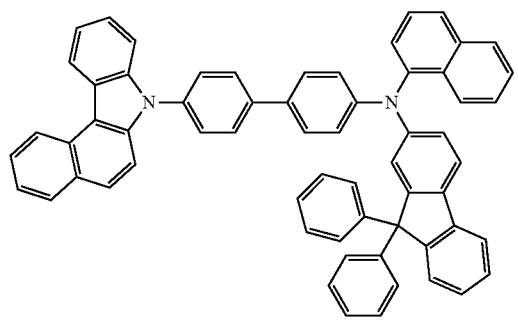
1-53
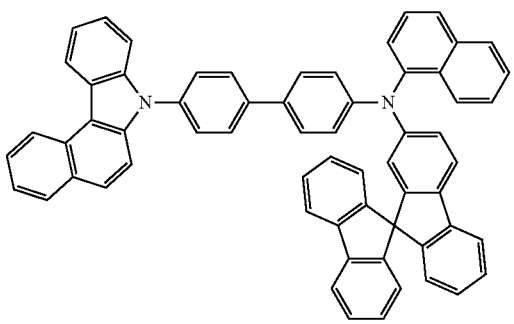

-continued
1-54
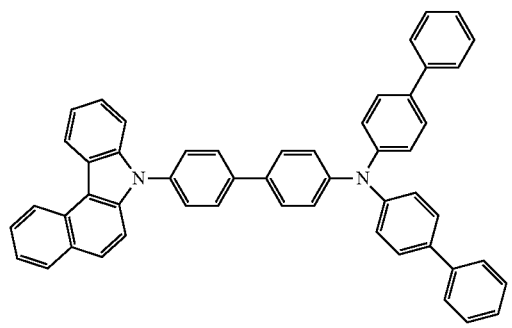
1-55
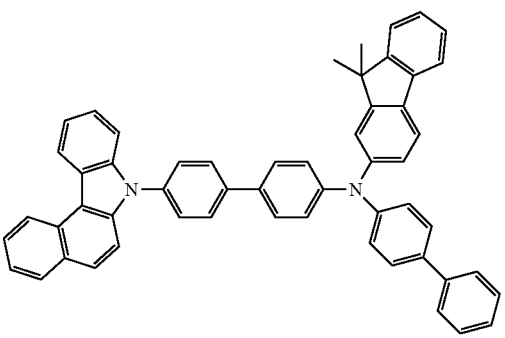
1-56
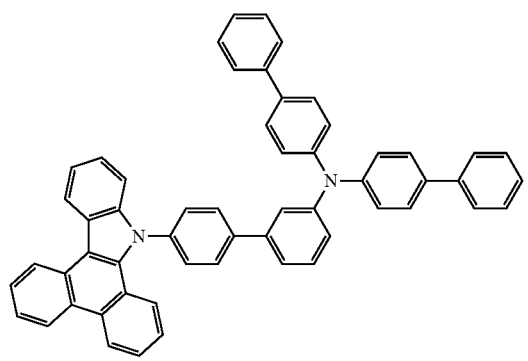
1-57
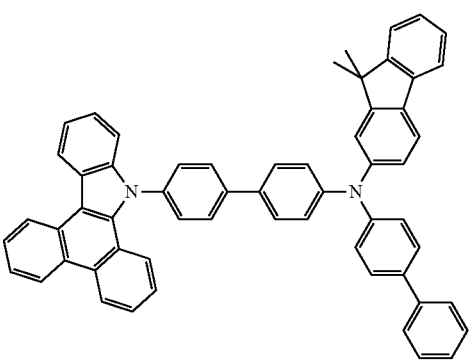
1-58
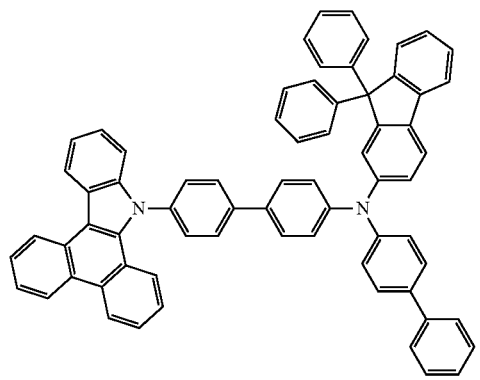
1-59
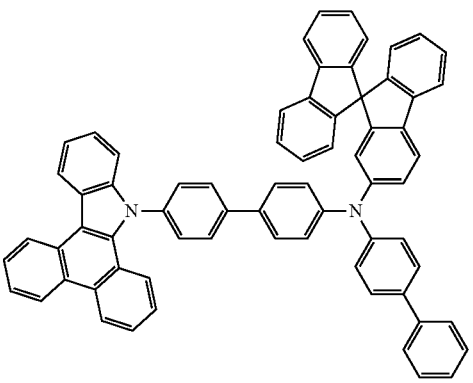
1-60
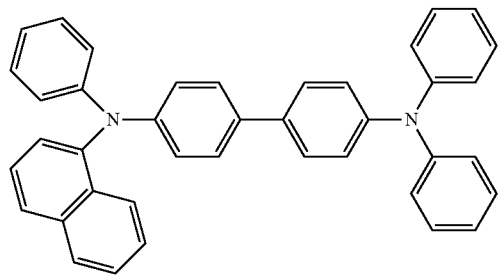
1-61
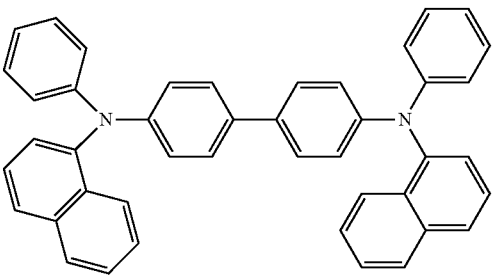

1-62
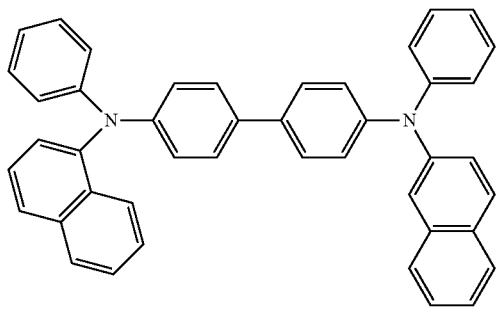
1-63
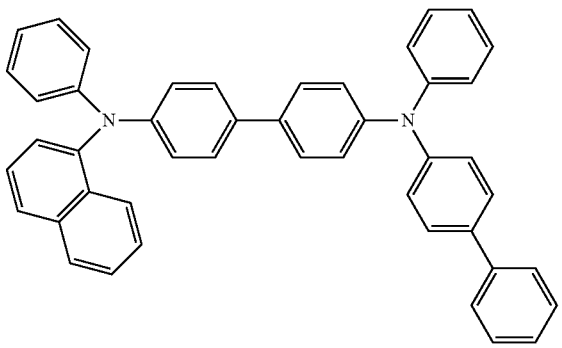
1-64
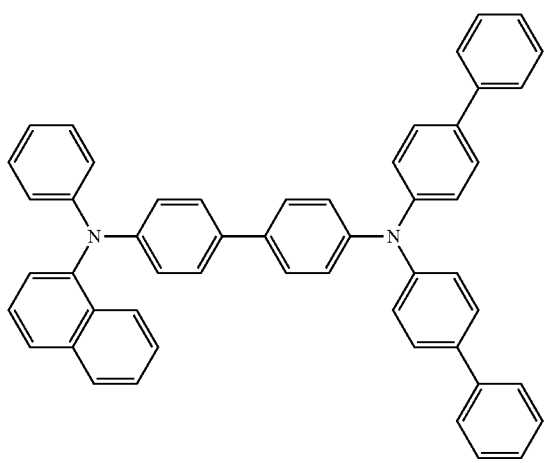
1-65
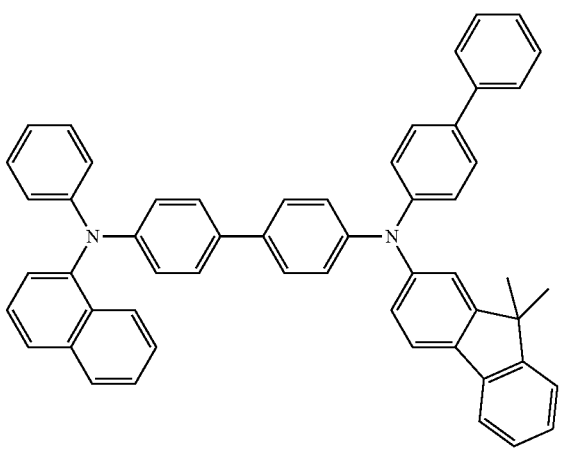
1-66
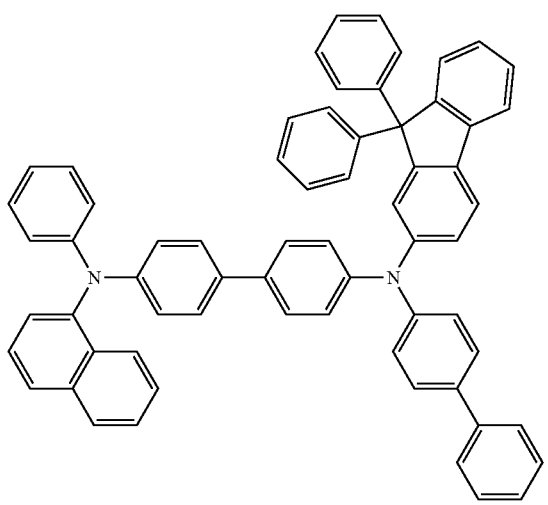
1-67
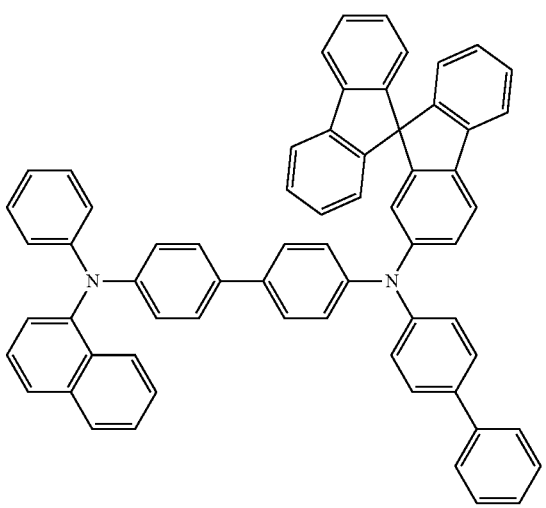

-continued 1-68
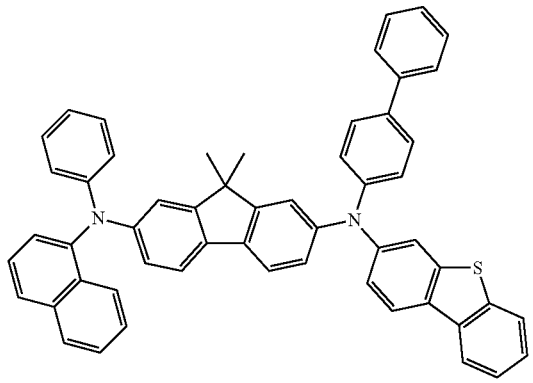

1-69
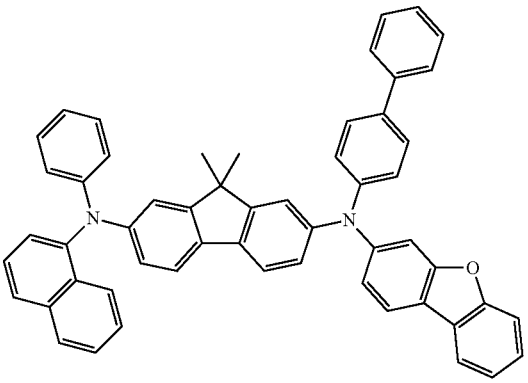

1-70
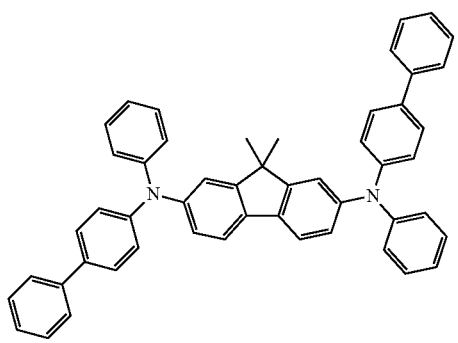

1-71
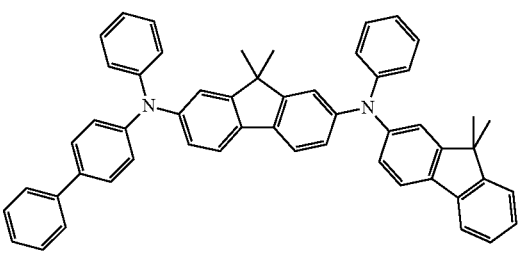

9. The organic electric element as claimed in claim 1, further including at least one layer to improve luminous efficiency formed on at least one of the sides of the first and second electrodes facing organic material layer.

10. The organic electric element as claimed in claim 1, wherein the organic material layer is formed by any one of the process of spin coating, nozzle printing, inkjet printing, slot coating, dip coating and roll-to-roll.

11. An electronic device, comprising:
a display device which comprises the organic electric element of claim 1, and
a control unit for driving the display device.

12. The electronic device of claim 11, wherein the organic electric element comprises an organic light emitting diode, an organic solar cell, an organic photo conductor, an organic transistor, or an element for monochromatic or white illumination.

* * * * *